(12) United States Patent
Kim et al.

(10) Patent No.: US 8,481,243 B2
(45) Date of Patent: Jul. 9, 2013

(54) RESIN AND PHOTORESIST COMPOSITION COMPRISING THE SAME

(75) Inventors: Hyungjoo Kim, Osaka (JP); Akira Kamabuchi, Osaka (JP); Koji Ichikawa, Osaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 13 days.

(21) Appl. No.: 13/345,941

(22) Filed: Jan. 9, 2012

(65) Prior Publication Data

US 2012/0178021 A1    Jul. 12, 2012

(30) Foreign Application Priority Data

Jan. 12, 2011    (JP) .................... 2011-003778

(51) Int. Cl.
*G03F 7/039* (2006.01)
*G03F 7/20* (2006.01)
*G03F 7/30* (2006.01)
*G03F 7/38* (2006.01)

(52) U.S. Cl.
USPC ........ 430/270.1; 430/311; 430/325; 430/326; 430/330; 430/905; 430/910; 526/257; 549/33; 549/40; 549/30; 549/31; 549/32; 549/87

(58) Field of Classification Search
None
See application file for complete search history.

(56) References Cited

U.S. PATENT DOCUMENTS

2012/0107744 A1*  5/2012  Utsumi et al. ............. 430/283.1
2012/0122034 A1*  5/2012  Ichikawa et al. ........... 430/285.1

* cited by examiner

*Primary Examiner* — Sin J. Lee
(74) *Attorney, Agent, or Firm* — Birch, Stewart, Kolasch & Birch, LLP

(57) ABSTRACT

The present invention provides a resin comprising a structural unit represented by the formula (aa):

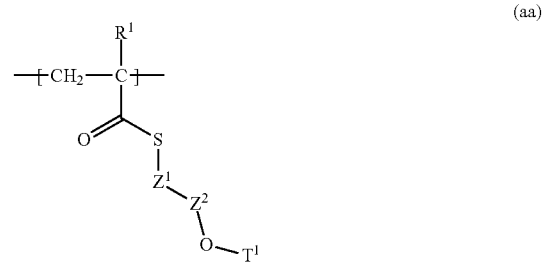

(aa)

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

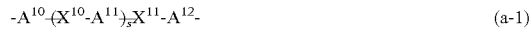

(a-1)

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—.

13 Claims, No Drawings

RESIN AND PHOTORESIST COMPOSITION COMPRISING THE SAME

This nonprovisional application claims priority under 35 U.S.C. §119(a) on Patent Application No. 2011-003778 filed in JAPAN on Jan. 11, 2011, the entire contents of which are hereby incorporated by reference.

FIELD OF THE INVENTION

The present invention relates to a resin and a photoresist composition comprising the same.

BACKGROUND OF THE INVENTION

A photoresist composition is used for semiconductor microfabrication employing a lithography process. The photoresist composition comprises an acid generator and a resin having an acid-labile group, being insoluble or poorly soluble in an aqueous alkali solution but becoming soluble in an aqueous alkali solution by the action of an acid.

US 2009/0068590 A1 discloses a resin consisting of the following structural units.

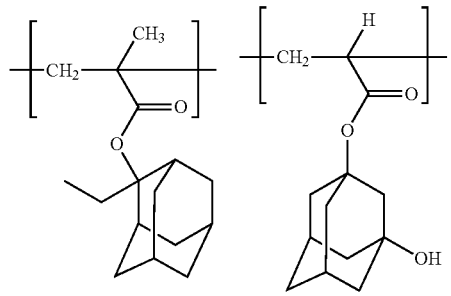

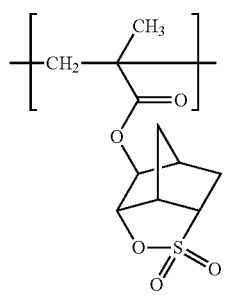

SUMMARY OF THE INVENTION

The present invention is to provide a resin and a photoresist composition comprising the same.

The present invention relates to the followings:

[1] A resin comprising a structural unit represented by the formula (aa):

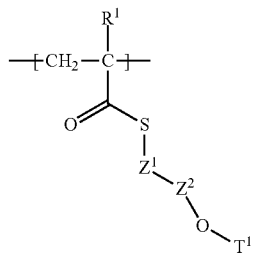

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—;

[2] The resin according to [1], wherein total carbon number of $A^{10}$, $A^{11}$ and $A^{12}$ is 6 or less;

[3] The resin according to [1] or [2], wherein $T^1$ is a polycyclic sultone ring group in the formula (aa);

[4] The resin according to [1] or [2], wherein $T^1$ is a group represented by the formula (T1):

(T1)

wherein $Z^{12}$ represents —O—, —S— or —CH$_2$—, one or two hydrogen atoms in —CH$_2$— in the formula (T1) may be replaced by a halogen atom, a hydroxyl group, an oxo group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group or a C2-C4 acyl group, and * represents a binding position to —O—, in the formula (aa);

[5] The resin according to any one of [1] to [4], wherein $Z^2$ is —CO— in the formula (aa);

[6] The resin according to any one of [1] to [5], wherein $Z^1$ is —CH$_2$— in the formula (aa);

[7] The resin according to any one of [1] to [6], wherein the resin is one being insoluble or poorly soluble in an aqueous alkali solution but becoming soluble in an aqueous alkali solution by the action of an acid;

[8] A photoresist composition comprising the resin according to [7] and an acid generator;

[9] The photoresist composition according to [8], which further comprises a solvent;

[10] The photoresist composition according to [8], which further comprises a basic compound;

[11] The photoresist composition according to [9], which further comprises a basic compound;
[12] A process for producing a photoresist pattern comprising:
(1) a step of applying the photoresist composition according to [8], [9], [10] or [11] on a substrate to form a photoresist composition layer,
(2) a step of forming a photoresist film by drying the photoresist composition layer formed,
(3) a step of exposing the photoresist film to radiation,
(4) a step of heating the photoresist film after exposing, and
(5) a step of developing the photoresist film after heating;
[13] A compound represented by the formula (aa'):

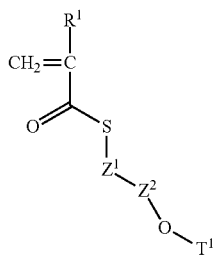

(aa')

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

(a-1)

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—.

DESCRIPTION OF PREFERRED EMBODIMENTS

The resin of the present invention (hereinafter, simply referred to as RESIN (A)) comprises a structural unit represented by the formula (aa):

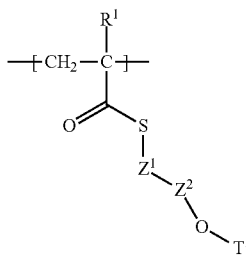

(aa)

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

(a-1)

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—.

In this specification, "sultone ring group" means a cyclic group having —O—$SO_2$— within a ring structure. The cyclic group can further contain one or more heteroatoms such as an oxygen atom, a sulfur atom and a nitrogen atom, and as the heteroatom, an oxygen atom is preferable.

Examples of the sultone ring group include the group represented by the following formula ($T^1$-1), ($T^1$-2), ($T^1$-3), ($T^1$-4) or ($T^1$-5), and in the following formulae, * represents a binding position to —O—.

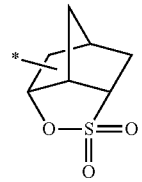

($T^1$-1)

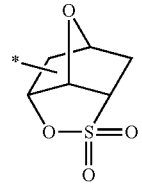

($T^1$-2)

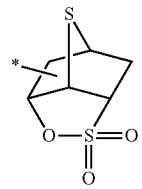

($T^1$-3)

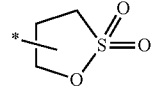

($T^1$-4)

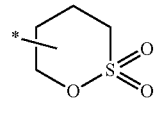

($T^1$-5)

The sultone ring group may have one or more substituents, and examples thereof include a halogen atom, a hydroxyl group, an oxo group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group and a C2-C4 acyl group.

Examples of the halogen atom include a fluorine atom, a chlorine atom, a bromine atom and an iodine atom.

Examples of the C1-C12 alkyl group include a linear or branched chain alkyl group such as a methyl group, an ethyl group, a propyl group, an isopropyl group, a butyl group, an isobutyl group, a tert-butyl group, a pentyl group, a hexyl group, a heptyl group, an octyl group, a decyl group and a dodecyl group, and a C1-C6 alkyl group is preferable and a methyl group is more preferable.

Examples of the C1-C12 alkyl group having a halogen atom or a hydroxyl group include a hydroxymethyl group, a hydroxyethyl group and a trifluoromethyl group.

Examples of the C1-C12 alkoxy group include a linear or branched chain alkoxy group such as a methoxy group, an ethoxy group, a propoxy group, an isopropoxy group, a butoxy group, an isobutoxy group, a tert-butoxy group, a pentyloxy group, a hexyloxy group, a heptyloxy group, an octyloxy group, a decyloxy group and a dodecyoxy group.

Examples of the C6-C12 aryl group include a phenyl group, a naphthyl group, an anthryl group and a biphenyl group.

Examples of the C7-C12 aralkyl group include a benzyl group, a phenylethyl group, a phenylpropyl group, a naphthylmethyl group and a naphthylethyl group.

The C2-C12 alkoxycarbonyl group is a group formed by bonding a C1-C11 alkoxy group with a carbonyl group, and examples thereof include a methoxycarbonyl group, an ethoxycarbonyl group, a propoxycarbonyl group, an isopropoxycarbonyl group, a butoxycarbonyl group, an isobutoxycarbonyl group, a tert-butoxycarbonyl group, a pentyloxycarbonyl group, a hexyloxycarbonyl group, a heptyloxycarbonyl group, an octyloxycarbonyl group and a decyloxycarbonyl group, and a C2-C6 alkoxycarbonyl group is preferable and a methoxycarbonyl group is more preferable.

Examples of the C2-C4 acyl group include an acetyl group, a propionyl group and a butyryl group.

From the viewpoint of easy production of a monomer giving the structural unit represented by the formula (aa), an unsubstituted sultone ring group is preferable.

The sultone ring group may be a monocyclic sultone ring group or a polycyclic sultone ring group, and the polycyclic sultone ring group is preferable.

It is preferred that $T^1$ is a group represented by the formula (T1):

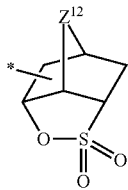

(T1)

wherein $Z^{12}$ represents —O—, —S— or —CH$_2$—, one or two hydrogen atoms in —CH$_2$— in the formula (T1) may be replaced by a halogen atom, a hydroxyl group, an oxo group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group or a C2-C4 acyl group, and * represents a binding position to —O—, in the formula (aa), and it is more preferred that $T^1$ is an unsubstituted group represented by the formula (T1) from the viewpoint of easy production.

$Z^{12}$ is preferably —O— or —CH$_2$—, and more preferably —CH$_2$—.

Preferable examples of $T^1$ include the following groups, and in the following formulae, * represents a binding position to —O—.

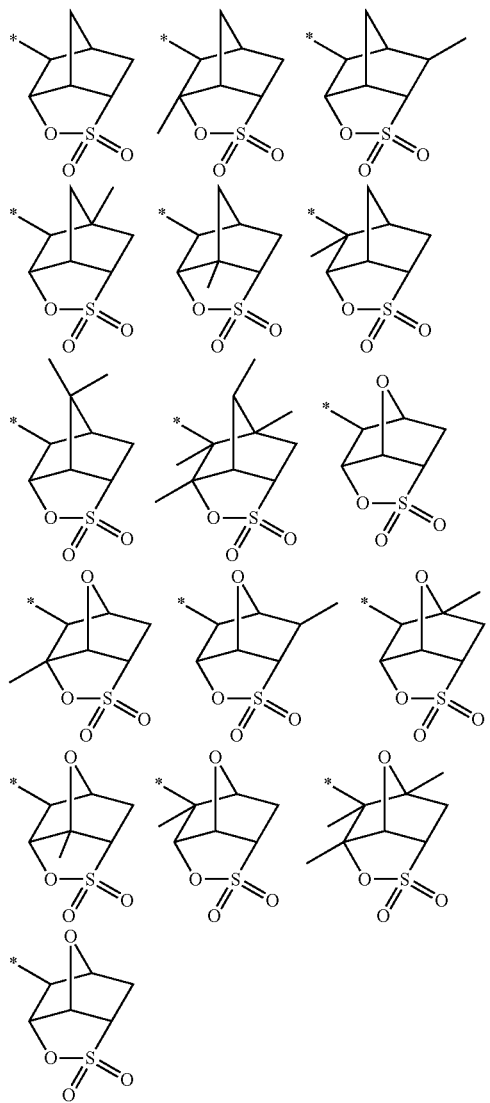

In the formula (aa), $Z^1$ represents a C1-C6 alkanediyl group optionally having one or more substituents, or a group represented by the formula (a-1):

$$-A^{10}-(X^{10}-A^{11})_s-X^{11}-A^{12}-$$ (a-1)

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1.

The alkanediyl group may be a linear group or a branched chain group. Examples thereof include a methylene group, an ethane-1,1-diyl group, an ethane-1,2-diyl group, a propane-1,1-diyl group, a propane-2,2-diyl group, a propane-1,3-diyl group, a propane-1,2-diyl group, a butane-1,3-diyl group, a butane-1,4-diyl group, a pentane-1,5-diyl group, a 2-methylpropane-1,3-diyl group, a 2-methylpropane-1,2-diyl group, a pentane-1,4-diyl group and a 2-methylbutane-1,4-diyl group.

The alkanediyl group may have one or more substituents, and examples thereof include a hydroxyl group and a C1-C6 alkoxy group.

Examples of the C1-C5 divalent aliphatic hydrocarbon group include a C1-C5 alkanediyl group such as a methylene group, an ethane-1,1-diyl group, an ethane-1,2-diyl group, a propane-1,1-diyl group, a propane-2,2-diyl group, a propane-1,3-diyl group, a propane-1,2-diyl group, a butane-1,3-diyl group, a butane-1,4-diyl group, a pentane-1,5-diyl group, a 2-methylpropane-1,3-diyl group, a 2-methylpropane-1,2-diyl group, a pentane-1,4-diyl group and a 2-methylbutane-1,4-diyl group. The C1-C5 divalent aliphatic hydrocarbon group may have one or more substituents, and examples thereof include a hydroxyl group and a C1-C6 alkoxy group.

Examples of the group represented by the formula (a-1) include the following in which * represents a binding position to a neighboring atom.

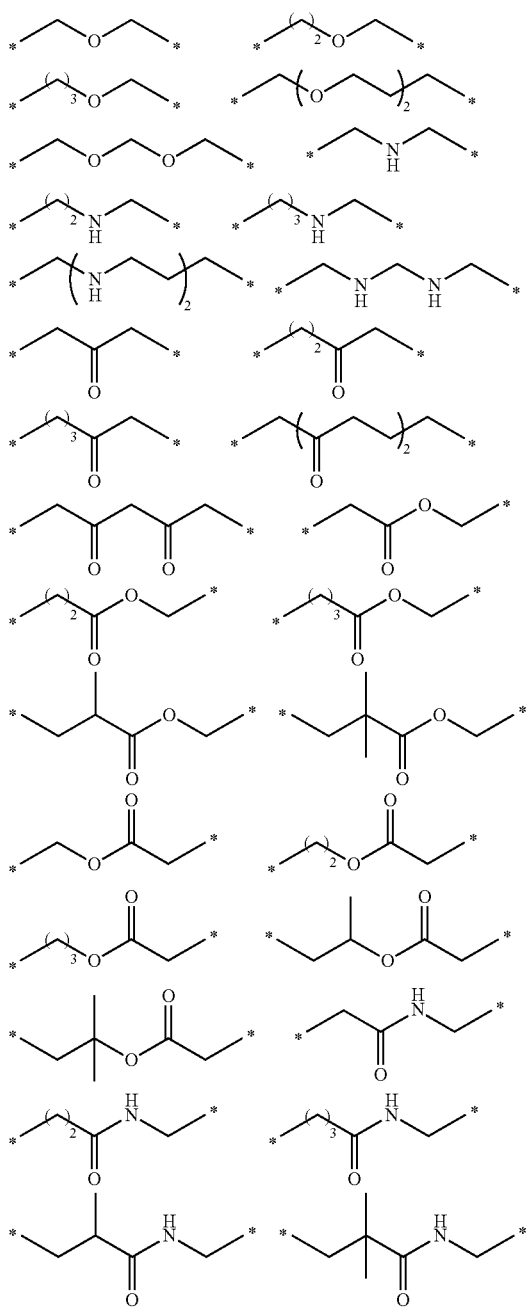

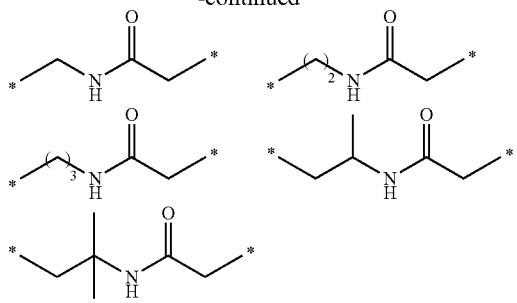

Total carbon number of $A^{10}$, $A^{11}$ and $A^{12}$ is preferably 6 or less.

$Z^1$ is preferably a C1-C6 alkanediyl group, and more preferably a C1-C4 alkanediyl group, and still more preferably a methylene group.

$Z^2$ represents a single bond or —CO—, and $Z^2$ is preferably —CO—.

$R^1$ is preferably an unsubstituted C1-C6 alkyl group or a hydrogen atom, more preferably a methyl group or a hydrogen atom.

Examples of the structural unit represented by the formula (aa) include the structural units represented by the formulae (aa-1) to (aa-24).

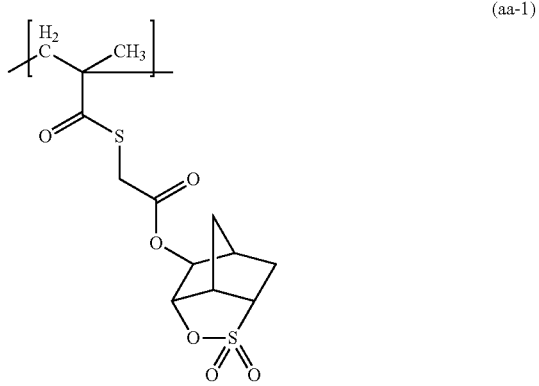

(aa-1)

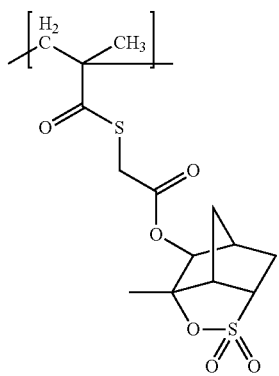

(aa-2)

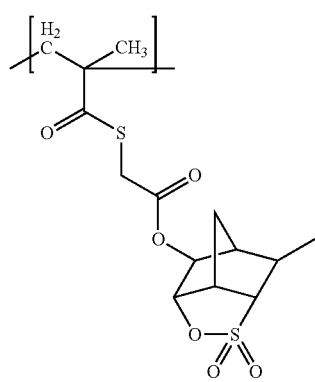
(aa-3)
(aa-4)
(aa-5)
(aa-6)
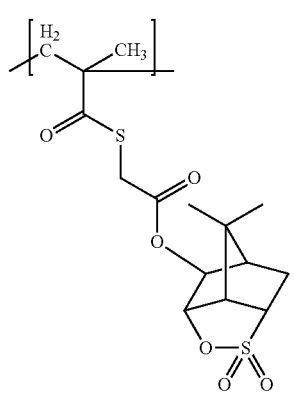
(aa-7)
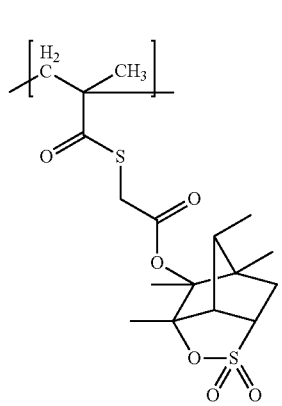
(aa-8)
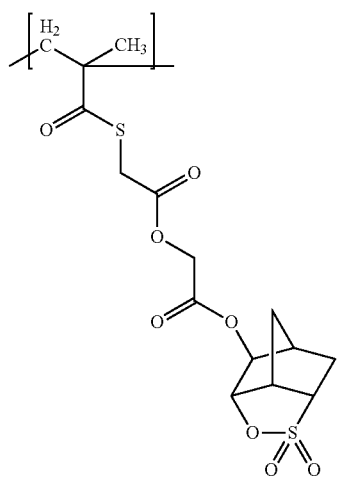
(aa-9)

(aa-10)
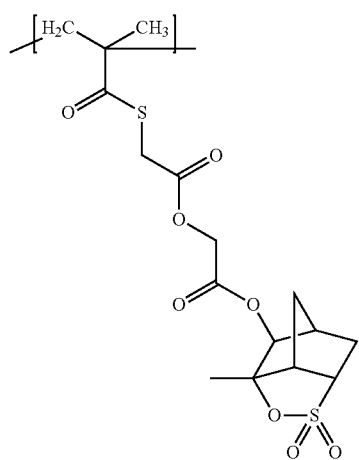
(aa-11)
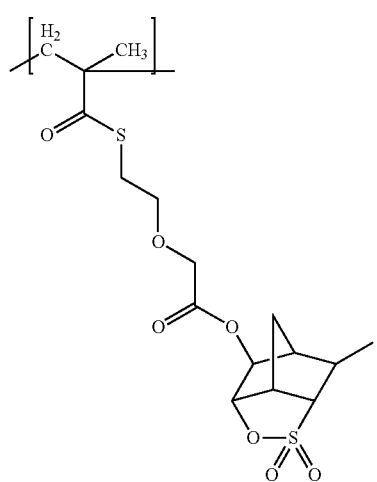
(aa-12)
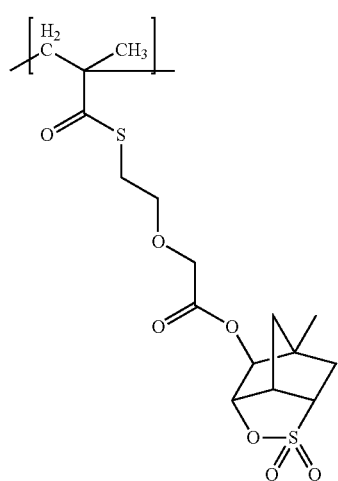
(aa-13)
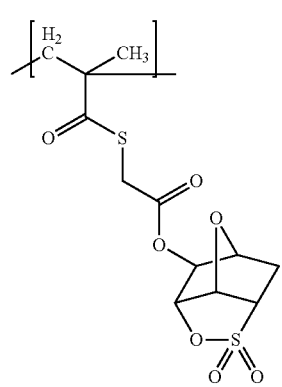
(aa-14)
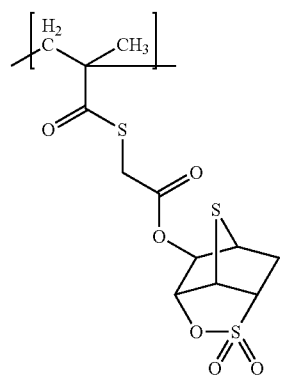
(aa-15)
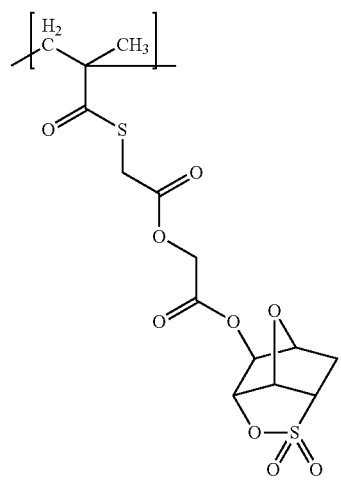

(aa-16) 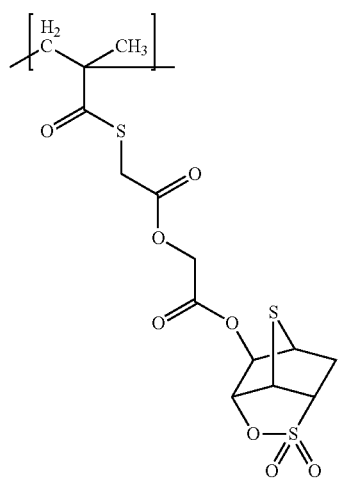
(aa-19) 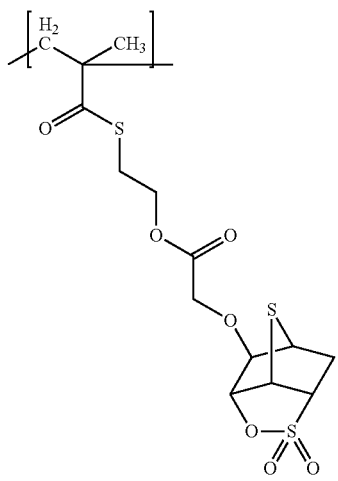
(aa-17) 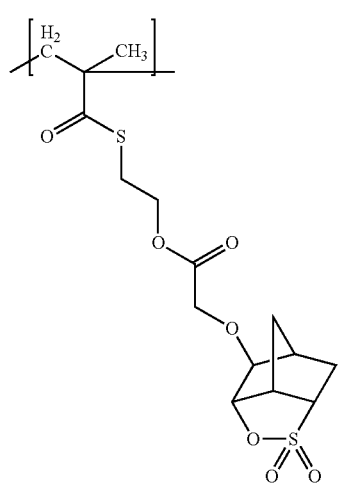
(aa-20) 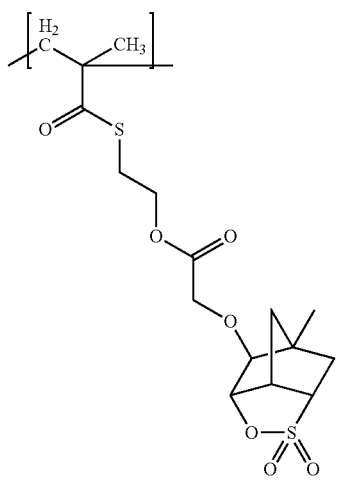
(aa-18) 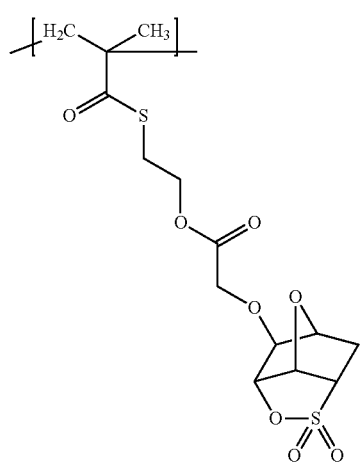
(aa-21) 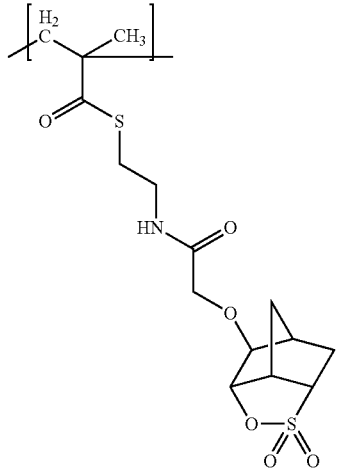

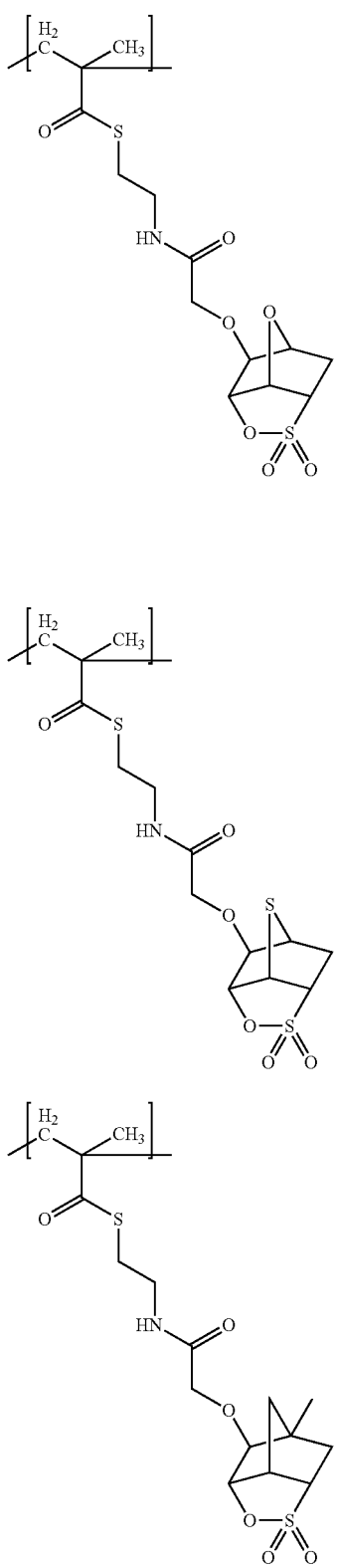

(aa-22)

(aa-23)

(aa-24)

Examples of the structural unit represented by the formula (aa) include the structural units represented by the formulae (aa-1) to (aa-24) wherein the following partial structure M is replaced by the following partial structure A1.

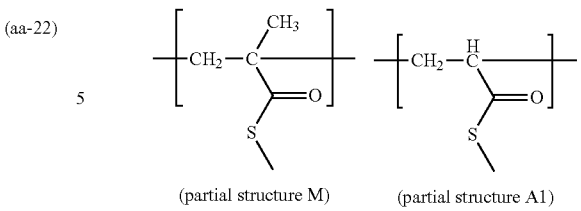

(partial structure M)   (partial structure A1)

The structural unit represented by the formula (aa) is derived from a compound represented by the formula (aa'):

(aa')

wherein $R^1$, $T^1$, $Z^1$ and $Z^2$ are the same as defined above (hereinafter, simply referred to as the compound (aa')).

The compound (aa') can be produced by the following. For example, the compound (aa) wherein $X^2$ is —O— and $Z^1$ is —CO— can be produced by reacting a compound represented by the formula (aa1-a) with a compound represented by the formula (aa1-b) in a solvent such as tetrahydrofuran in the presence of a dehydrating agent such as 1-(3-dimethylaminopropyl)-3-ethylcarbodiimide and a basic catalyst such as dimethylaminopyridine.

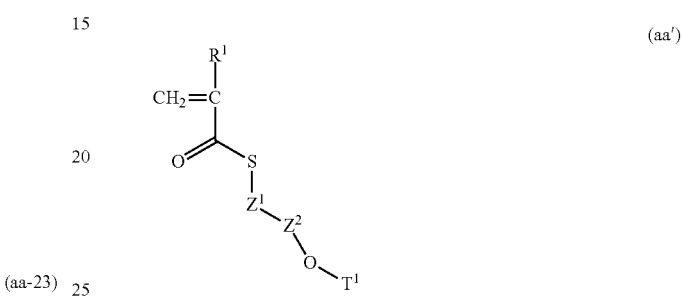

(aa1-a)   (aa1-b)

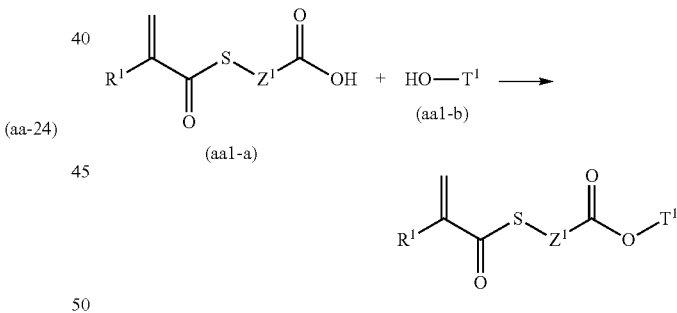

Examples of the compound represented by the formula (aa1-b) include compounds formed by bonding —OH to * of the groups represented by the above-mentioned formulae ($T^1$-1) to ($T^1$-4). Examples of the compound represented by the formula (aa1-b) include the following, and this compound is commercially available.

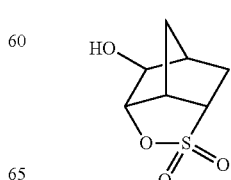

The compound represented by the formula (aa1-a) can be produced according to known methods. For example, the compound represented by the formula (aa1-a) can be produced by reacting a compound represented by the formula (aa1-c) with a compound represented by the formula (aa1-d) in a solvent such as acetonitrile in the presence of a basic catalyst such as triethylemine and dimethylaminopyridine.

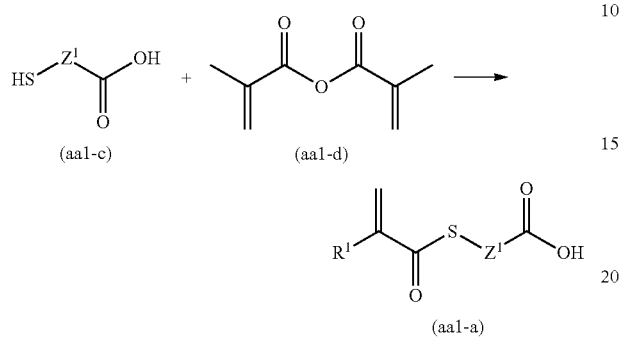

(aa1-c)   (aa1-d)

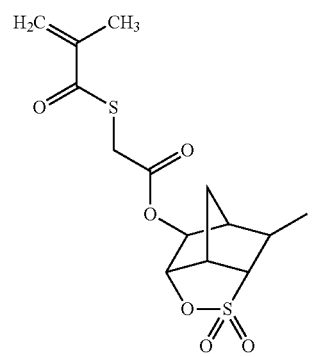

(aa1-a)

Examples of the compound represented by the formula (aa1-c) include thioglycolic acid which is commercially available.

Examples of the compound represented by the formula (aa1-d) include methacrylic anhydride which is commercially available.

Examples of the compound represented by the formula (aa') include the following.

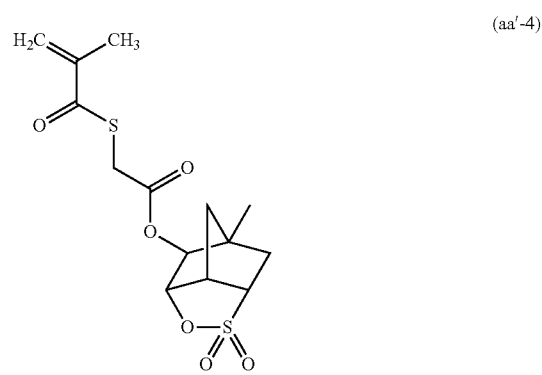

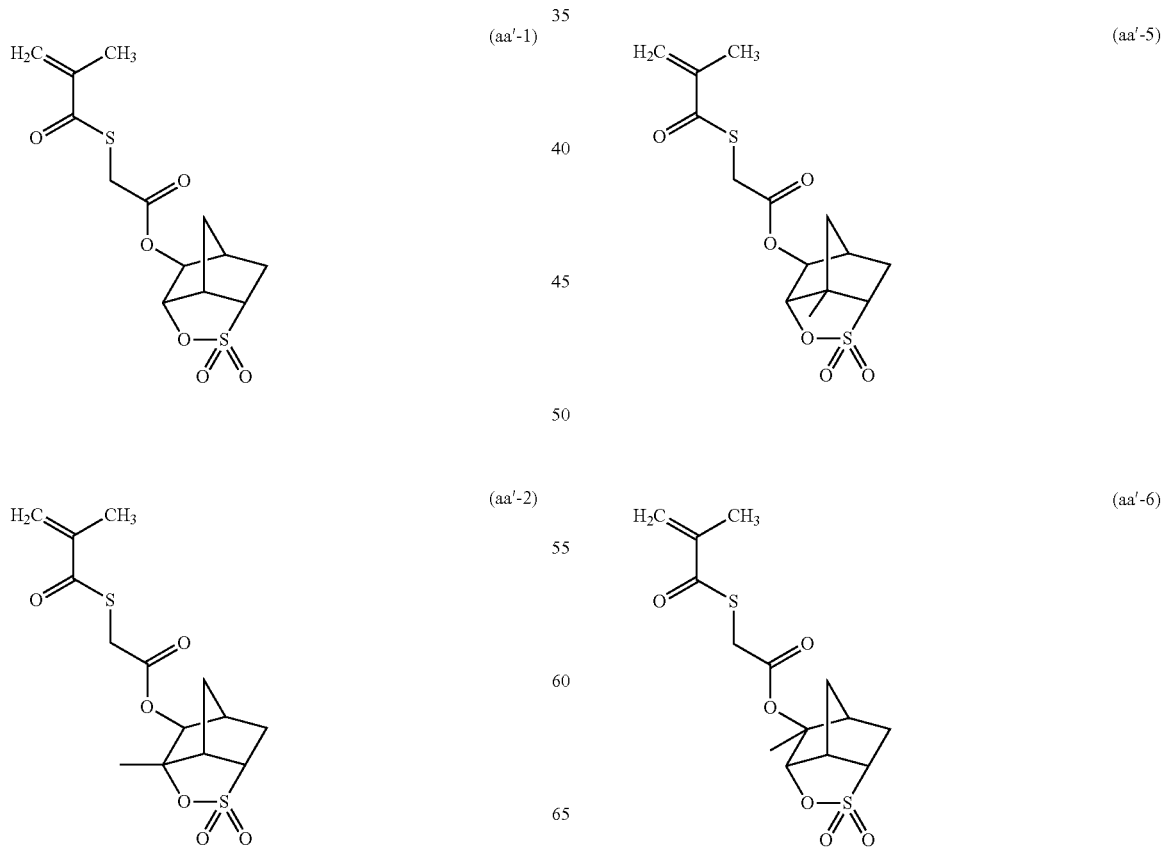

(aa'-7)
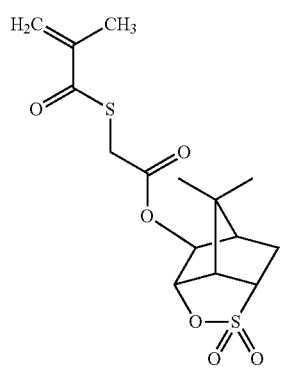
(aa'-8)
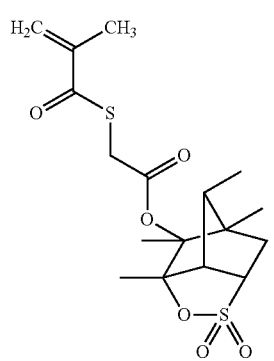
(aa'-9)
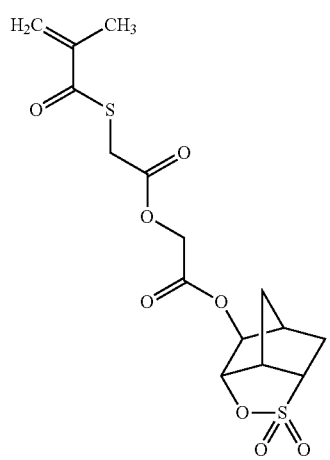
(aa'-10)
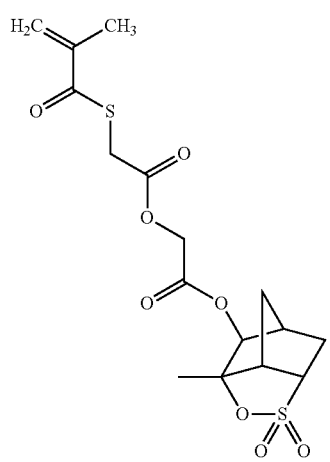
(aa'-11)
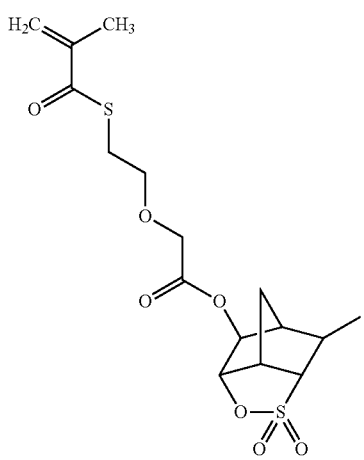
(aa'-12)
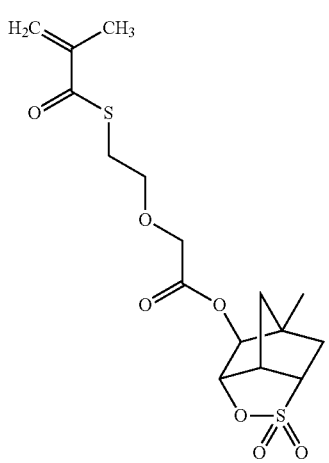
(aa'-13)
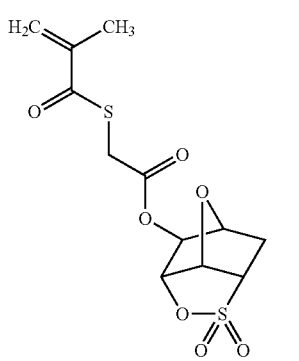
(aa'-14)
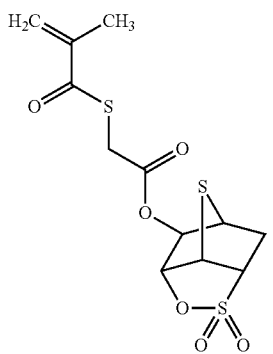

(aa'-15)
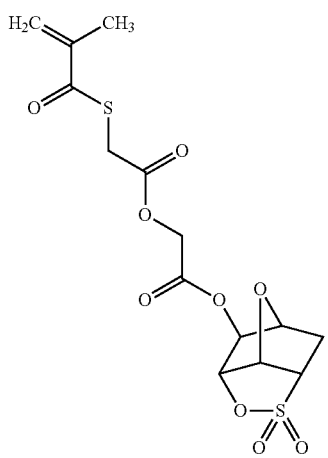
(aa'-18)
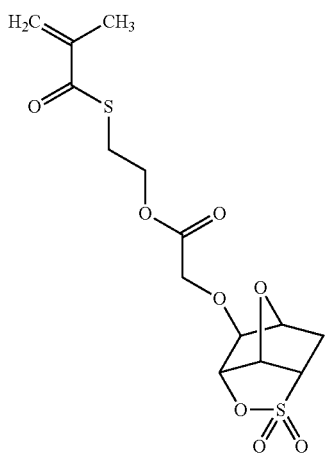
(aa'-16)
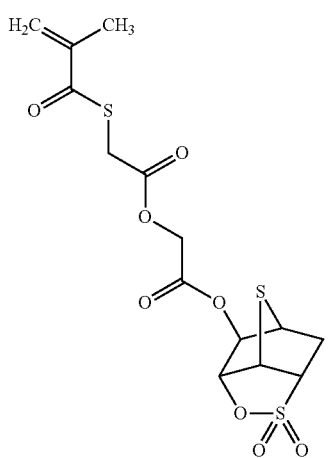
(aa'-19)
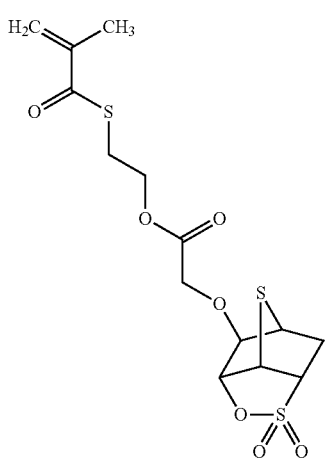
(aa'-17)
(aa'-20)
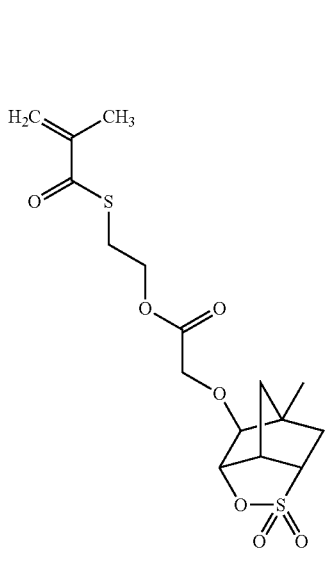

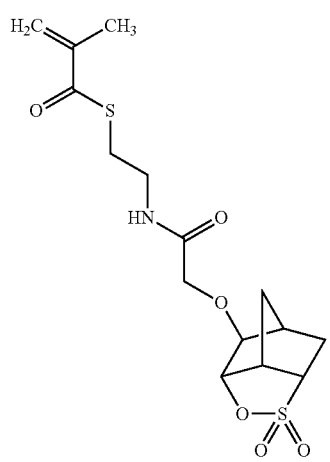
(aa'-21)
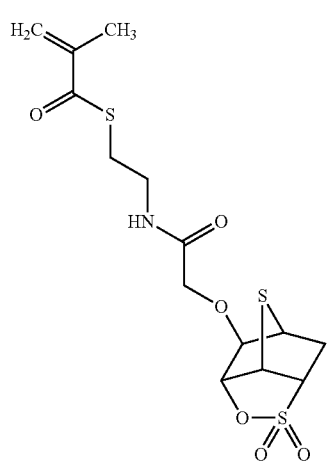
(aa'-22)
(aa'-23)
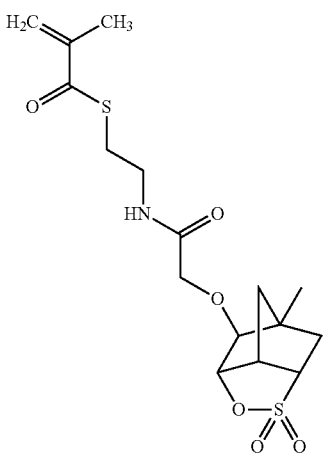
(aa'-24)
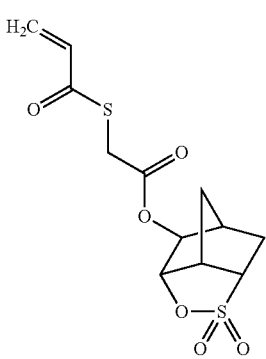
(aa'-25)
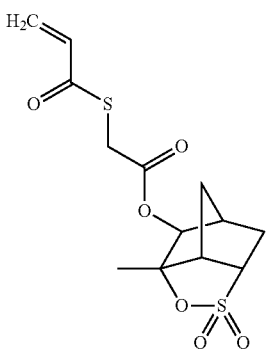
(aa'-26)
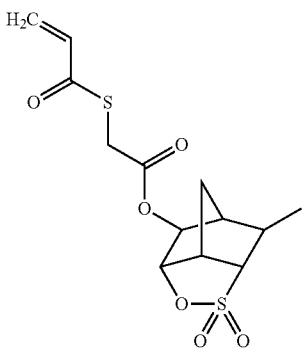
(aa'-27)

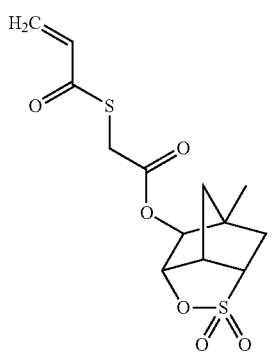
(aa'-28)
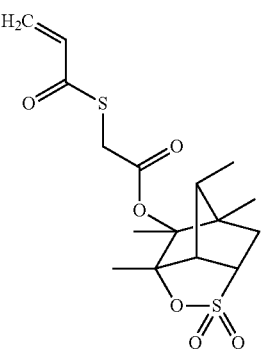
(aa'-32)
(aa'-29)
(aa'-33)
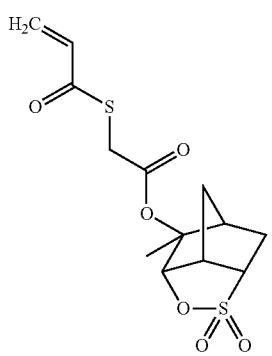
(aa'-30)
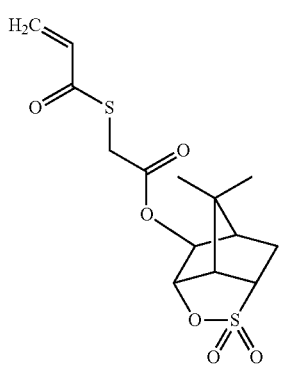
(aa'-31)
(aa'-34)

(aa'-35)
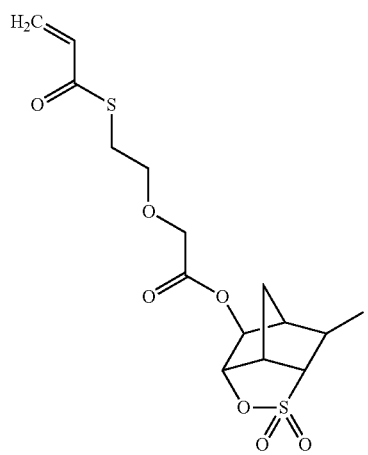
(aa'-36)
(aa'-37)
(aa'-38)
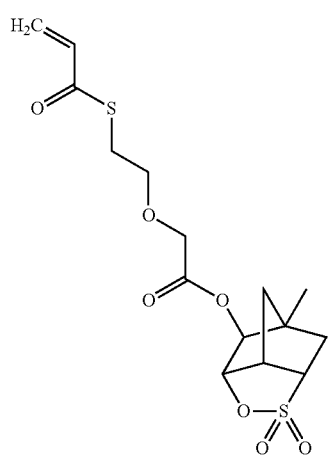
(aa'-39)
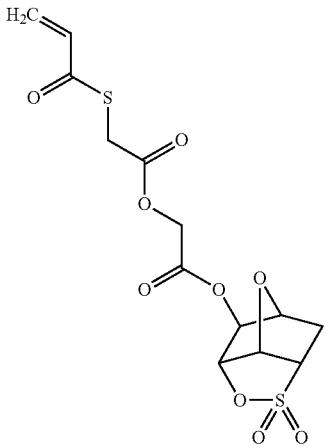
(aa'-40)
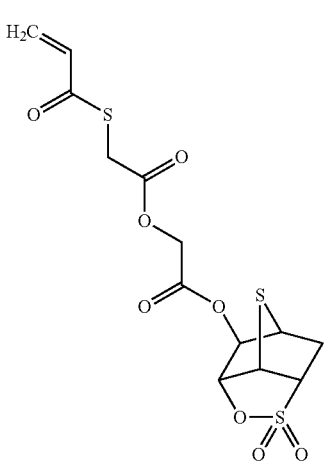
(aa'-41)
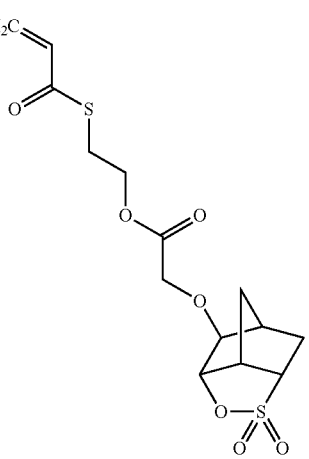

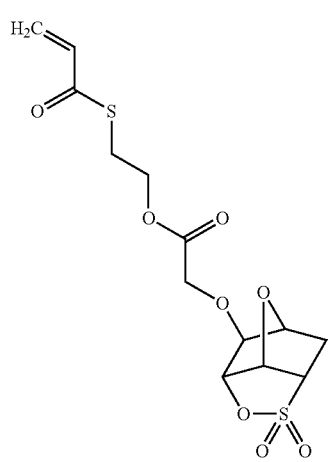
(aa'-42)
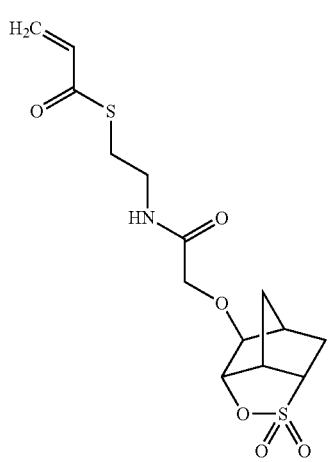
(aa'-45)
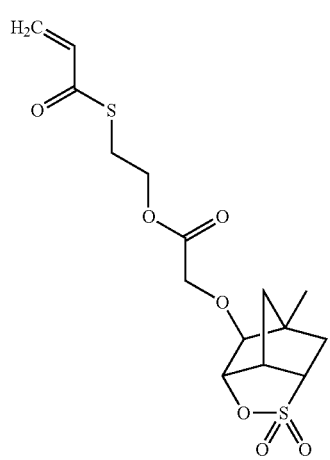
(aa'-43)
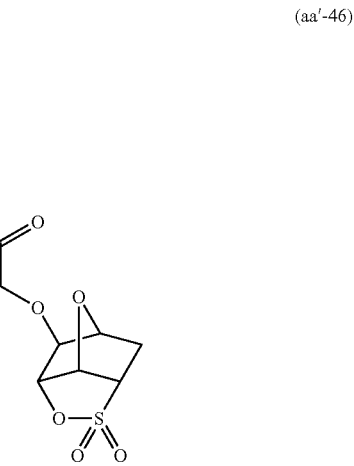
(aa'-46)
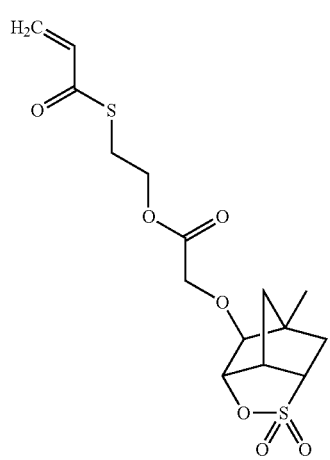
(aa'-44)
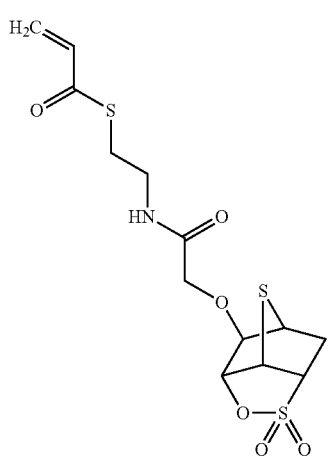
(aa'-47)

-continued (aa'-48)
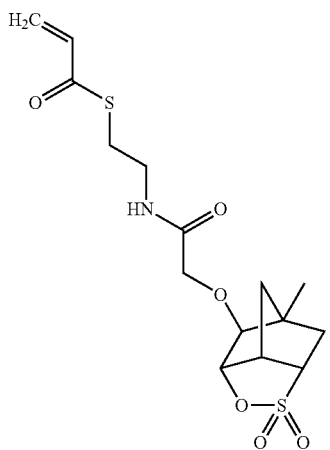

The content of the structural unit represented by the formula (aa) in RESIN (A) is preferably 2 to 40% by mole, more preferably 3 to 35% by mole and especially preferably 5 to 30% by mole based on 100% by mole of all the structural units of RESIN (A).

RESIN (A) is preferably a resin having an acid-labile group and being insoluble or poorly soluble in an aqueous alkali solution, and the resin is one capable of being soluble in an aqueous alkali solution by the action of an acid.

In the photoresist composition of the present invention, an acid is generated from the acid generator contained therein by exposure. The acid catalytically acts against the acid-labile group in the resin to cleave the acid-labile group, and the resin becomes one being soluble in an aqueous alkali solution.

When RESIN (A) is a resin becoming soluble in an aqueous alkali solution by the action of an acid, the resin can be produced by polymerizing the compound (aa') with a monomer having an acid-labile group. Two kinds of the monomer having an acid-labile group can be used in combination. In this specification, "an acid-labile group" means a group capable of being eliminated by the action of an acid.

Examples of the acid-labile group include a group represented by the formula (1):

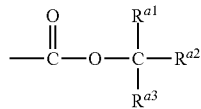
(1)

wherein $R^{a1}$, $R^{a2}$ and $R^{a3}$ independently each represent a C1-C8 aliphatic hydrocarbon group, and $R^{a1}$ and $R^{a2}$ can be bonded each other to form a C3-C20 ring together with a carbon atom to which $R^{a1}$ and $R^{a2}$ are bonded, and one or more —CH$_2$— in the aliphatic hydrocarbon group and the ring can be replaced by —O—, —S— or —CO—.

The group represented by the formula (1) has a structure wherein a tertiary carbon atom is bonded to —O—.

"Aliphatic hydrocarbon group" represented by $R^{a1}$, $R^{a2}$ and $R^{a3}$ contains a chain aliphatic hydrocarbon group, an alicyclic hydrocarbon group and a group formed by combining a chain aliphatic hydrocarbon group with an alicyclic hydrocarbon group.

Examples of the C1-C8 aliphatic hydrocarbon group include a C1-C8 alkyl group and a C3-C8 alicyclic hydrocarbon group. Examples of the C1-C8 alkyl group include a methyl group, an ethyl group, a propyl group, an isopropyl group, a butyl group, a pentyl group, a 1-methylpentyl group, a hexyl group, a 1,4-dimethylhexyl group, a heptyl group, a 1-methylheptyl group and an octyl group. The C3-C8 alicyclic hydrocarbon group may be monocyclic or polycyclic. Examples of the C3-C8 alicyclic hydrocarbon group include groups formed by removing a hydrogen atom from the following cycloalkanes.

(KA-1)

(KA-2)

(KA-3)

(KA-4)

(KA-5)

(KA-6)

When $R^{a1}$ and $R^{a2}$ are bonded each other, they form a C3-C20 ring together with a carbon atom to which they are bonded, examples of the ring include an aliphatic ring and an aromatic ring, and a C3-C12 ring is preferable. When $R^{a1}$ and $R^{a2}$ are bonded each other to form a ring together with a carbon atom to which $R^{a1}$ and $R^{a2}$ are bonded, examples of the group represented by —C($R^{a1}$) ($R^{a2}$) ($R^{a3}$) include the following groups.

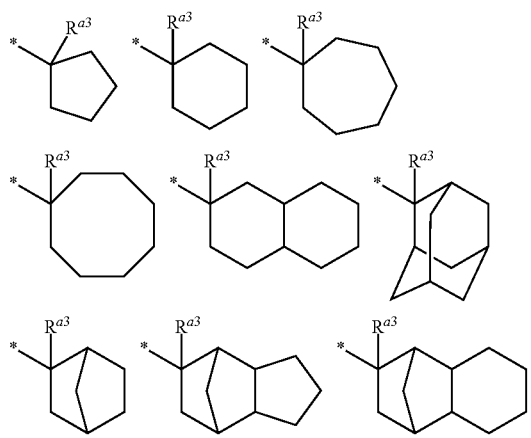

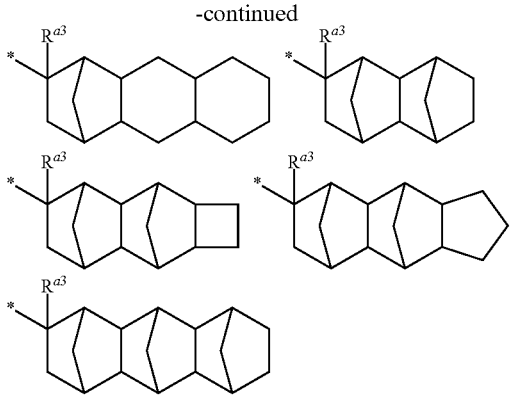

wherein $R^{a3}$ is the same as defined above.

Examples of the acid-labile group include a group represented by the formula (1) wherein $R^{a1}$, $R^{a2}$ and $R^{a3}$ independently each represent an alkyl group such as a tert-butyl group, a group represented by the formula (1) wherein $R^{a1}$ and $R^{a2}$ are bonded each other to form an adamantyl ring and $R^{a3}$ is an alkyl group such as a 2-alkyl-2-adamantyl group, and a group represented by the formula (1) wherein $R^{a1}$ and $R^{a2}$ are alkyl groups and $R^{a3}$ is an adamantyl group such as a 1-(1-adamantyl)-1-alkylalkoxycarbonyl group.

Examples of the acid-labile group include a group represented by the formula (2):

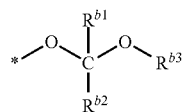

(2)

wherein $R^{b1}$ and $R^{b2}$ independently each represent a hydrogen atom or a C1-C20 hydrocarbon group, and $R^{b3}$ represents a C1-C20 hydrocarbon group, and $R^{b2}$ and $R^{b3}$ can be bonded each other to form a C3-C20 ring together with the carbon atom and the oxygen atom to which they are bonded, and one or more —CH$_2$— in the hydrocarbon group and the ring can be replaced by —O— or —S—, and * represents a binding position.

The group represented by the formula (2) has an acetal structure.

Examples of the hydrocarbon group include an aliphatic hydrocarbon group and an aromatic hydrocarbon group.

"Aliphatic hydrocarbon group" represented by $R^{a1}$, $R^{a2}$ and $R^{a3}$ contains a chain aliphatic hydrocarbon group, an alicyclic hydrocarbon group and a group formed by combining a chain aliphatic hydrocarbon group with an alicyclic hydrocarbon group.

Examples of the chain aliphatic hydrocarbon group include a C1-C20 linear or branched chain alkyl group such as a methyl group, an ethyl group, a propyl group, an isopropyl group, a butyl group, a pentyl group, a hexyl group, a heptyl group, an octyl group, a decyl group, a dodecyl group, a hexadecyl group, a pentadecyl group, a hexadecyl group, a heptadecyl group and an octadecyl group, and groups formed by removing a hydrogen atom from the following cycloalkanes.

 (KA-1)

 (KA-2)

 (KA-3)

 (KA-4)

 (KA-5)

 (KA-6)

 (KA-7)

 (KA-8)

 (KA-9)

 (KA-10)

 (KA-11)

 (KA-12)

 (KA-13)

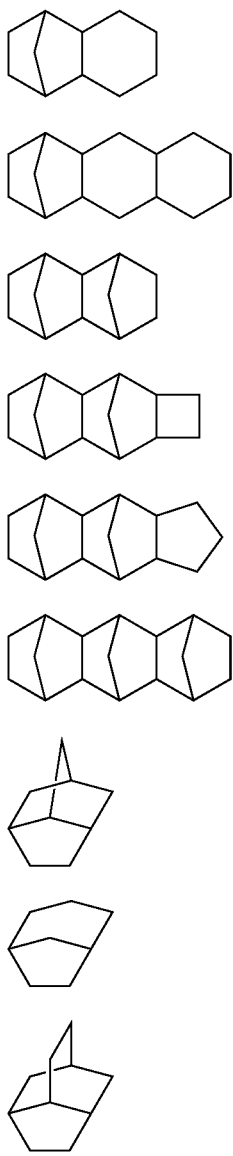

Examples of the aromatic hydrocarbon group include an aryl group such as a phenyl group, a naphthyl group, an anthryl group, a biphenyl group, a phenanthryl group and a fluorenyl group.

It is preferred that at least one of $R^{b1}$ and $R^{b2}$ is a hydrogen atom.

Examples of the group represented by the formula (2) include the following.

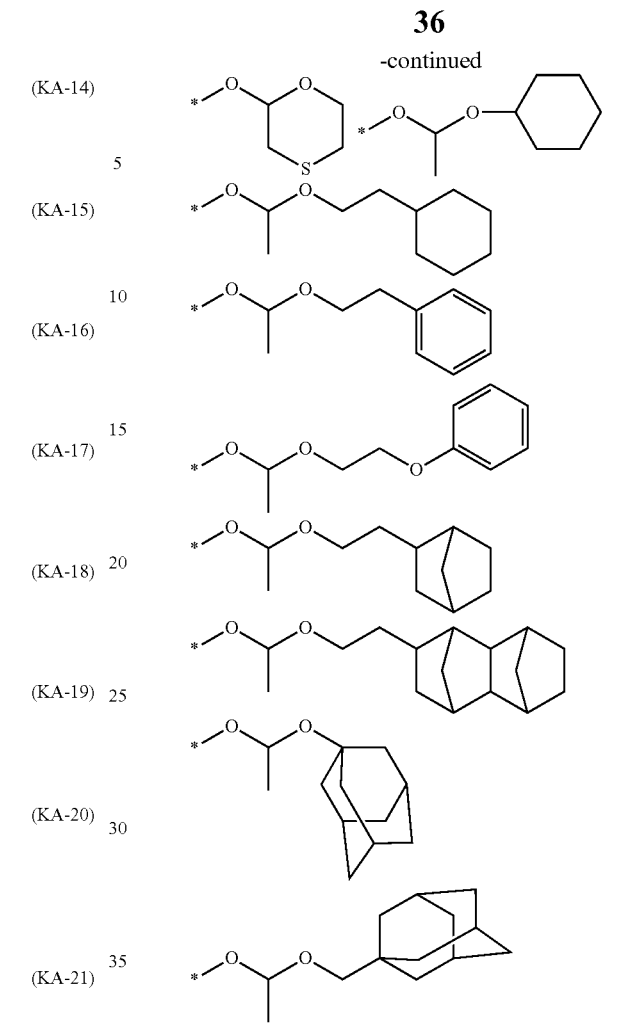

The monomer having an acid-labile group is preferably a monomer having an acid-labile group in its side chain and a carbon-carbon double bond, and is more preferably an acrylate monomer having an acid-labile group in its side chain or a methacryalte monomer having an acid-labile group in its side chain. An acrylate monomer having the group represented by the formula (1) or (2) in its side chain or a methacryalte monomer having the group represented by the formula (1) or (2) in its side chain is especially preferable.

An acrylate monomer having the group represented by the formula (1) in its side chain or a methacryalte monomer having the group represented by the formula (1) in its side chain is preferable, and an acrylate monomer having the group represented by the formula (1) in which $R^{a1}$ and $R^{a2}$ are bonded each other to form a C5-C20 saturated alicycle together with the carbon atom to which they are bonded in its side chain or a methacryalte monomer having the group represented by the formula (1) in which $R^{a1}$ and $R^{a2}$ are bonded each other to form a C5-C20 saturated alicycle together with the carbon atom to which they are bonded in its side chain is more preferable. When the photoresist composition contains a resin derived from a monomer having a bulky structure such as a saturated alicyclic hydrocarbon group, the photoresist composition having excellent resolution tends to be obtained.

Preferable examples of the structural unit derived from the monomer having an acid-labile group include the structural units represented by the formulae (a1-1) and (a1-2):

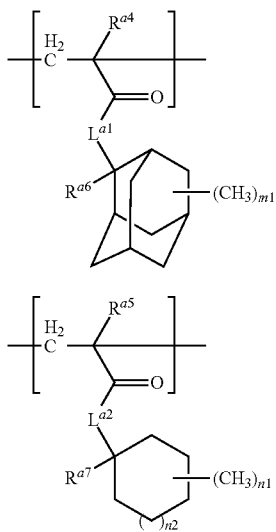

(a1-1)

(a1-2)

wherein $R^{a4}$ and $R^{a5}$ each independently represents a hydrogen atom or a methyl group, $R^{a6}$ and $R^{a7}$ each independently represents a C1-C10 aliphatic hydrocarbon group, $L^{a1}$ and $L^{a2}$ each independently represents *—O— or *—O—$(CH_2)_{k1}$—CO—O— in which * represents a binding position to —CO—, and k1 represents an integer of 1 to 7, and m1 represents an integer of 0 to 14, n1 represents an integer of 0 to 10, and n2 represents 0 or 5.

$L^{a1}$ is preferably *—O— or *—O—$(CH_2)_{f1}$—CO—O— in which * represents a binding position to —CO—, and f1 represents an integer of 1 to 4, and is more preferably *—O— or *—O—$CH_2$—CO—O—, and is especially preferably *—O—$L^{a2}$ is preferably *—O— or *—O—$(CH_2)_{f1}$—CO—O— in which * represents a binding position to —CO—, and f1 is the same as defined above, and is more preferably *—O— or *—O—$CH_2$—CO—O—, and is especially preferably *—O—.

$R^{a4}$ and $R^{a5}$ are preferably methyl groups.

The aliphatic hydrocarbon group represented by $R^{a6}$ and $R^{a7}$ is preferably C1-C8 alkyl group or C3-C10 alicyclic hydrocarbon group. It is preferred that $R^{a6}$ and $R^{a7}$ independently each represent C1-C8 alkyl group or C3-C8 alicyclic hydrocarbon group, and it is more preferred that $R^{a6}$ and $R^{a7}$ independently each represent C1-C6 alkyl group or C3-C6 alicyclic hydrocarbon group. Examples of the aliphatic hydrocarbon group include a methyl group, an ethyl group, a propyl group, an isopropyl group, a tert-butyl group, a 2,2-dimethylethyl group, a propyl group, a 1-methylpropyl group, a 2,2-dimethylpropyl group, a 1-ethylpropyl group, a butyl group, a 1-methylbutyl group, a 2-methylbutyl group, a 3-methylbutyl group, a 1-propylbutyl group, a pentyl group, a 1-methylpentyl group, a hexyl group, a 1,4-dimethylhexyl group, a heptyl group, a 1-methylheptyl group and an octyl group. Examples of the alicyclic hydrocarbon group include a cycloheptyl group, a methylcycloheptyl group, a cyclohexyl group, a methylcyclohexyl group, a dimethylcyclohexyl group, a norbornyl group and a methylnorbornyl group.

In the formula (a1-1), m1 is preferably an integer of 0 to 3, and is more preferably 0 or 1. In the formula (a1-2), n1 is preferably an integer of 0 to 3, and is more preferably 0 or 1, and n2 is preferably 0, 1 or 2, and more preferably 0 or 1. It is preferred that k1 is an integer of 1 to 4, and it is more preferred that k1 is 1.

Examples of the structural unit represented by the formula a (a1-1) include the structural units represented by the formula e (a1-1-1) to (a1-1-38).

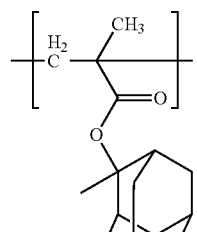

(a1-1-1)

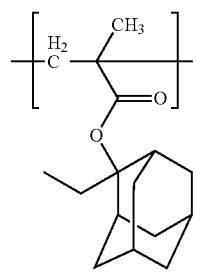

(a1-1-2)

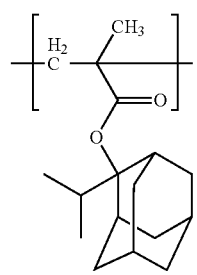

(a1-1-3)

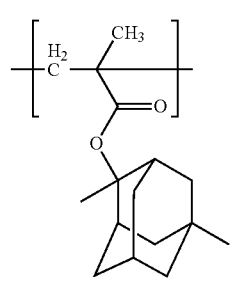

(a1-1-4)

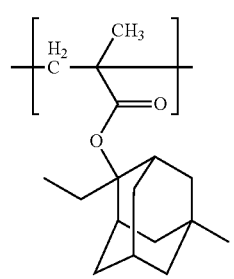

(a1-1-5)

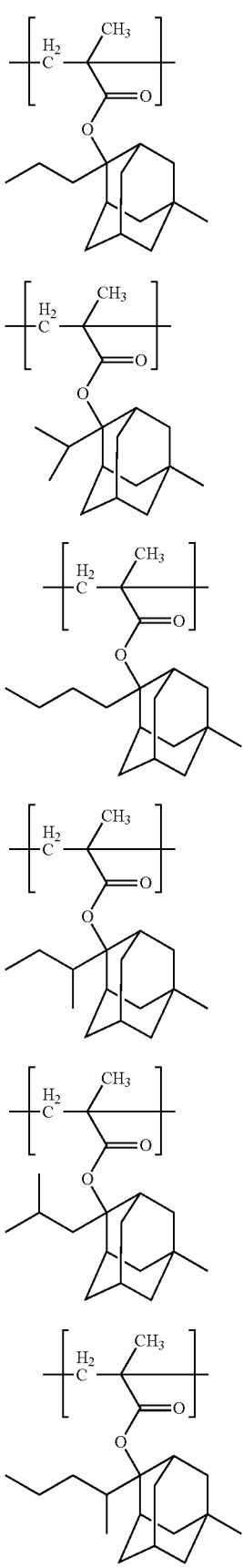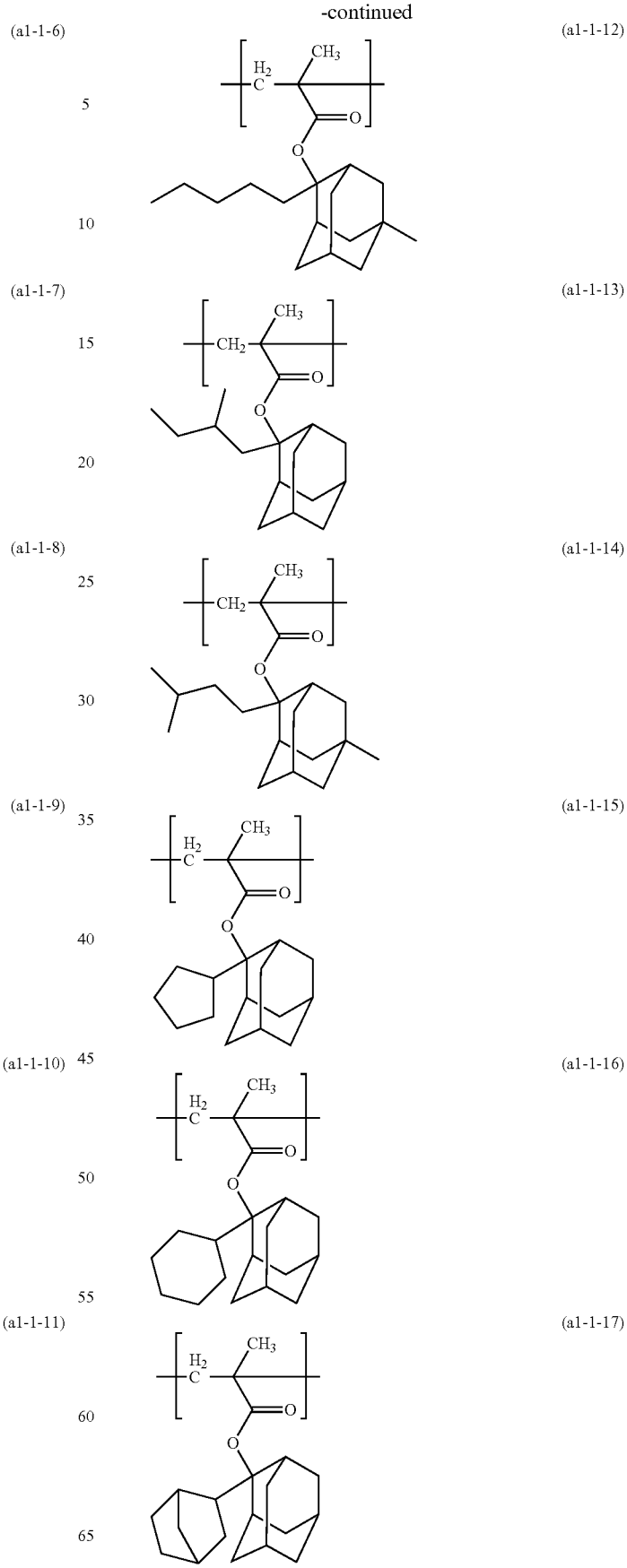

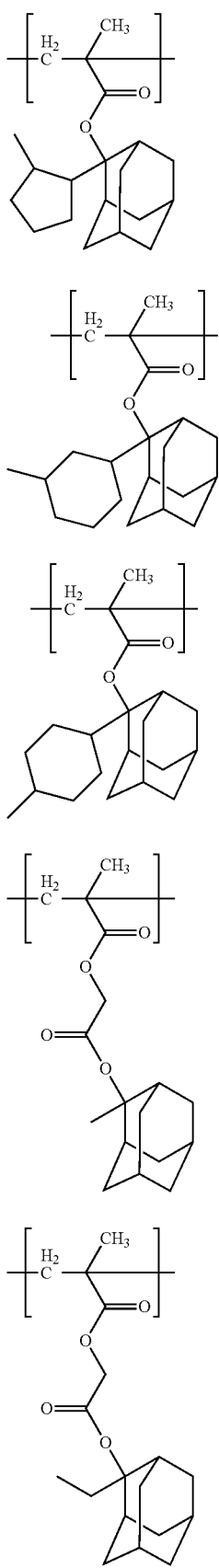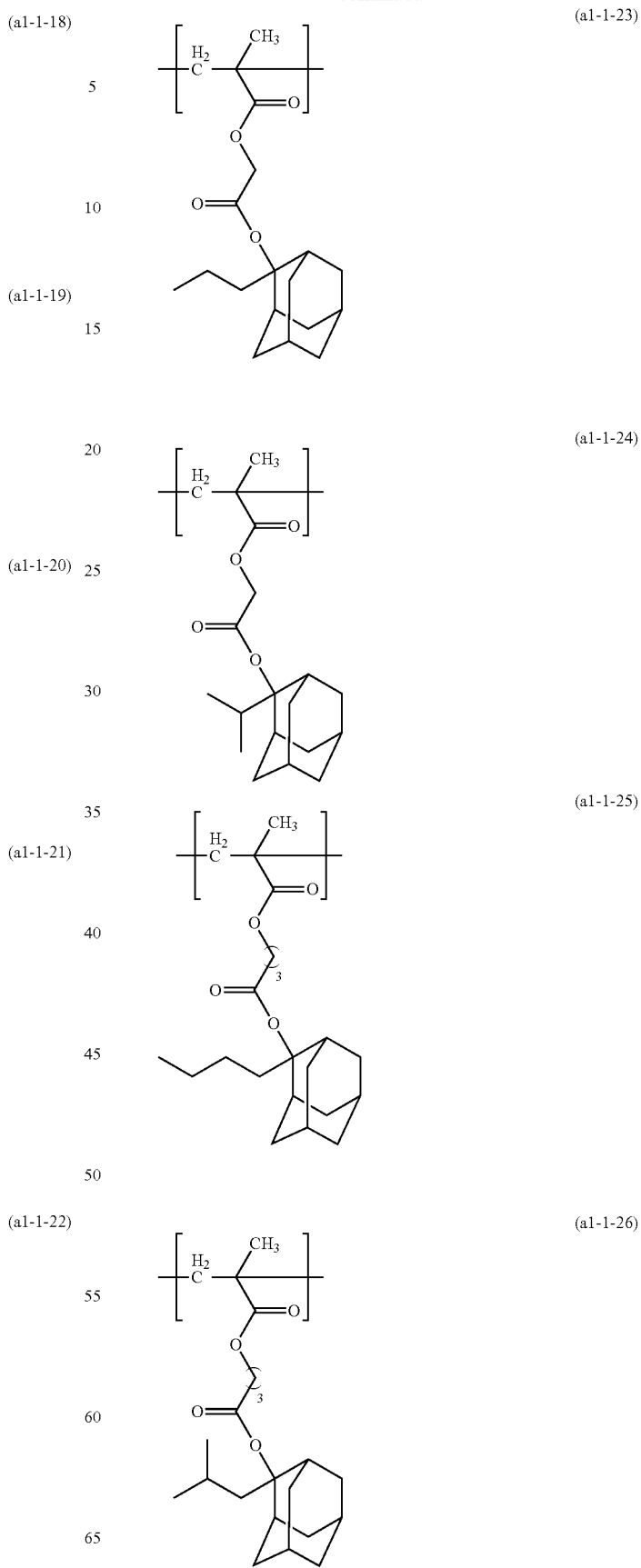

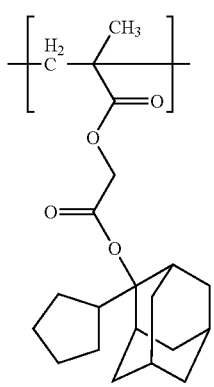 (a1-1-27)
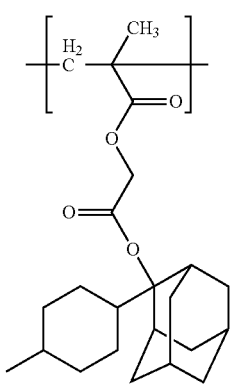 (a1-1-31)
(a1-1-28)
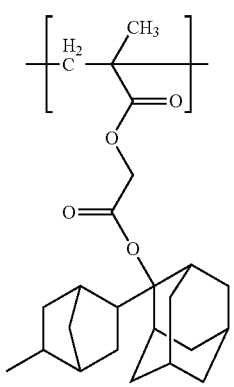 (a1-1-32)
(a1-1-29)
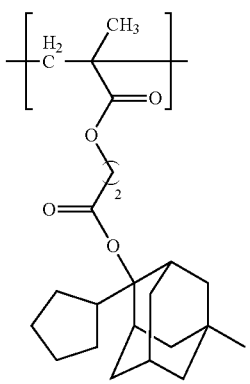 (a1-1-33)
(a1-1-30)
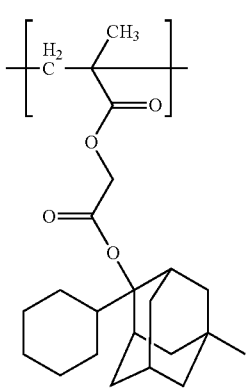 (a1-1-34)

(a1-1-35)
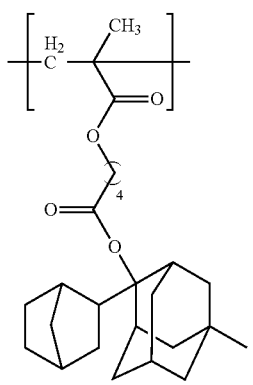

(a1-1-36)
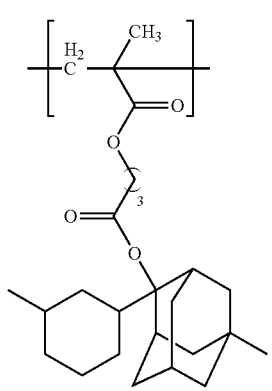

(a1-1-37)
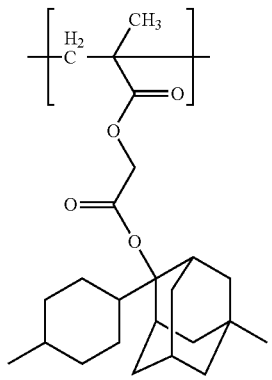

(a1-1-38)
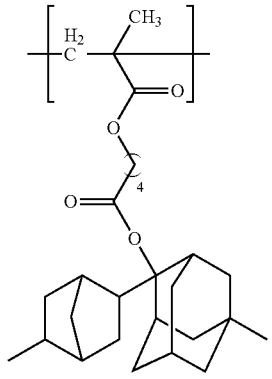

Examples of the structural unit represented by the formula (a1-1) include the structural units represented by the formulae (a1-1-1) to (a1-1-38) wherein the following partial structure M1 is replaced by the following partial structure A2.

(partial structure M1)
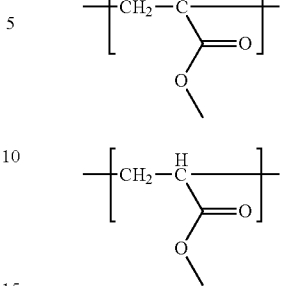

(partial structure A2)
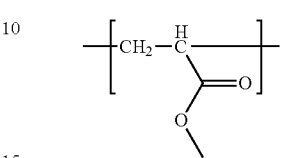

Among them, preferred are the structural units represented by the formulae (a1-1-1), (a1-1-2) and (a1-1-3) and these structures wherein the above-mentioned partial structure M1 is replaced by the above-mentioned partial structure A2, and more preferred are the structural units represented by the formulae (a1-1-1), (a1-1-2) and (a1-1-3), and especially preferred are the structural units represented by the formulae (a1-1-1) and (a1-1-2). These preferable structural units can be derived from 2-methyl-2-adamantyl acrylate, 2-methyl-2-adamantyl methacrylate, 2-ethyl-2-adamantyl acrylate, 2-ethyl-2-adamantyl methacrylate, 2-isopropyl-2-adamantyl acrylate and 2-isopropyl-2-adamantyl methacrylate.

Examples of the structural unit represented by the formula (a1-2) include the structural units represented by the formulae (a1-2-1) to (a1-2-12).

(a1-2-1)
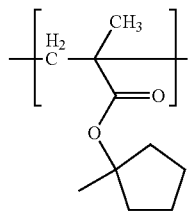

(a1-2-2)
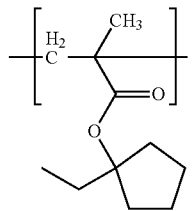

(a1-2-3)
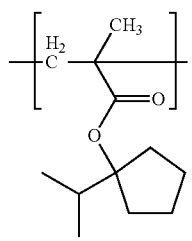

(a1-2-4) 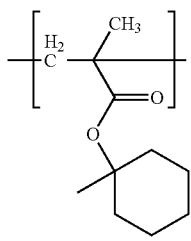

(a1-2-5) 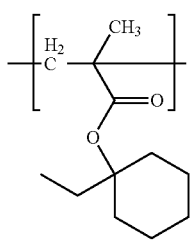

(a1-2-6) 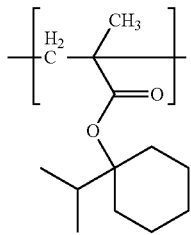

(a1-2-7) 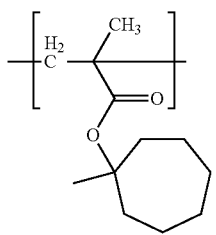

(a1-2-8) 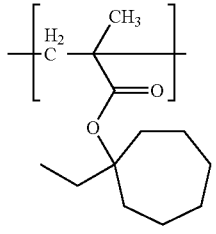

(a1-2-9) 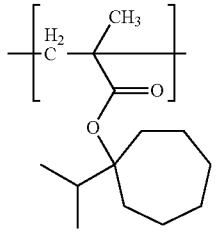

(a1-2-10) 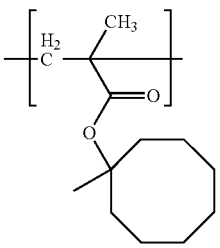

(a1-2-11) 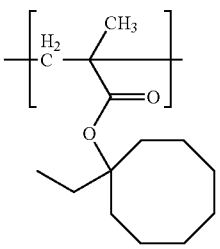

(a1-2-12) 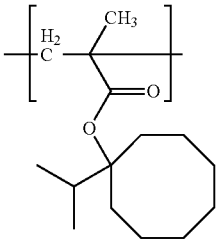

Examples of the structural unit represented by the formula (a1-2) include the structural units represented by the formulae (a1-2-1) to (a1-2-12) wherein the above-mentioned partial structure M1 is replaced by the above-mentioned partial structure A2.

Among them, preferred are the structural units represented by the formulae (a1-2-1), (a1-2-2), (a1-2-4) and (a1-2-5) and these structures wherein the above-mentioned partial structure M1 is replaced by the above-mentioned partial structure A2, and more preferred are the structural units represented by the formulae (a1-2-4) and (a1-2-5) and these structures wherein the above-mentioned partial structure M1 is replaced by the above-mentioned partial structure A2. These preferable structural units can be derived from 1-ethyl-1-cyclohexyl acrylate, 1-ethyl-1-cyclohexyl methacrylate, and the like.

The content of the structural unit represented by the formula (a1-1) or (a1-2) in RESIN (A) is usually 10 to 95% by mole, preferably 15 to 90% by mole and more preferably 20 to 85% by mole and especially preferably 25 to 60% by mole based on 100% by mole of all the structural units of RESIN (A).

The content of the structural unit represented by the formula (a1-1) or (a1-2) in RESIN (A) can be adjusted by adjusting the amount of the monomer giving the structural unit represented by the formula (a1-1) or (a1-2) based on the total amount of the monomers used for producing RESIN (A). Specifically, the amount of the monomer giving the structural unit represented by the formula (a1-1) or (a1-2) is usually 10 to 95% by mole, preferably 15 to 90% by mole and more preferably 20 to 85% by mole and especially preferably 25 to 60% by mole based on 100% by mole of all the monomers used for producing RESIN (A).

Other examples of the monomer having an acid-labile group include a monomer represented by the formula (a1-3):

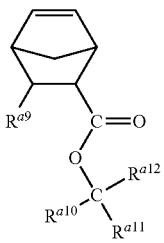

(a1-3)

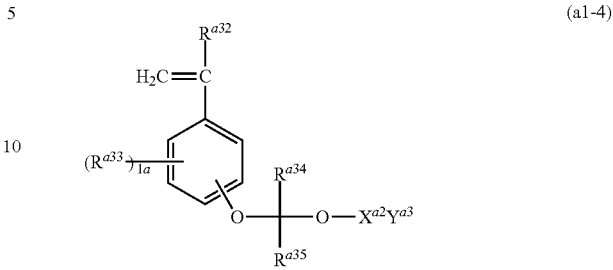

(a1-4)

wherein $R^{a9}$ represents a hydrogen atom, a C1-C3 alkyl group which can have one or more hydroxyl groups (—OH), a carboxyl group (—COOH), a cyano group or a —COOR$^{a13}$ group in which $R^{a13}$ represents a C1-C20 aliphatic hydrocarbon group, and the aliphatic hydrocarbon group can have one or more hydroxyl groups, and one or more —CH$_2$— in the aliphatic hydrocarbon group can be replaced by —O— or —CO—, $R^{a10}$, $R^{a11}$ and $R^{a12}$ each independently represent a C1-C20 aliphatic hydrocarbon group, and $R^{a10}$ and $R^{a11}$ can be bonded each other to form a C3-C20 ring together with the carbon atom to which $R^{a10}$ and $R^{a11}$ are bonded, and the aliphatic hydrocarbon group can have one or more hydroxyl groups, and one or more —CH$_2$— in the aliphatic hydrocarbon group can be replaced by —O— or —CO—.

When RESIN (A) has a structural unit derived from the monomer represented by the formula (a1-3), the photoresist composition having excellent resolution and higher dry-etching resistance tends to be obtained.

Examples of the C1-C3 alkyl group which can have one or more hydroxyl groups include a methyl group, an ethyl group, a propyl group, a hydroxymethyl group and a 2-hydroxyethyl group. Examples of the aliphatic hydrocarbon group represented by $R^{a10}$, $R^{a11}$ and $R^{a12}$ include a chain hydrocarbon group such as an alkyl group and an alicyclic hydrocarbon group and examples thereof include the same as described above. Examples of $R^{a10}$, $R^{a11}$ and $R^{a12}$ include a methyl group, an ethyl group, a cyclohexyl group, a methylcyclohexyl group, a hydroxycyclohexyl group, an oxocyclohexyl group and an adamantyl group.

Examples of the ring formed by bonding $R^{a10}$ and $R^{a11}$ each other together with the carbon atom to which $R^{a10}$ and $R^{a11}$ are bonded include a cyclohexane ring and an adamantane ring.

Examples of $R^{a13}$ include a methyl group, an ethyl group, a propyl group, a 2-oxo-oxolan-3-yl group and a 2-oxo-oxolan-4-yl group.

Examples of the monomer represented by the formula (a1-3) include tert-butyl 5-norbornene-2-carboxylate, 1-cyclohexyl-1-methylethyl 5-norbornene-2-carboxylate, 1-methylcyclohexyl 5-norbornene-2-carboxylate, 2-methyl-2-adamantyl 5-norbornene-2-carboxylate, 2-ethyl-2-adamantyl 5-norbornene-2-carboxylate, 1-(4-methylcyclohexyl)-1-methylethyl 5-norbornene-2-carboxylate, 1-(4-hydroxylcyclohexyl)-1-methylethyl 5-norbornene-2-carboxylate, 1-methyl-1-(4-oxocyclohexyl) ethyl 5-norbornene-2-carboxylate and 1-(1-adamantyl)-1-methylethyl 5-norbornene-2-carboxylate.

When RESIN (A) contains the structural unit derived form the monomer represented by the formula (a1-3), the content of the structural unit derived from the monomer represented by the formula (a1-3) is usually 10 to 95% by mole and preferably 15 to 90% by mole and more preferably 20 to 85% by mole based on total molar of all the structural units of RESIN (A).

Other examples of the compound having an acid-labile group include a monomer represented by the formula (a1-4):

wherein $R^{a32}$ represents a hydrogen atom, a halogen atom, a C1-C6 alkyl group or a C1-C6 halogenated alkyl group, $R^{a33}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, 1a represents an integer of 0 to 4, $R^{a34}$ and $R^{a35}$ each independently represent a hydrogen atom or a C1-C12 hydrocarbon group, $X^{a2}$ represents a single bond or a C1-C17 divalent saturated hydrocarbon group in which one or more —CH$_2$— can be replaced by —O—, —CO—, —S—, —SO$_2$— or —N(R$^c$)— wherein R$^c$ represents a hydrogen atom or a C1-C6 alkyl group, and $Y^{a3}$ represents a C1-C18 hydrocarbon group, and the C1-C17 divalent saturated hydrocarbon group and the C1-C18 hydrocarbon group can have one or more substituents selected from the group consisting of a halogen atom, a hydroxyl group, a C1-C6 alkyl group, a C1-C6 alkoxy group, a C2-C4 acyl group and a C2-C4 acyloxy group.

Examples of the halogen atom include a fluorine atom, a chlorine atom, a bromine atom and an iodine atom.

Examples of the C1-C6 alkyl group include the same as described above, and a C1-C4 alkyl group is preferable and a C1-C2 alkyl group is more preferable and a methyl group is especially preferable.

Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group, a perfluorohexyl group, a perchloromethyl group, a perbromomethyl group and a periodomethyl group.

Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable.

Examples of the C2-C4 acyl group include an acetyl group, a propionyl group and a butyryl group, and examples of the C2-C4 acyloxy group include an acetyloxy group, a propionyloxy group and a butyryloxy group.

Examples of the hydrocarbon group include the chain aliphatic hydrocarbon group described above, the alicyclic hydrocarbon group described above, and the groups formed by combining these groups such as 2-alkyl-2-adamantyl group and 1-(1-adamantyl)-1-alkyl group, and the aromatic hydrocarbon group.

Preferable examples of the hydrocarbon group represented by $R^{a34}$ and $R^{a35}$ include an isopropyl group, a butyl group, a sec-butyl group, a tert-butyl group, a pentyl group, a hexyl group, an octyl group, a 2-ethylhexyl group, a cyclohexyl group, an adamantyl group, a 2-alkyl-2-adamantyl group, a 1-(1-adamantyl)-1-alkyl group and an isobornyl group.

Preferable examples of the substituents in the C1-C17 divalent saturated hydrocarbon group and the C1-C18 hydrocarbon group is a hydroxyl group.

Examples of the C1-C17 divalent aliphatic hydrocarbon group include a C1-C17 alkanediyl group such as a methylene group, an ethylene group, a propane-1,3-diyl group, a butane-1,4-diyl group, a pentane-1,5-diyl group, a hexane-1,6-diyl group, a heptane-1,7-diyl group, an octane-1,8-diyl group, a nonane-1,9-diyl group, a decane-1,10-diyl group, a undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group.

Examples of the monomer represented by the formula (a1-4) include the followings.

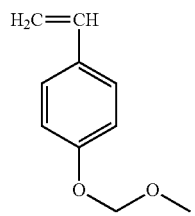
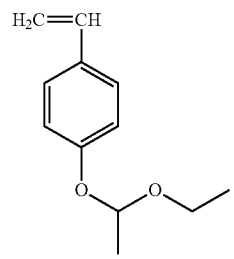
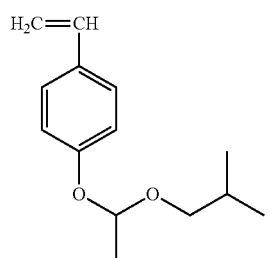
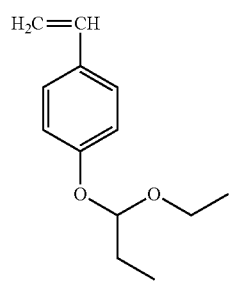
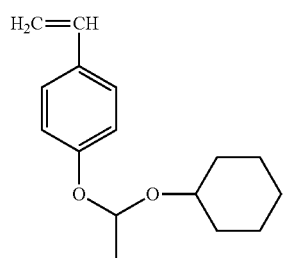
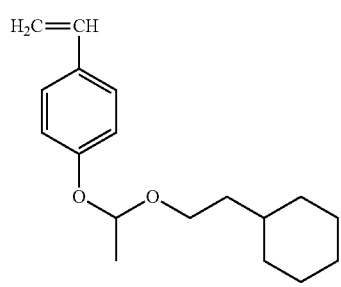

-continued

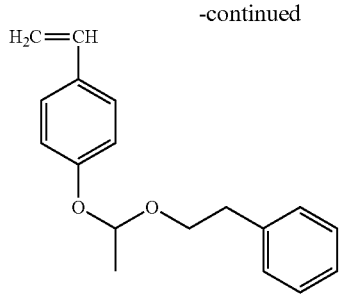
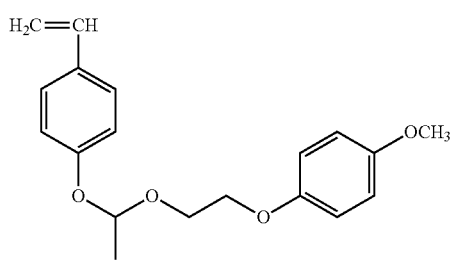
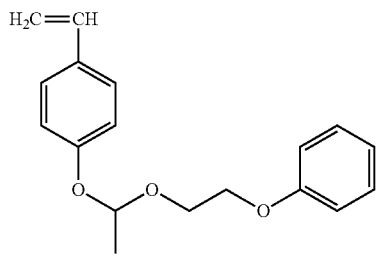
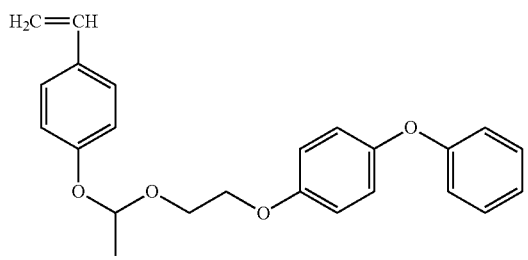
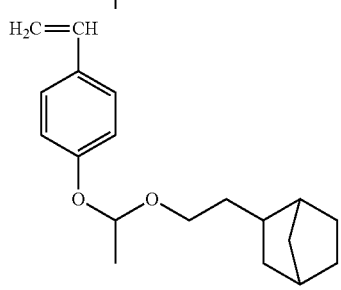
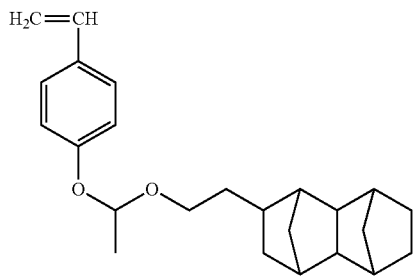

-continued
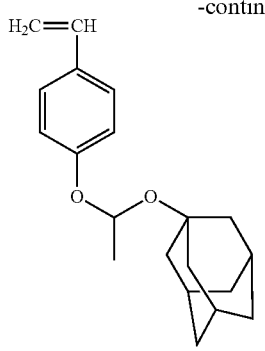
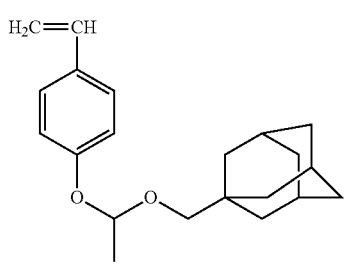
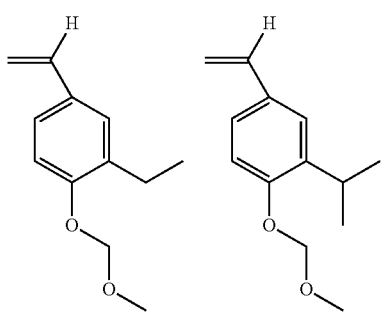
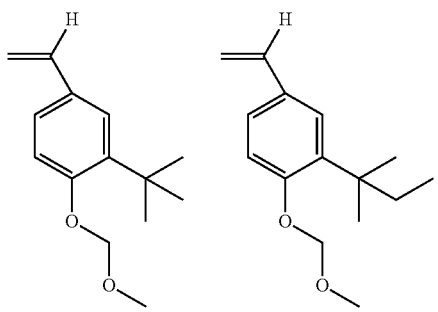
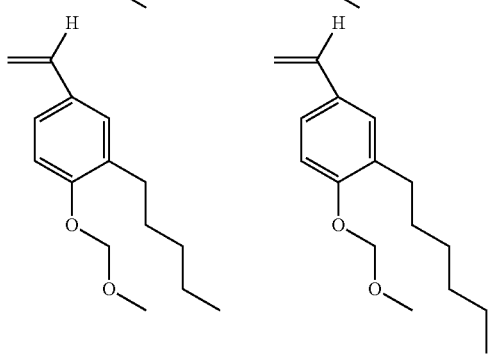
-continued
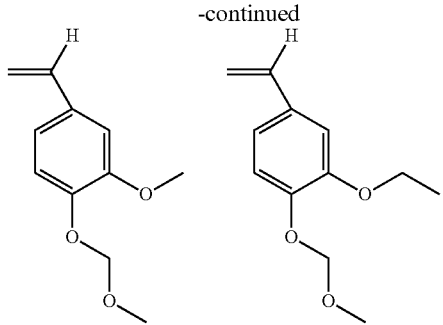
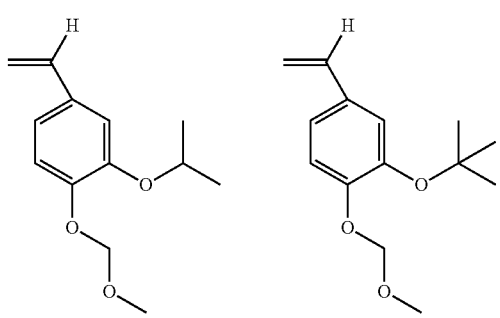
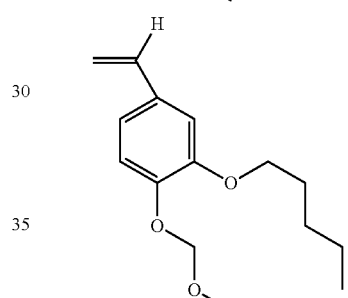
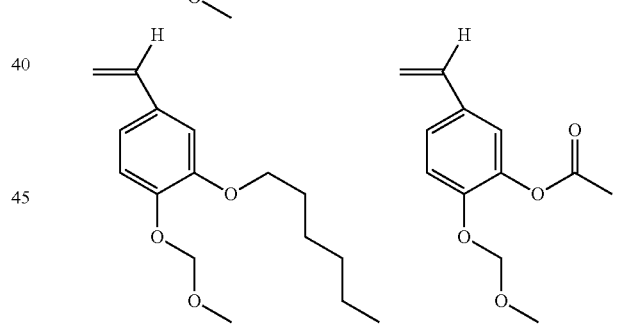
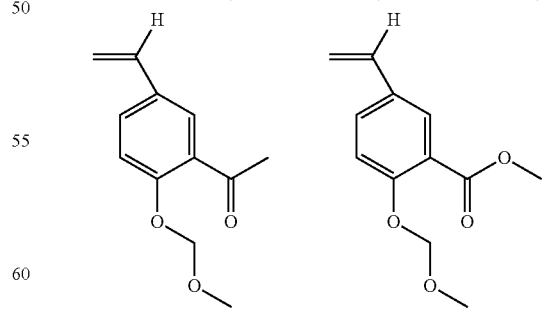
Examples of the monomer represented by the formula (a1-4) include the above-mentioned monomers wherein the following partial structure V' is replaced by the partial structure P'.

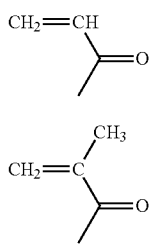 (partial structure V')

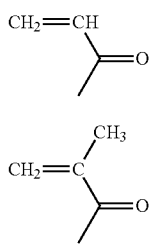 (partial structure P')

When RESIN (A) contains the structural unit derived form the monomer represented by the formula (a1-4), the content of the structural unit derived from the monomer represented by the formula (a1-4) is usually 10 to 95% by mole and preferably 15 to 90% by mole and more preferably 20 to 85% by mole based on total molar of all the structural units of RESIN (A).

Other examples of the monomer having an acid-labile group include a monomer represented by the formula (a1-5):

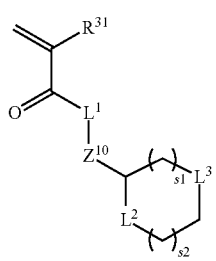 (a1-5)

wherein $R^{31}$ represents a hydrogen atom, a halogen atom, a C1-C4 alkyl group which may be substituted with a halogen atom, $L^1$ represents —O—, —S— or *—O—$(CH_2)_{k2}$—CO—O—, k2 represents an integer of 1 to 7, * represents a binding position to —CO—, $L^2$ and $L^3$ independently each represent —O— or —S—, $Z^{10}$ represents a single bond or a C1-C6 alkandiyl group in which one or more —$CH_2$— may be replaced by —O— or —CO—, s1 and s2 independently each represent an integer of 0 to 4.

$R^{31}$ is preferably a hydrogen atom or a methyl group.

$L^1$ is preferably —O—.

It is preferred that one of $L^2$ and $L^3$ is —O— and the other is —S—.

In the formula (a1-5), s1 is preferably 1 and s2 is preferably 0, 1 or 2.

$Z^{10}$ is preferably a single bond or —$CH_2$—CO—O—.

Examples of the monomer represented by the formula (a1-5) include the following.

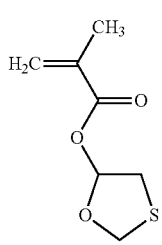 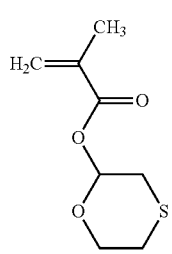 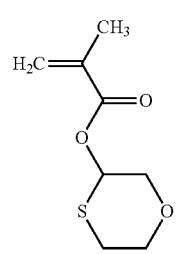

-continued

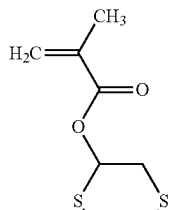 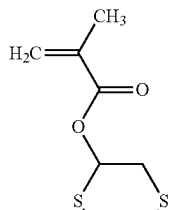 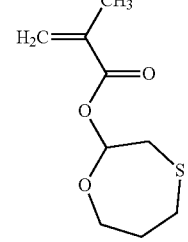

When RESIN (A) contains the structural unit derived form the monomer represented by the formula (a1-5), the content of the structural unit derived from the monomer represented by the formula (a1-5) is usually 10 to 95% by mole and preferably 10 to 90% by mole and more preferably 10 to 85% by mole, and especially preferably 10 to 70% by mole based on total molar of all the structural units of RESIN (A).

RESIN (A) can have two or more kinds of structural units derived from the monomers having an acid-labile group.

RESIN (A) preferably contains the structural unit derived from the monomer having an acid-labile group and a structural unit derived from the monomer having no acid-labile group. RESIN (A) can have two or more kinds of structural units derived from the monomers having no acid-labile group. When RESIN (A) contains the structural unit derived from the monomer having an acid-labile group and the structural unit derived from the monomer having no acid-labile group, the content of the structural unit derived from the monomer having an acid-labile group is usually 10 to 80% by mole and preferably 20 to 60% by mole based on total molar of all the structural units of RESIN (A). The content of the structural unit derived from a monomer having an adamantyl group, especially the monomer represented by the formula (a1-1) in the structural unit derived from the compound having no acid-labile group is preferably 15% by mole or more from the viewpoint of dry-etching resistance of the photoresist composition.

The monomer having no acid-labile group preferably contains one or more hydroxyl groups or a lactone ring. When the resin contains the structural unit derived from the monomer having no acid-labile group and having one or more hydroxyl groups or a lactone ring, a photoresist composition having good resolution and adhesiveness of photoresist to a substrate tends to be obtained.

Examples of the structural unit derived from the monomer having no acid-labile group and having one or more hydroxyl groups include the structural unit represented by the formula (a2-0):

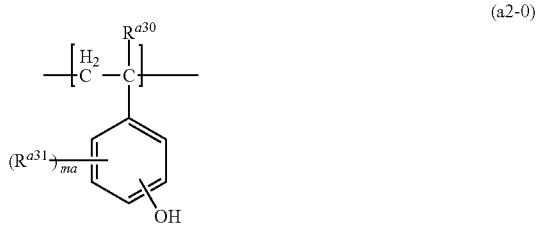

(a2-0)

wherein $R^{a30}$ represents a hydrogen atom, a halogen atom, a C1-C6 alkyl group or a C1-C6 halogenated alkyl group, $R^{a31}$ is independently in each occurrence a halogen atom, a hydroxyl group, a C1-C6 alkyl group, a C1-C6 alkoxy group, a C2-C4 acyl group, a C2-C4 acyloxy group, an acryloyl group or a methacryloyl group, ma represents an integer of 0 to 4, and
the structural unit represented by the formula (a2-1):

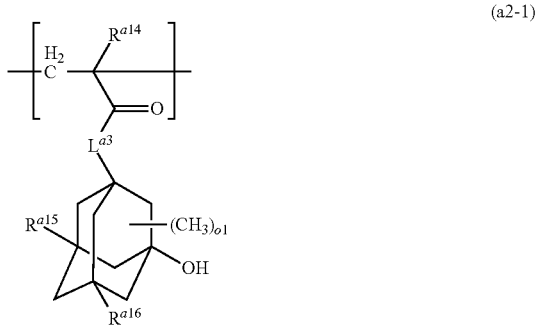

(a2-1)

wherein $R^{a14}$ represents a hydrogen atom or a methyl group, $R^{a15}$ and $R^{a16}$ each independently represent a hydrogen atom, a methyl group or a hydroxyl group, $L^{a3}$ represents *—O— or *—O—$(CH_2)_{k2}$—CO—O— in which * represents a binding position to —CO—, and k2 represents an integer of 1 to 7, and of represents an integer of 0 to 10.

When KrF excimer laser (wavelength: 248 nm) lithography system, or a high energy laser such as electron beam and extreme ultraviolet is used as an exposure system, the resin containing the structural unit derived from the monomer represented by the formula (a2-0) is preferable, and when ArF excimer laser (wavelength: 193 nm) is used as an exposure system, the resin containing the structural unit derived from the monomer represented by the formula (a2-1) is preferable.

In the formula (a2-0), examples of the halogen atom include a fluorine atom, examples of the C1-C6 alkyl group include a methyl group, an ethyl group, a propyl group, an isopropyl group, a butyl group, an isobutyl group, a sec-butyl group, a tert-butyl group, a pentyl group and a hexyl group, and a C1-C4 alkyl group is preferable and a C1-C2 alkyl group is more preferable and a methyl group is especially preferable. Examples of the C1-C6 halogenated alkyl group include a trifluoromethyl group, a pentafluoroethyl group, a heptafluoropropyl group, a heptafluoroisopropyl group, a nonafluorobutyl group, a nonafluoro-sec-butyl group, a nonafluoro-tert-butyl group, a perfluoropentyl group and a perfluorohexyl group. Examples of the C1-C6 alkoxy group include a methoxy group, an ethoxy group, a propoxy group, an isopropoxy group, a butoxy group, an isobutoxy group, a sec-butoxy group, a tert-butoxy group, a pentyloxy group and a hexyloxy group, and a C1-C4 alkoxy group is preferable and a C1-C2 alkoxy group is more preferable and a methoxy group is especially preferable. Examples of the C2-C4 acyl group include an acetyl group, a propionyl group and a butyryl group, and examples of the C2-C4 acyloxy group include an acetyloxy group, a propionyloxy group and a butyryloxy group. In the formula (a2-0), ma is preferably 0, 1 or 2, and is more preferably 0 or 1, and especially preferably 0.

RESIN (A) containing the structural unit derived from the monomer represented by the formula (a2-0) can be produced, for example, by polymerizing a monomer obtained by protecting a hydroxyl group of the monomer represented by the formula (a2-0) with a protecting group such as an acetyl group followed by conducting deprotection of the obtained polymer with an acid or a base.

Examples of the monomer represented by the formula (a2-0) include the followings.

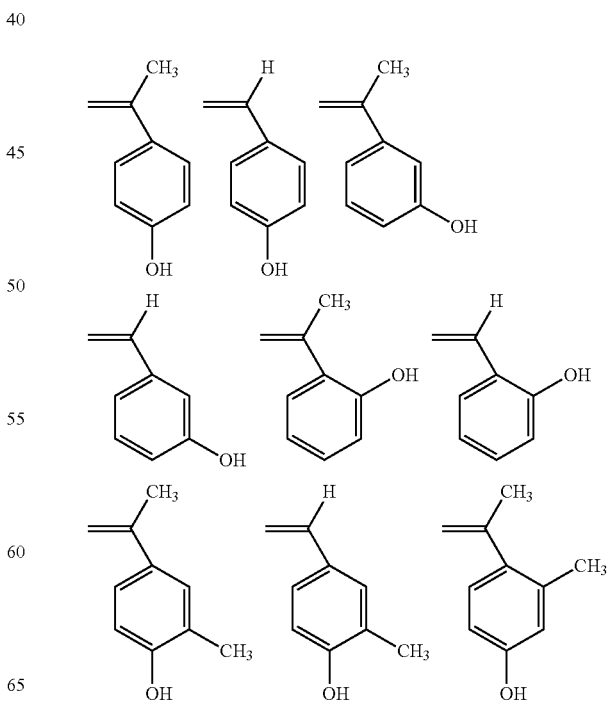

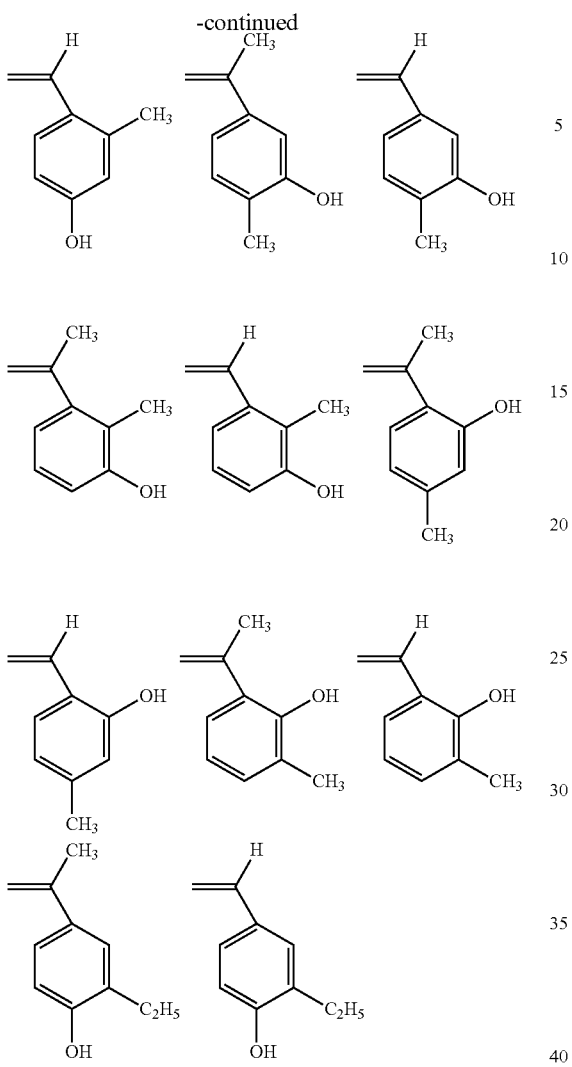

Examples of the monomer represented by the formula (a2-0) include the above-mentioned monomers wherein a methyl group or an ethyl group bonding to a benzene ring is replaced by the other substituent.

Among them, preferred are 4-hydroxystyrene and 4-hydroxy-α-methylstyrene.

When RESIN (A) contains the structural unit represented by the formula (a2-0), the content of the structural unit represented by the formula (a2-0) is usually 5 to 95% by mole and preferably 10 to 80% by mole and more preferably 15 to 80% by mole based on total molar of all the structural units of RESIN (A).

In the formula (a2-1), $R^{a14}$ is preferably a methyl group, $R^{a15}$ is preferably a hydrogen atom, $R^{a16}$ is preferably a hydrogen atom or a hydroxyl group, $L^{a3}$ is preferably *—O— or *—O—$(CH_2)_{f2}$—CO—O— in which * represents a binding position to —CO—, and f2 represents an integer of 1 to 4, more preferably *—O— or *—O—$CH_2$—CO—O—, and especially preferably *—O—, and of is preferably 0, 1, 2 or 3 and is more preferably 0 or 1.

Examples of the structural unit represented by the formula (a2-1) include the structural units represented by the formulae (a2-1-1) to (a2-1-17).

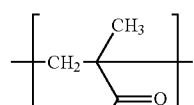

(a2-1-1)

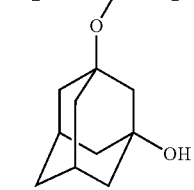

(a2-1-2)

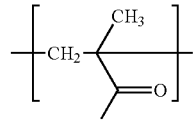

(a2-1-3)

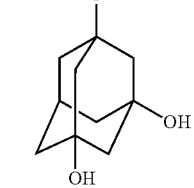

(a2-1-4)

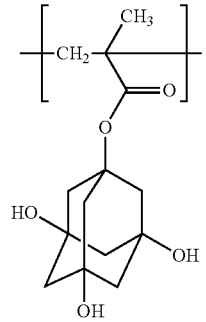

(a2-1-5)

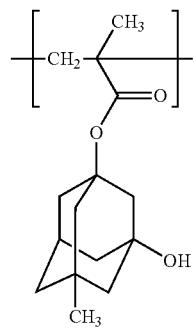

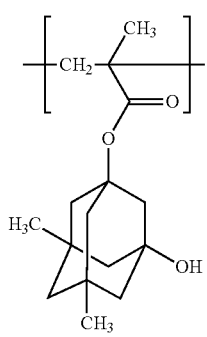 (a2-1-6)
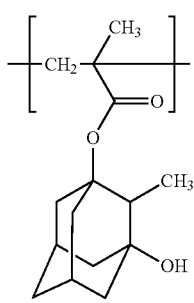 (a2-1-7)
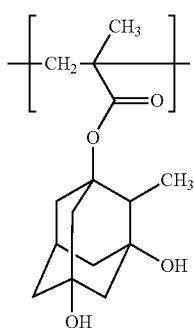 (a2-1-8)
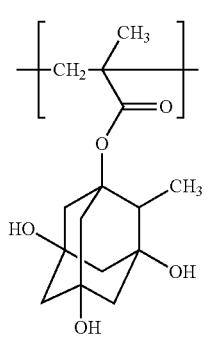 (a2-1-9)
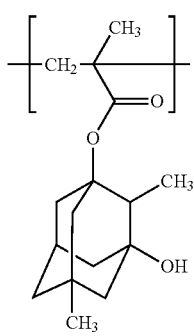 (a2-1-10)
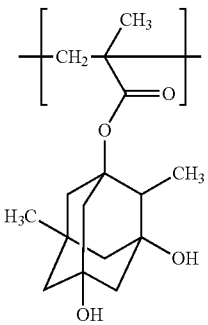 (a2-1-11)
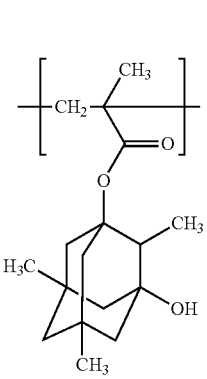 (a2-1-12)
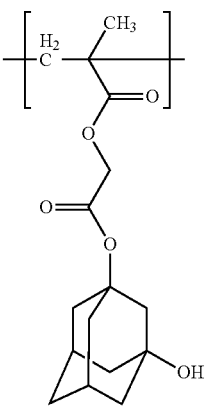 (a2-1-13)
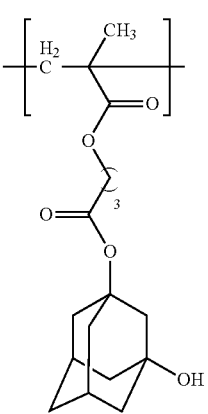 (a2-1-14)

-continued (a2-1-15)
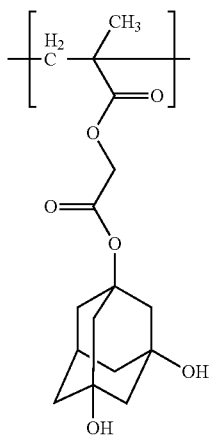

(a2-1-16)
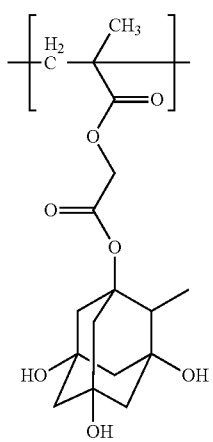

(a2-1-17)
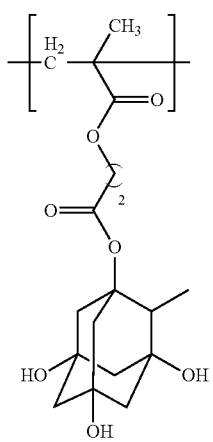

Examples of the structural unit represented by the formula (a2-1) include the structural units represented by the formulae (a2-1-1) to (a2-1-17) wherein the partial structure M1 described above is replaced by the partial structure A2 described above.

Among them, preferred are the structural units represented by the formulae (a2-1-1), (a2-1-2), (a2-1-13) and (a2-1-15) and these structural units wherein the partial structure M1 described above is replaced by the partial structure A2 described above, and more preferred are the structural units represented by the formulae (a2-1-1), (a2-1-2), (a2-1-13) and (a2-1-15).

These structural unit can be derived from 3-hydroxy-1-adamantyl acrylate, 3-hydroxy-1-adamantyl methacrylate, 3,5-dihydroxy-1-adamantyl acrylate, 3,5-dihydroxy-1-adamantyl methacrylate, 1-(3,5-dihydroxy-1-adamantyloxycarbonyl)methyl acrylate, 1-(3,5-dihydroxy-1-adamantyloxycarbonyl)methylmethacrylate, and the like.

When RESIN (A) contains the structural unit represented by the formula (a2-1), the content of the structural unit represented by the formula (a2-1) is usually 3 to 45% by mole based on total molar of all the structural units of RESIN (A), and preferably 5 to 40% by mole, and more preferably 5 to 35% by mole.

Examples of the lactone ring of the monomer having no acid-labile group and a lactone ring include a monocyclic lactone ring such as β-propiolactone ring, γ-butyrolactone ring and γ-valerolactone ring, and a condensed ring formed from a monocyclic lactone ring and the other ring. Among them, preferred are γ-butyrolactone ring and a condensed lactone ring formed from γ-butyrolactone ring and the other ring.

Preferable examples of the structural unit derived from the monomer having no acid-labile group and a lactone ring include the structural units represented by the formulae (a3-1), (a3-2) and (a3-3):

(a3-1)
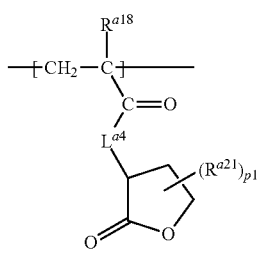

(a3-2)
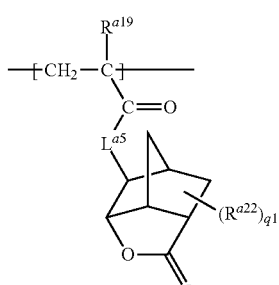

(a3-3)
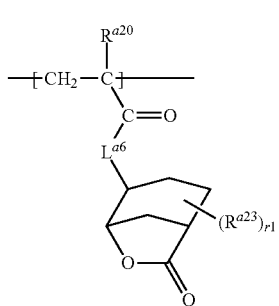

wherein $L^{a4}$, $L^{a5}$ and $L^{a6}$ each independently represent *—O— or *—O—$(CH_2)_{k3}$—CO—O— in which * represents a binding position to —CO— and k3 represents an integer of 1 to 7, $R^{a18}$, $R^{a19}$ and $R^{a20}$ each independently represent a hydrogen atom or a methyl group, $R^{a21}$ represents a C1-C4 aliphatic hydrocarbon group, $R^{a22}$ and $R^{a23}$ are independently in each occurrence a carboxyl group, a cyano group or a C1-C4 aliphatic hydrocarbon group, and p1 represents an integer of 0 to 5, q1 and r1 independently each represent an integer of 0 to 3.

It is preferred that $L^{a4}$, $L^{a5}$ and $L^{a6}$ each independently represent *—O— or *—O—$(CH_2)_{d1}$—CO—O— in which * represents a binding position to —CO— and d1 represents an integer of 1 to 4, and it is more preferred that $L^{a4}$, $L^{a5}$ and $L^{a6}$ are *—O— or *—O—$CH_2$—CO—O—, and it is especially preferred that $L^{a4}$, $L^{a5}$ and $L^{a6}$ are *—O—. $R^{a18}$, $R^{a19}$ and $R^{a20}$ are preferably methyl groups. $R^{a21}$ is preferably a methyl group. It is preferred that $R^{a22}$ and $R^{a23}$ are independently in each occurrence a carboxyl group, a cyano group or a methyl group. It is preferred that p1 is an integer of 0 to 2, and it is more preferred that p1 is 0 or 1. It is preferred that q1 and r1 independently each represent an integer of 0 to 2, and it is more preferred that q1 and r1 independently each represent 0 or 1.

Examples of the structural unit represented by the formula (a3-1) include the structural units represented by the formulae (a3-1-1) to (a3-1-11).

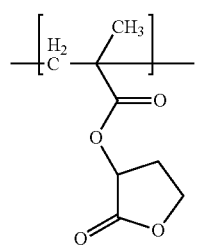
(a3-1-1)

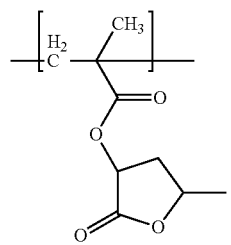
(a3-1-2)

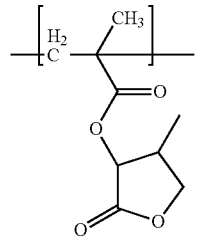
(a3-1-3)

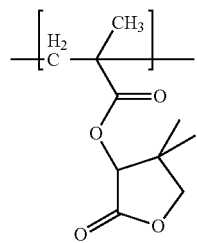
(a3-1-4)

-continued

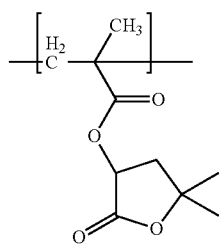
(a3-1-5)

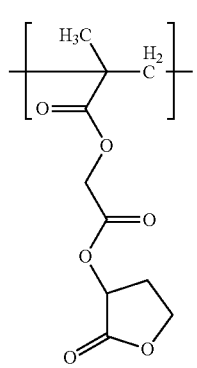
(a3-1-6)

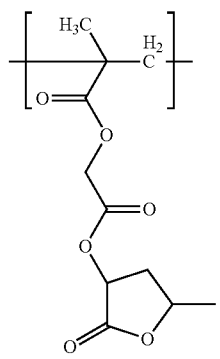
(a3-1-7)

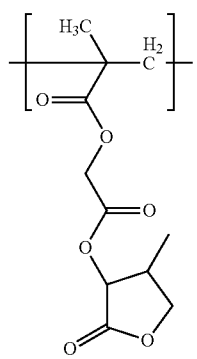
(a3-1-8)

(a3-1-9)
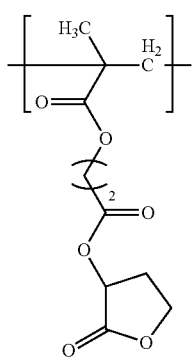
(a3-1-10)
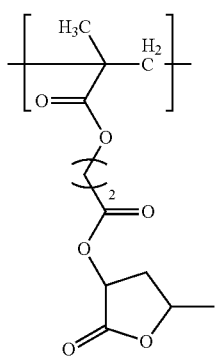
(a3-1-11)
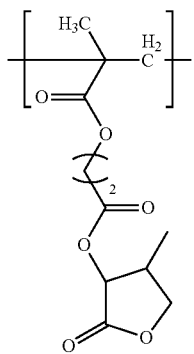
Examples of the structural unit represented by the formula (a3-2) include the structural unit represented by the formula (a3-2-1) to (a3-2-11).
(a3-2-1)
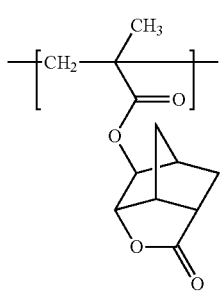
(a3-2-2)
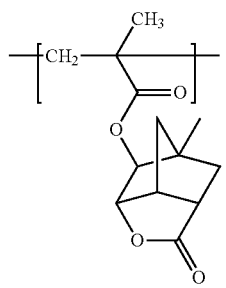
(a3-2-3)
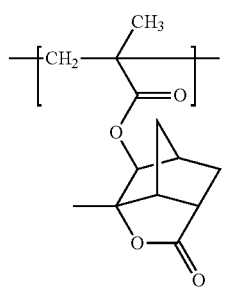
(a3-2-4)
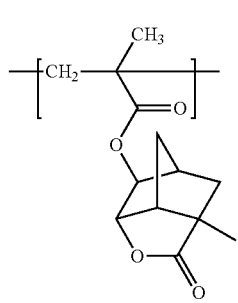
(a3-2-5)
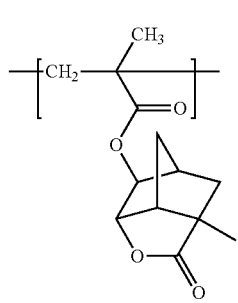
(a3-2-6)
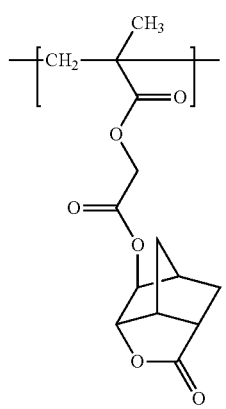

(a3-2-7) 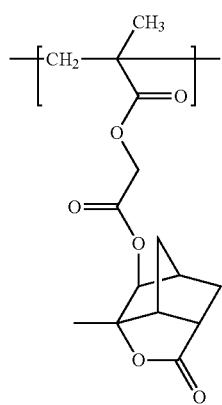
(a3-2-8) 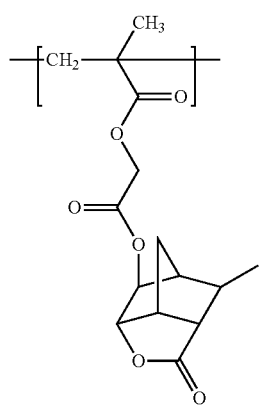
(a3-2-9) 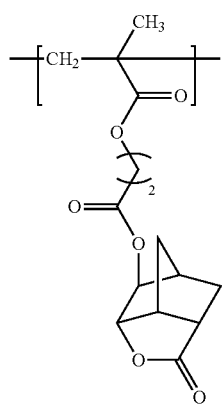
(a3-2-10) 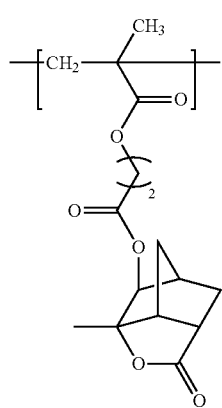
(a3-2-11) 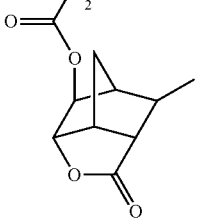
Examples of the structural unit represented by the formula (a3-3) include the structural unit represented by the formula (a3-3-1) to (a3-3-6).
(a3-3-1) 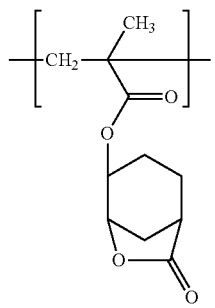
(a3-3-2) 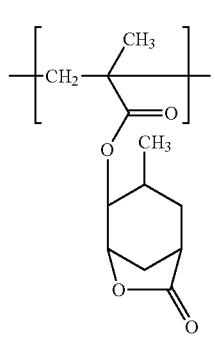
(a3-3-3) 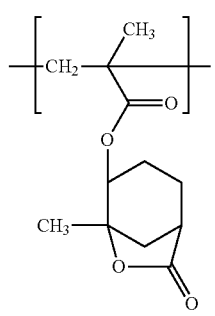

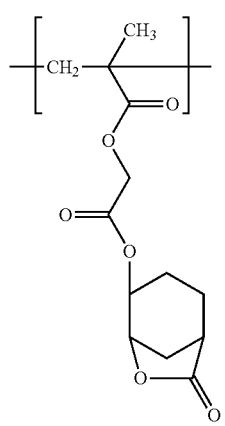
(a3-3-4)

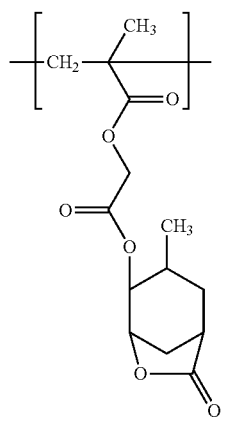
(a3-3-5)

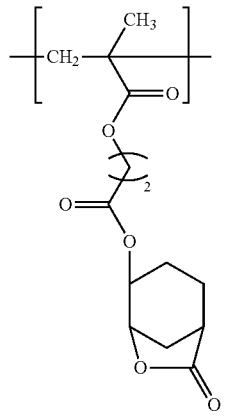
(a3-3-6)

Examples of the structural unit represented by the formula (a3-3) include the structural unit represented by the formula (a3-1-1) to (a3-1-11), (a3-2-1) to (a3-2-11) and (a3-3-1) to (a3-3-6) wherein the partial structure M1 described above is replaced by the partial structure A2 described above.

Among them, preferred are the structural units derived from α-acryloyloxy-γ-butyrolactone, α-methacryloyloxy-γ-butyrolactone, β-acryloyloxy-γ-butyrolactone, β-methacryloyloxy-γ-butyrolactone, α-acryloyloxy-β,β-dimethyl-γ-butyrolactone, α-methacryloyloxy-β,β-dimethyl-γ-butyrolactone, α-acryloyloxy-α-methyl-γ-butyrolactone, α-methacryloyloxy-α-methyl-γ-butyrolactone, β-acryloyloxy-α-methyl-γ-butyrolactone, β-methacryloyloxy-α-methyl-γ-butyrolactone, 5-oxo-4-oxatricyclo[4.2.1.0$^{3,7}$]nonan-2-yl acrylate, 5-oxo-4-oxatricyclo[4.2.1.0$^{3,7}$]nonan-2-yl methacrylate, tetrahydro-2-oxo-3-furyl acrylate, tetrahydro-2-oxo-3-furyl methacrylate, 2-(5-oxo-4-oxatricyclo[4.2.1.0$^{3,7}$]nonan-2-yloxy)-2-oxoethyl acrylate and 2-(5-oxo-4-oxatricyclo[4.2.1.0$^{3,7}$]nonan-2-yloxy)-2-oxoethyl methacrylate.

When RESIN (A) contains the structural unit derived from the monomer having no acid-labile group and having a lactone ring, the content thereof is usually 5 to 70% by mole based on total molar of all the structural units of RESIN (A), and preferably 10 to 65% by mole and more preferably 10 to 60% by mole, still more preferably 15 to 55% by mole and especially preferably 15 to 50% by mole.

When RESIN (A) contains the structural unit represented by the formula (a3-1), (a3-2) or (a3-3), the content thereof is usually 5 to 70% by mole based on total molar of all the structural units of RESIN (A), and preferably 10 to 65% by mole and more preferably 10 to 60% by mole, still more preferably 15 to 55% by mole and especially preferably 15 to 50% by mole.

Examples of the other monomer having no acid-labile group include the monomers represented by the formulae (a4-1), (a4-2) and (a4-3):

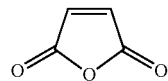
(a4-1)

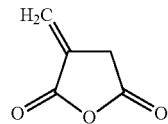
(a4-2)

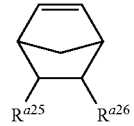
(a4-3)

wherein $R^{a25}$ and $R^{a26}$ each independently represents a hydrogen atom, a C1-C3 alkyl group which can have one or more hydroxyl groups, a carboxyl group, a cyano group or a —COOR$^{a27}$ group in which R$^{a27}$ represents a C1-C18 aliphatic hydrocarbon group, and one or more —CH$_2$— in the C1-C18 aliphatic hydrocarbon group can be replaced by —O— or —CO—, with the proviso that the carbon atom bonded to —O— of —COO— of R$^{a27}$ is not a tertiary carbon atom, or R$^{a25}$ and R$^{a26}$ are bonded together to form a carboxylic anhydride residue represented by —C(=O)—O—C (=O)—.

Examples of the substituent of the C1-C3 alkyl group include a hydroxyl group. Examples of the C1-C3 alkyl group which can have one or more hydroxyl groups include a methyl group, an ethyl group, a propyl group, a hydroxymethyl group and a 2-hydroxyethyl group. The C1-C18 aliphatic hydrocarbon group represented by R$^{a27}$ is preferably a C1-C8 alkyl group or C4-C18 alicyclic hydrocarbon group and is more preferably a C1-C6 alkyl group or a C4-C12 alicyclic hydrocarbon group. Preferable examples of R$^{a27}$ include a methyl group, an ethyl group, a propyl group, a 2-oxo-oxolan-3-yl group and a 2-oxo-oxolan-4-yl group.

Examples of the monomer represented by the formula (a4-3) include 2-norbornene, 2-hydroxy-5-norbornene, 5-norbornene-2-carboxylic acid, methyl 5-norbornene-2-carboxylate, 2-hydroxyethyl 5-norbornene-2-carboxylate, 5-norbornene-2-methanol and 5-norbornene-2,3-dicarboxylic anhydride.

When RESIN (A) contains a structural unit derived from a monomer represented by the formula (a4-1), (a4-2) or (a4-3), the content thereof is usually 2 to 40% by mole and preferably 3 to 30% by mole and more preferably 5 to 20% by mole based on total molar of all the structural units of RESIN (A).

Examples of the other monomer having no acid-labile group include the fluorine-containing monomers represented by the following formulae.

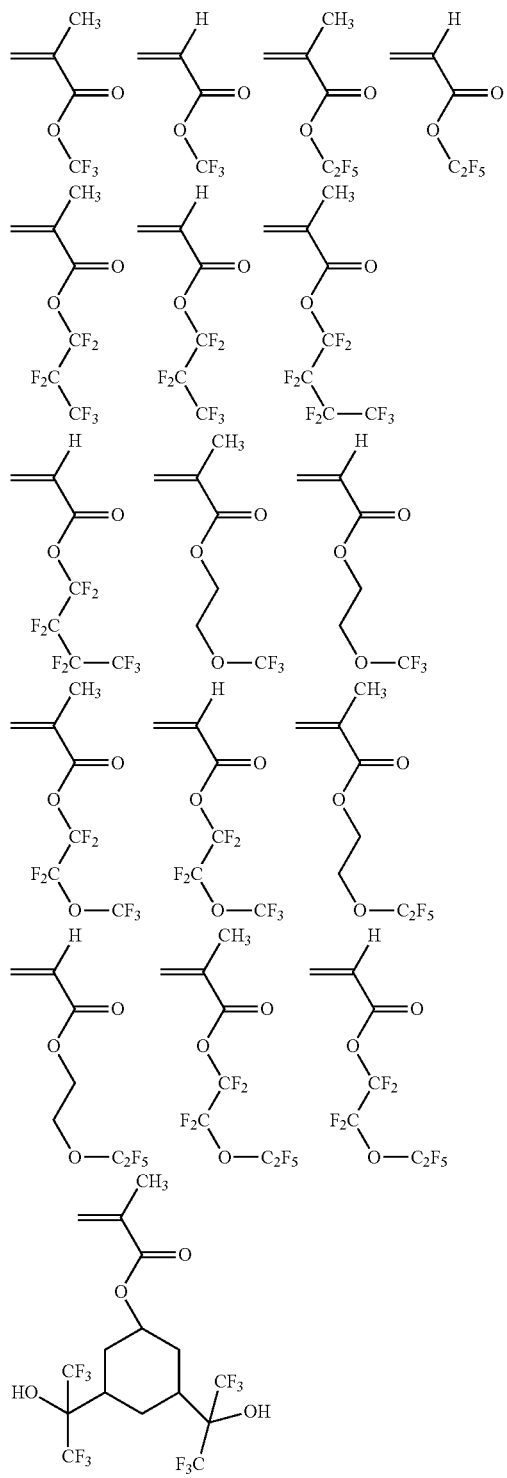

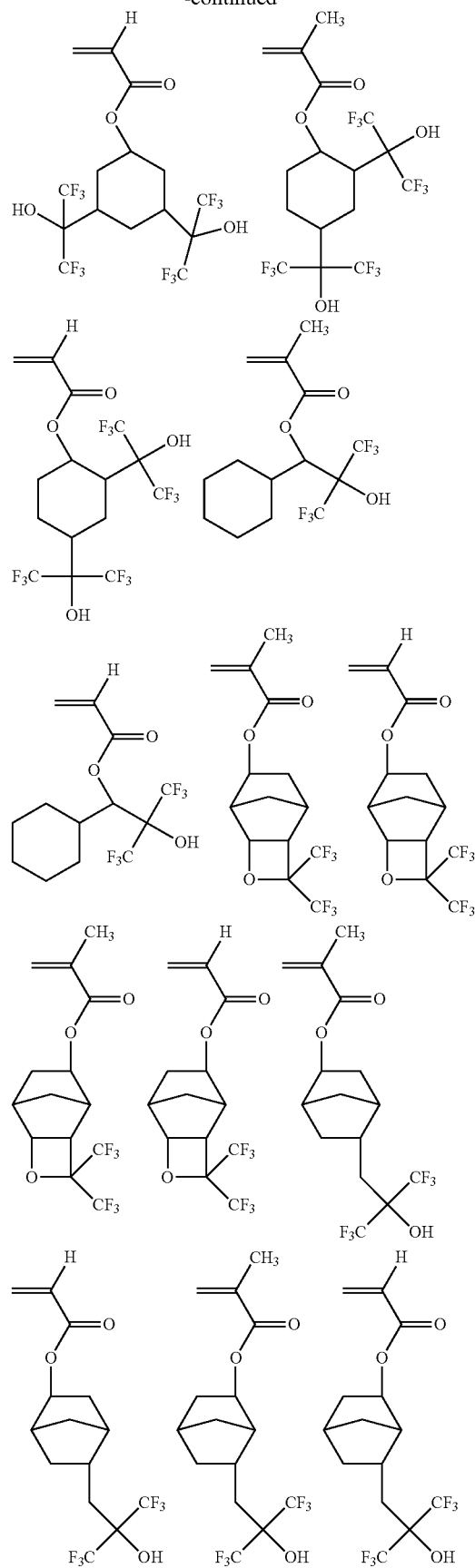
-continued

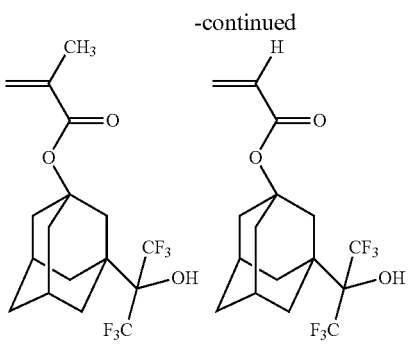

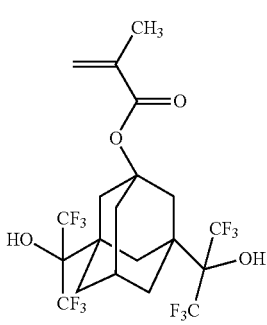

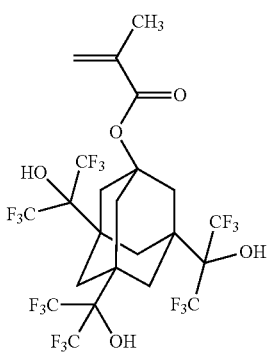

Among them, preferred are 5-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 6-(3,3,3-trifluoro-2-hydroxy-2-(trifluoromethyl)propyl)bicyclo[2.2.1]hept-2-yl acrylate, 5-(3,3,3-trifluoro-2-hydroxy-2-(trifluoromethyl)propyl)bicyclo[2.2.1]hept-2-yl methacrylate, 4,4-bis(trifluoromethyl)-3-oxatricyclo[4.2.1.0$^{2,5}$]nonyl acrylate and 4,4-bis(trifluoromethyl)-3-oxatricyclo[4.2.1.0$^{2,5}$]nonyl methacrylate.

When RESIN (A) contains a structural unit derived from the above-mentioned fluorine-containing monomer, the content thereof is usually 1 to 20% by mole based on total molar of all the structural units of RESIN (A), and preferably 2 to 15% by mole and more preferably 3 to 10% by mole.

Examples of the other monomer having no acid-labile group include the monomers having a group represented by the formula (3):

wherein $R^{10}$ represents a C1-C6 fluorinated alkyl group, in its side chain.

Examples of the C1-C6 fluorinated alkyl group include a difluoromethyl group, a trifluoromethyl group, a 1,1-difluoroethyl group, a 2,2-difluoroethyl group, a 2,2,2-trifluoroethyl group, a perfluoroethyl group, a 1,1,2,2-tetrafluoropropyl group, a 1,1,2,2,3,3-hexafluoropropyl group, a (perfluoroethyl)methyl group, a 1-(trifluoromethyl)-1,2,2,2-tetrafluoroethyl group, a perfluoropropyl group, a 1,1,2,2-tetrafluorobutyl group, a 1,1,2,2,3,3-hexafluorobutyl group, a 1,1,2,2,3,3,4,4-octafluorobutyl group, a perfluorobutyl group, a 1,1-bis(trifluoromethyl)-2,2,2-trifluoroethyl group, 2-(perfluoropropyl)ethyl group, a 1,1,2,2,3,3,4,4-octafluoropentyl group, a perfluoropentyl group, a 1,1,2,2,3,3,4,4,5,5-decafluoropentyl group, a 1,1-bis(trifluoromethyl)-2,2,3,3,3,-pentafluoropropyl group, a perfluoropentyl group, a 2-(perfluorobutyl)ethyl group, a 1,1,2,2,3,3,4,4,5,5-decafluorohexyl group, a 1,1,2,2,3,3,4,4,5,5,6,6-dodecafluorohexyl group, a (perfluoropentyl)methyl group and a perfluorohexyl group. Among them preferred is a C1-C4 fluorinated alkyl group, and more preferred are a trifluoromethyl group, a perfluoroethyl group and a perfluoropropyl group, and especially preferred is a trifluoromethyl group.

Examples of the monomer having the group represented by the formula (3) in its side chain include the following.

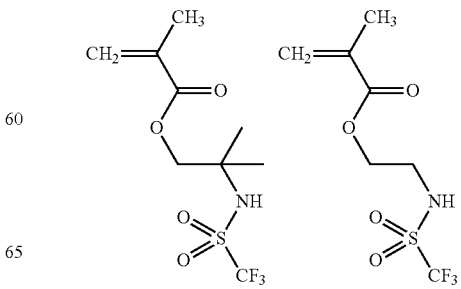

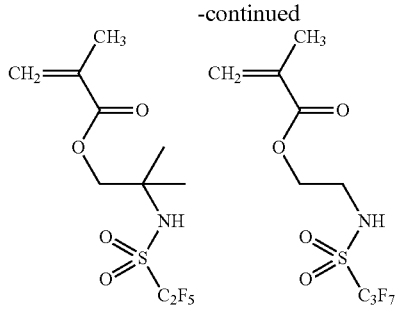
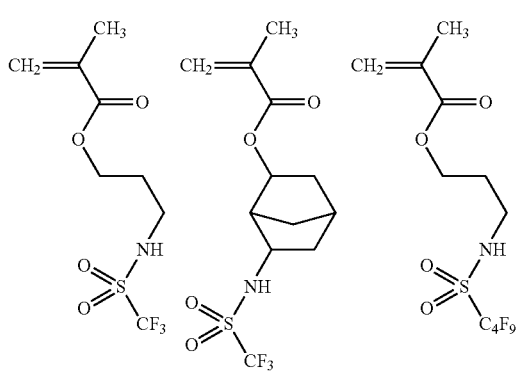
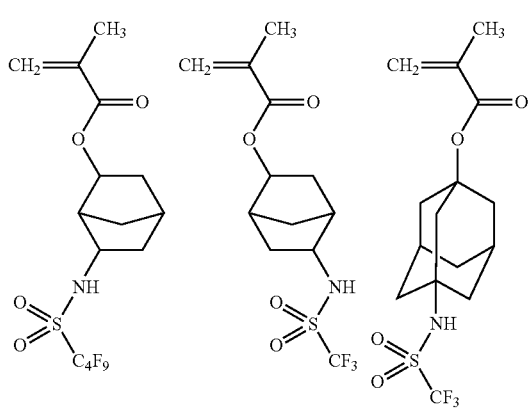
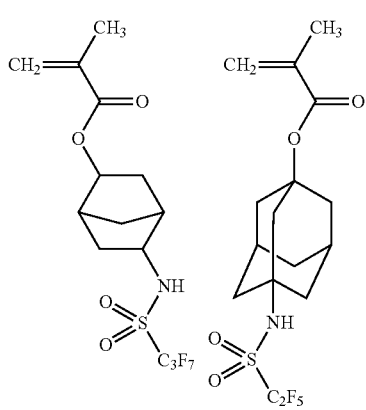

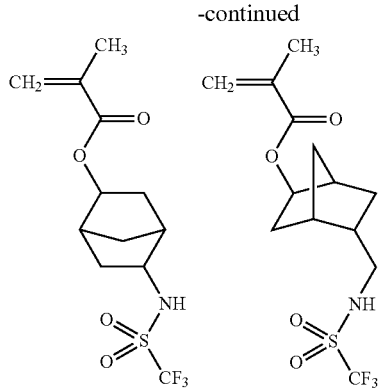

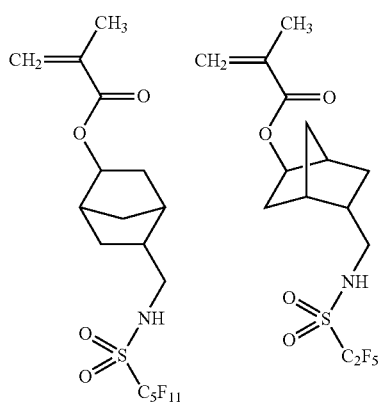

Examples of the monomer having the group represented by the formula (3) in its side chain include the above-mentioned monomers wherein the following partial structure M' is replaced by the following partial structure A'.

(partial structure M')  (partial structure A')

Examples of the monomer having the group represented by the formula (3) in its side chain include the following:

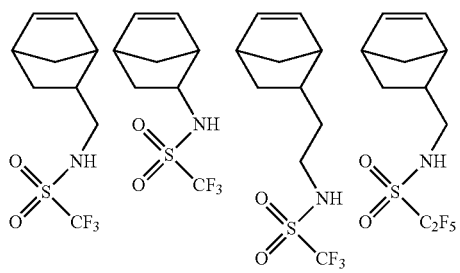

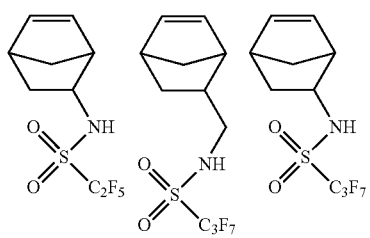

When RESIN (A) contains a structural unit derived from the above-mentioned monomer having the group represented by the formula (3) in its side chain, the content thereof is usually 1 to 30% by mole based on total molar of all the structural units of RESIN (A), and preferably 3 to 25% by mole and more preferably 5 to 20% by mole.

Examples of the other monomer having no acid-labile group include the monomers having a group represented by the formula (4):

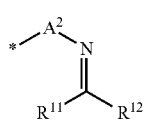

(4)

wherein $R^{11}$ represents a C6-C12 aromatic hydrocarbon group which may have one or more substituents, $R^{12}$ represents a C1-C12 hydrocarbon group which may have one or more substituents and which may contain one or more heteroatoms, and $A^2$ represents a single bond, —$(CH_2)_m$—$SO_2$—O—* or —$(CH_2)_m$—CO—O—* in which one or more —$CH_2$— may be replaced by —O—, —CO— or —$SO_2$— and in which one or more hydrogen atoms may be replaced by a fluorine atom, and m represents an integer of 1 to 12, in its side chain.

Examples of the C6-C12 aromatic hydrocarbon group include a phenyl group, a biphenyl group, a fluorenyl group, a naphthyl group and an anthryl group.

Examples of the substituents of the aromatic hydrocarbon group include a C1-C4 alkyl group such as a methyl group, an ethyl group, a propyl group, an isopropyl group, a butyl group, an isobutyl group and a tert-butyl group, a halogen atom such as a fluorine atom, a chlorine atom and a bromine atom, a phenyl group, a nitro group, a cyano group, a hydroxyl group, a phenoxy group and a tert-butylphenyl group.

Examples of $R^{11}$ include the following. In the following formulae, * represents a binding position to —$C(R^{12})$=N.

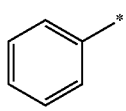

(R$^{11}$-1)

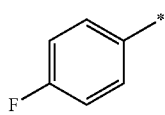

(R$^{11}$-2)

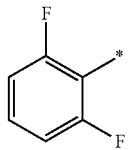

(R$^{11}$-3)

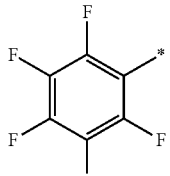

(R$^{11}$-4)

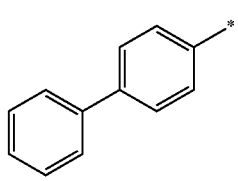

(R$^{11}$-5)

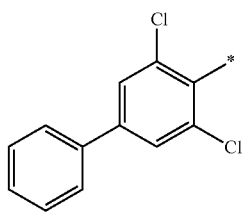

(R$^{11}$-6)

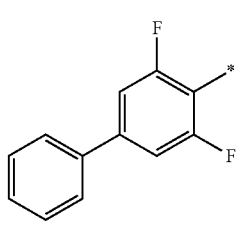

(R$^{11}$-7)

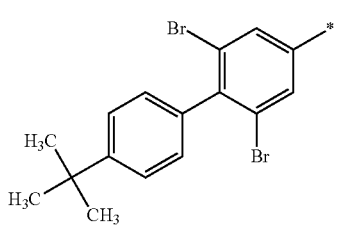

(R$^{11}$-8)

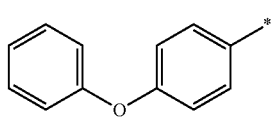

(R$^{11}$-9)

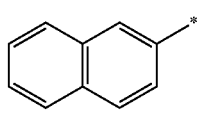

(R$^{11}$-10)

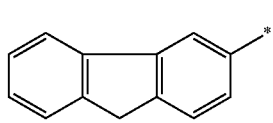

(R$^{11}$-11)

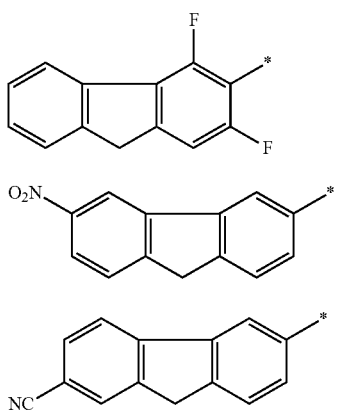

(R11-12)
(R11-13)
(R11-14)

Examples of the C1-C12 hydrocarbon group include a C1-C12 chain aliphatic hydrocarbon group, a C3-C12 alicyclic hydrocarbon group and a C6-C12 aromatic hydrocarbon group. Examples of the C1-C12 chain aliphatic hydrocarbon group include a linear aliphatic hydrocarbon group such as a methyl group, an ethyl group, a propyl group, a butyl group, a pentyl group, a hexyl group, a heptyl group, an octyl group, a nonyl group, a decyl group, an undecyl group and a dodecyl group, and a branched chain aliphatic hydrocarbon group such as an isopropyl group, a sec-butyl group, a tert-butyl group, a methylpentyl group, an ethylpentyl group, a methylhexyl group, an ethylhexyl group, a propylhexyl group and a tert-octyl group. Preferred is a branched chain aliphatic hydrocarbon group, and more preferred are an isopropyl group, a sec-butyl group, a tert-butyl group and an ethylhexyl group.

Examples of the C3-C12 alicyclic hydrocarbon group include the following. In the following formulae, * represents a binding position to —C($R^{11}$)═N.

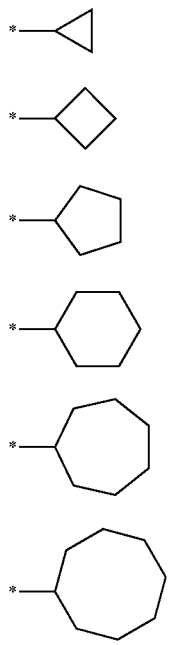

(R12-19)
(R12-20)
(R12-21)
(R12-22)
(R12-23)
(R12-24)

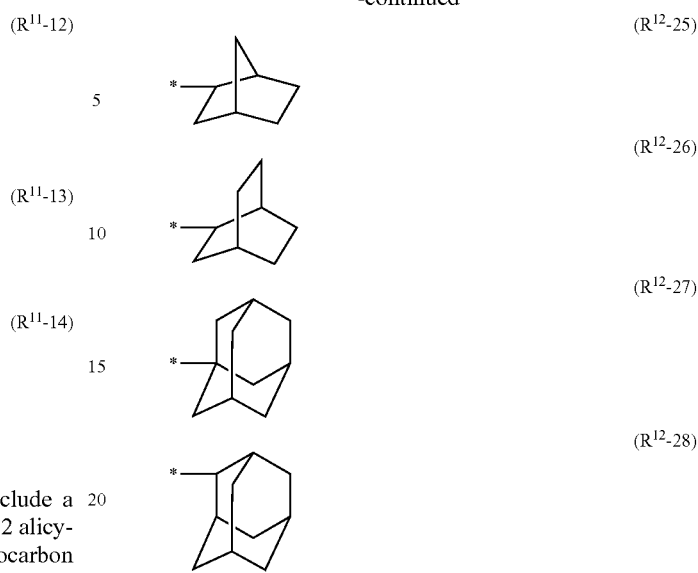

(R12-25)
(R12-26)
(R12-27)
(R12-28)

The C1-C12 hydrocarbon group may contain one or more heteroatoms such as a halogen atom, a sulfur atom, an oxygen atom and a nitrogen atom, and it may also contain a group formed by combining two or more heteroatoms such as —SO$_2$— and —CO—. Examples of the C1-C12 hydrocarbon group containing one or more heteroatoms include the following.

*—CF$_3$ (R12-1)
*—CN (R12-2)
*—CH$_3$ (R12-3)
*—CF$_2$CH$_3$ (R12-4)
*—CF$_2$CF$_3$ (R12-5)
*—CF$_2$CF$_2$CF$_3$ (R12-6)
*—CF$_2$C$_2$H$_5$ (R12-7)
*—CF$_2$CF$_2$CF$_2$—CO$_2$—CH$_3$ (R12-8)

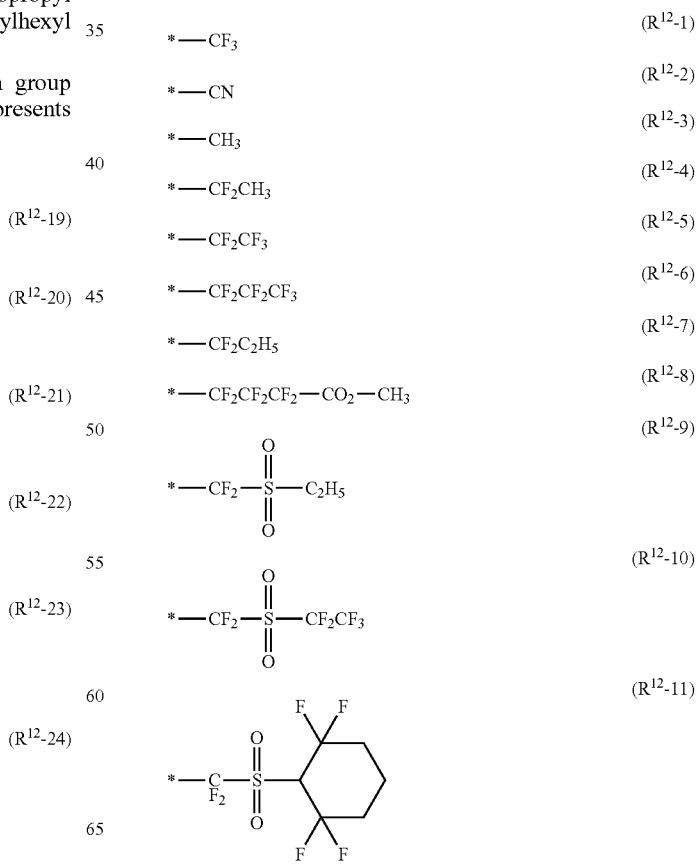

(R12-9)
(R12-10)
(R12-11)

-continued
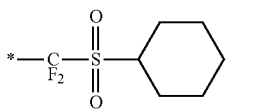 (R¹²-12)
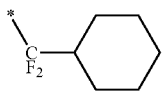 (R¹²-13)
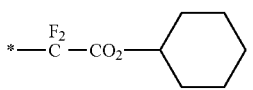 (R¹²-14)
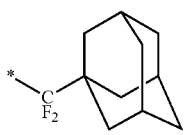 (R¹²-15)
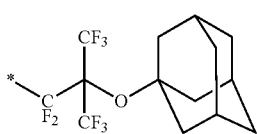 (R¹²-16)
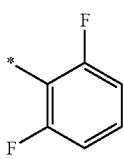 (R¹²-17)
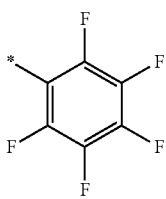 (R¹²-18)
Examples of the C6-C12 aromatic hydrocarbon group include the same as those of R¹¹.
Examples of A² include the following.
 (A²-1)
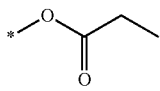 (A²-2)
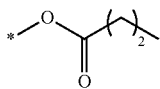 (A²-3)
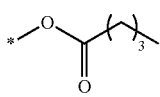 (A²-4)
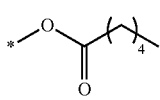 (A²-5)
-continued
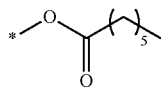 (A²-6)
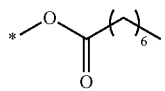 (A²-7)
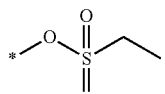 (A²-8)
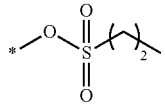 (A²-9)
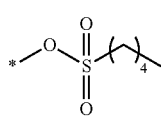 (A²-10)
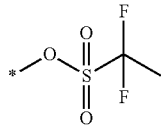 (A²-11)
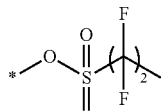 (A²-12)
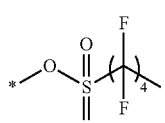 (A²-13)
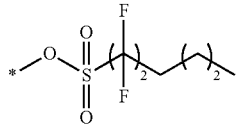 (A²-14)
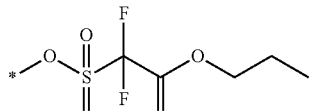 (A²-15)
 (A²-16)
wherein * represents a binding position to —N=C(R¹¹)(R¹²).
In the above-mentioned formulae, the group represented by the formula (A²-1) represents a single bond.

Preferable examples of the monomer having the group represented by the formula (4) include a monomer represented by the formula (a6-1):

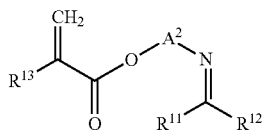

(a6-1)

wherein $A^2$, $R^{11}$ and $R^{12}$ are the same as defined above, and $R^{13}$ represents a hydrogen atom or a methyl group.

Examples of the monomer represented by the formula (a6-1) include the following.

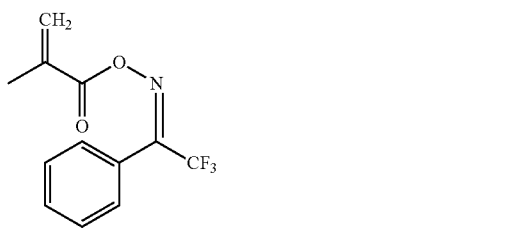
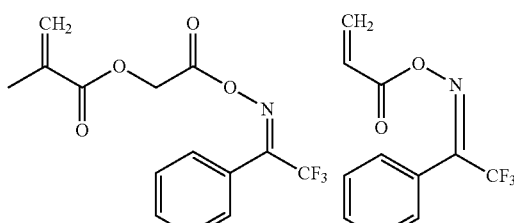
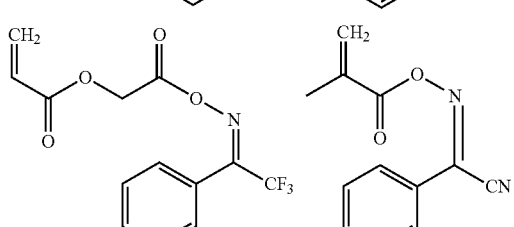
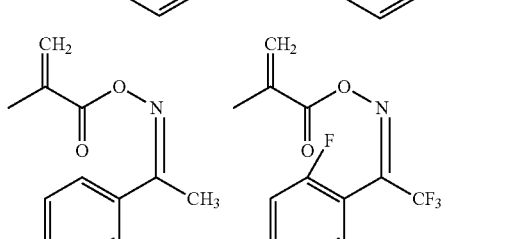
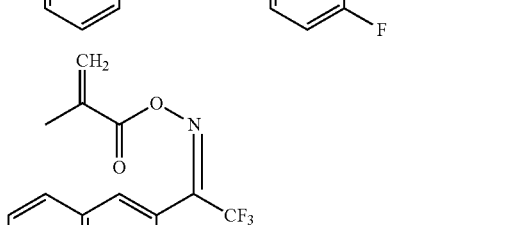

-continued

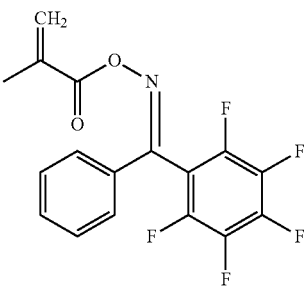
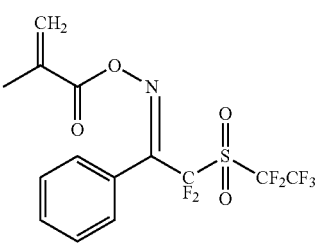
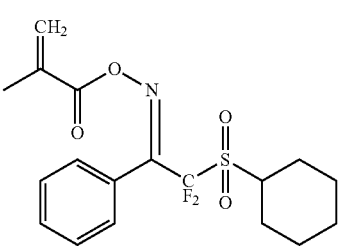
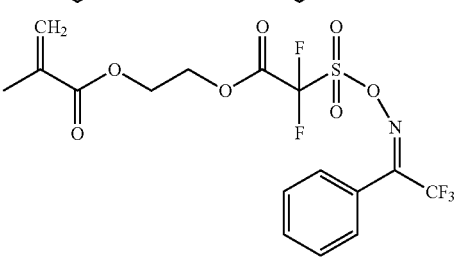
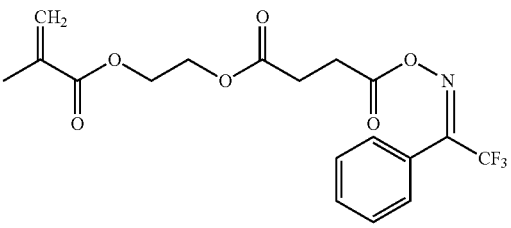
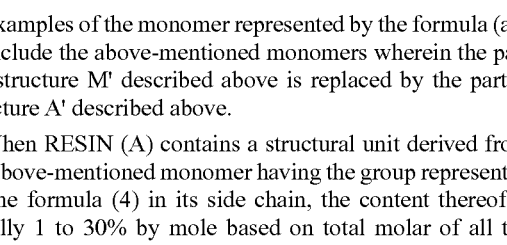

Examples of the monomer represented by the formula (a6-1) include the above-mentioned monomers wherein the partial structure M' described above is replaced by the partial structure A' described above.

When RESIN (A) contains a structural unit derived from the above-mentioned monomer having the group represented by the formula (4) in its side chain, the content thereof is usually 1 to 30% by mole based on total molar of all the structural units of RESIN (A), and preferably 3 to 25% by mole and more preferably 5 to 20% by mole.

Examples of the other monomer having no acid-labile group include the monomers represented by the formula (a4-7):

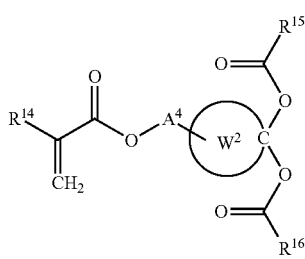

(a4-7)

wherein $R^{14}$ represents a hydrogen atom, a halogen atom, a C1-C6 alkyl group or a C1-C6 haloalkyl group, $A^4$ represents a single bond or a C1-C17 divalent aliphatic hydrocarbon group in which one or more —$CH_2$— other than —$CH_2$— bonded to $R^{14}$—$C(=CH_2)$—CO—O— can be replaced by —O— or —CO—, ring $W^2$ represents a C3-C36 aliphatic ring, $R^{15}$ and $R^{16}$ each independently represent a C1-C6 alkyl group a C1-C6 haloalkyl group.

The C3-C36 aliphatic ring may be a monocyclic ring or a polycyclic ring. Preferred is a C5-C18 aliphatic ring, and more preferred is a C6-C12 aliphatic ring. Examples thereof include the above-mentioned aliphatic rings represented by the formulae (KA-1) to (KA-22), and a cyclohexane ring, an adamantane ring, a norbornane ring and a norbornene ring are preferable.

Examples of the C1-C17 divalent aliphatic hydrocarbon group in clued the same as described above. The C1-C17 divalent aliphatic hydrocarbon group may have one or more substituents. The C1-C17 divalent aliphatic hydrocarbon group includes the above-mentioned alkanediyl group, the above-mentioned divalent alicyclic hydrocarbon group, and the group formed by combining the above-mentioned alkanediyl group and the above-mentioned divalent alicyclic hydrocarbon group.

Examples of the group formed by combining the above-mentioned alkanediyl group and the above-mentioned divalent alicyclic hydrocarbon group include the following groups represented by the formulae ($X^X$-A), ($X^X$-B) and ($X^X$-C):

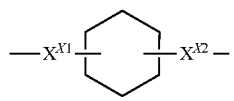

($X^x$-A)

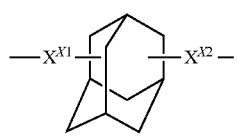

($X^x$-B)

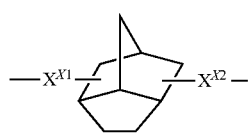

($X^x$-C)

wherein $X^{X1}$ and $X^{X2}$ each independently represent a single bond or a C1-C6 alkylene group optionally substituted, with the proviso that $X^{X1}$ and $X^{X2}$ are not single bonds at the same time, and the total carbon number of each of the groups represented by the formulae ($X^X$-A), ($X^X$-B) and ($X^X$-C) is 17 or less.

$A^4$ is preferably a single bond or *—$(CH_2)_{s1}$—CO—O— in which * represents a binding position to —O— and s1 represents an integer of 1 to 6, and more preferably a single bond or *—$CH_2$—CO—O—.

Examples of the C1-C6 alkyl group include the same as described above, and examples of the C1-C6 haloalkyl group include a fluorinated alkyl group such as a trifluoroalkyl group, a perfluoroethyl group, a perfluoropropyl group and a perfluorobutyl group, and a trifluoroalkyl group, a perfluoroethyl group and a perfluoropropyl group are preferable.

$R^{14}$ is preferably a hydrogen atom or a methyl group.

Examples of the monomer represented by the formula (aa4-7) include the following.

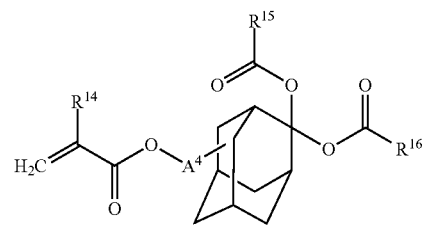

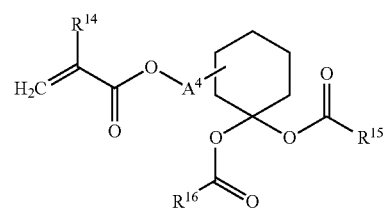

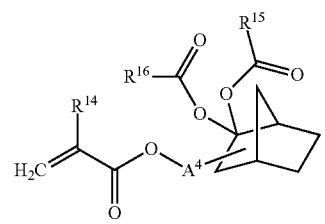

Among them, preferred are the following monomers.

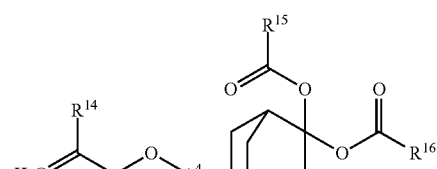

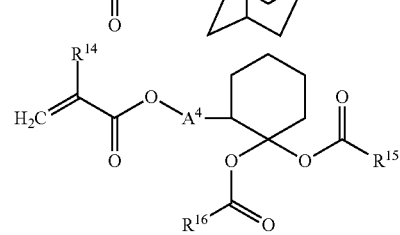

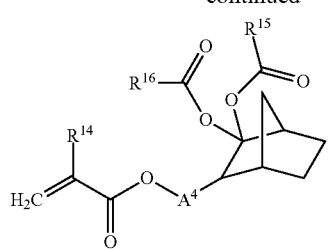
Specific examples thereof include the following and the following monomers wherein the above-mentioned partial structure M' is replaced by the above-mentioned partial structure A'.
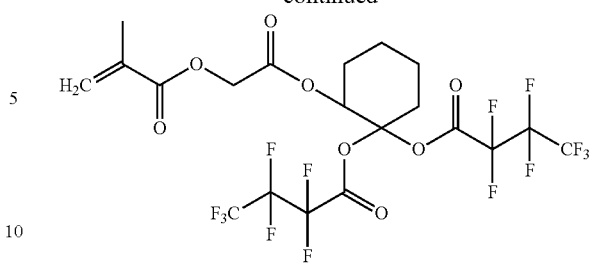
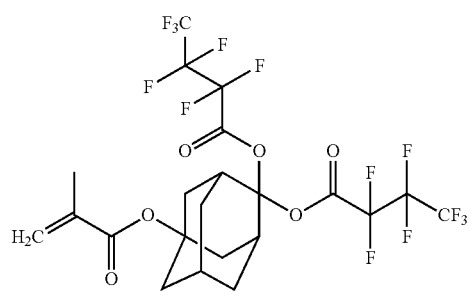
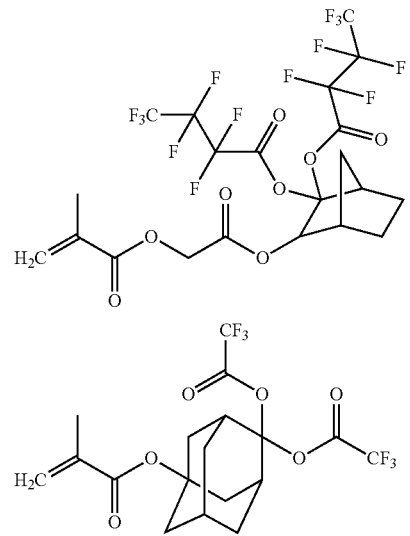
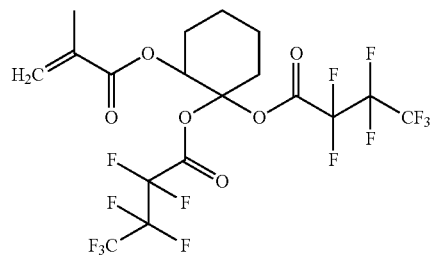
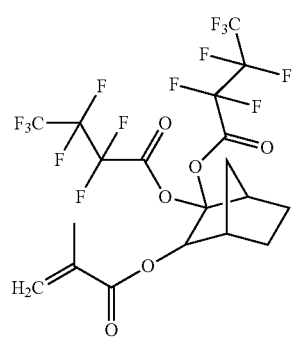
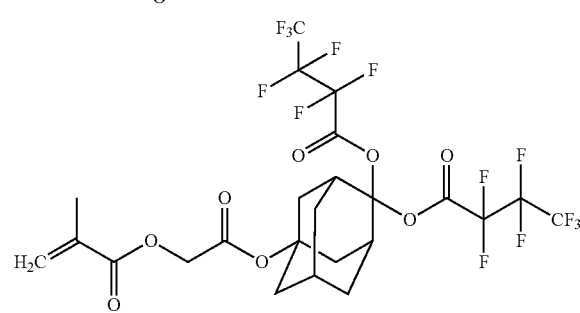
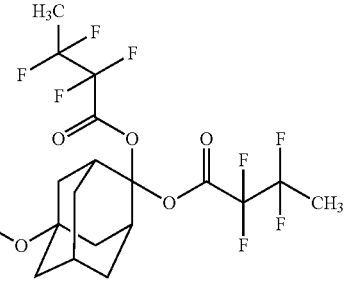

-continued

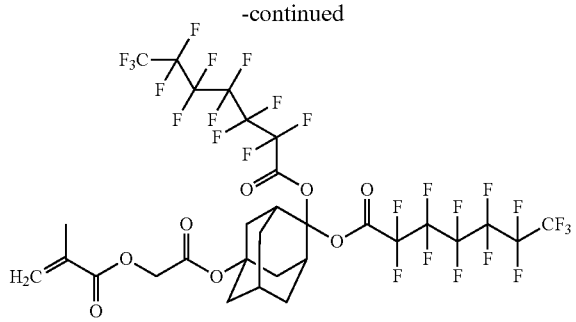

The monomer represented by the formula (a4-7) can be produced by reacting a compound represented by the formula (a4-7-a) with a compound represented by the formula (a4-7-b).

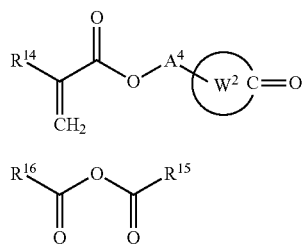

(a4-7-a)

(a4-7-b)

Examples of the compound represented by the formula (a4-7-a) include 1-methacryloyloxy-4-oxoadamantane described in JP 2002-226436 A. Examples of the compound represented by the formula (a4-7-b) include pentafluoropropionic anhydride, heptafluorobutyric anhydride and trifluoroacetic anhydride.

The reaction is preferably conducted at the temperature nearly to the boiling point of the compound represented by the formula (a4-7-b).

When RESIN (A) contains a structural unit derived from the above-mentioned monomer represented by the formula (a4-7), the content thereof is usually 1 to 30% by mole based on total molar of all the structural units of RESIN (A), and preferably 3 to 25% by mole and more preferably 5 to 20% by mole.

Preferable RESIN (A) is a resin comprising the unit represented by the formula (aa), the structural unit derived from the monomer having an acid-labile group and the structural unit derived from the monomer having no acid-labile group, and more preferable RESIN (A) is a resin comprising the unit represented by the formula (aa), the structural unit derived from the monomer having an acid-labile group and the structural unit derived from the monomer having one or more hydroxyl groups and/or the monomer having a lactone ring. The structural unit derived from the monomer having an acid-labile group is preferably the structural unit represented by the formula (a1-1) or (a1-2), and is more preferably the structural unit represented by the formula (a1-1). The structural unit derived from the monomer having one or more hydroxyl groups is preferably the structural unit represented by the formula (a2-1), and the structural unit derived from the monomer having a lactone ring is preferably the structural unit represented by the formula (a3-1) or (a3-2).

RESIN (A) can be produced according to known polymerization methods such as radical polymerization.

RESIN (A) usually has 2,500 or more of the weight-average molecular weight, preferably 3,000 or more of the weight-average molecular weight. RESIN (A) usually has 50,000 or less of the weight-average molecular weight, preferably has 30,000 or less of the weight-average molecular weight. The weight-average molecular weight can be measured with gel permeation chromatography.

The content of RESIN (A) in the photoresist composition of the present invention is usually 80% by mass or more based on sum of solid component, and usually 99% by mass or less. In this specification, "solid component" means components other than solvent in the photoresist composition.

The photoresist composition of the present invention contains an acid generator, and can contain two or more kinds of the acid generators.

The acid generator is a substance which is decomposed to generate an acid by applying a radiation such as a light, an electron beam or the like on the substance itself or on a photoresist composition containing the substance. The acid generated from the acid generator acts on the resin resulting in cleavage of the acid-labile group existing in the resin.

Examples of the acid generator include a nonionic acid generator, an ionic acid generator and the combination thereof. Examples of the nonionic acid generator include an organo-halogen compound, a sulfone compound such as a disulfone, a ketosulfone and a sulfonyldiazomethane, a sulfonate compound such as a 2-nitrobenzylsulfonate, an aromatic sulfonate, an oxime sulfonate, an N-sulfonyloxyimide, a sulfonyloxyketone and diazonaphthoquinone 4-sulfonate. Examples of the ionic acid generator include an onium salt compound such as a diazonium salt, a phosphonium salt, a sulfonium salt and an iodonium salt. Examples of the anion of the onium salt include a sulfonic acid anion, a sulfonylimide anion and a sulfonulmethide anion. The onium salt compound is preferable.

Other examples of the acid generator include acid generators described in JP 63-26653A, JP 55-164824A, JP 62-69263A, JP 63-146038 A, JP 63-163452 A, JP 62-153853 A, JP 63-146029 A, U.S. Pat. No. 3,779,778, U.S. Pat. No. 3,849,137, DE Pat. No. 3914407 and EP Patent No. 126,712.

A fluorine-containing acid generator is preferable.

Preferable examples of the acid generator include a salt represented by the formula (B1):

(B1)

wherein $Q^1$ and $Q^2$ each independently represent a fluorine atom or a C1-C6 perfluoroalkyl group, $L^{b1}$ represents a single bond or a C1-C17 divalent aliphatic hydrocarbon group which can have one or more substituents, and one or more —$CH_2$— in the divalent aliphatic hydrocarbon group can be replaced by —O— or —CO—, Y represents a C1-C18 aliphatic hydrocarbon group which can have one or more substituents and in which one or more —$CH_2$— can be replaced by —O—, —CO— or —$SO_2$—, and $Z^+$ represents an organic cation.

Examples of the C1-C6 perfluoroalkyl group include a trifluoromethyl group, a pentafluoroethyl group, a heptafluoropropyl group, a nonafluorobutyl group, an undecafluoropentyl group and a tridecafluorohexyl group, and a trifluoromethyl group is preferable. $Q^1$ and $Q^2$ each independently preferably represent a fluorine atom or a trifluoromethyl group, and $Q^1$ and $Q^2$ are more preferably fluorine atoms.

Examples of the C1-C17 divalent aliphatic hydrocarbon group include a C1-C17 alkandiyl group, a monocyclic or polycyclic divalent saturated hydrocarbon group and a group formed by combining two or more groups selected from the group consisting of a C1-C17 alkandiyl group and a monocyclic or polycyclic divalent saturated hydrocarbon group.

Examples thereof include a linear alkanediyl group such as a methylene group, an ethylene group, a propane-1,3-diyl group, a butane-1,4-diyl group, a pentane-1,5-diyl, a hexane-1,6-diyl group, a heptane-1,7-diyl group, an octane-1,8-diyl group, a nonane-1,9-diyl group, a decane-1,10-diyl group, an undecane-1,11-diyl group, a dodecane-1,12-diyl group, a tridecane-1,13-diyl group, a tetradecane-1,14-diyl group, a pentadecane-1,15-diyl group, a hexadecane-1,16-diyl group and a heptadecane-1,17-diyl group, a branched chain alkanediyl group such as a butane-1,3-diyl group, a 2-methylpropane-1,3-diyl group, a 2-methylpropane-1,2-diyl group, a pentane-1,4-diyl group and a 2-methylbutane-1,4-diyl group, a monocyclic divalent saturated hydrocarbon group such as a cyclobutane-1,3-diyl group, a cyclopentane-1,3-diyl group, a cyclohexane-1,2-diyl group, a 1-methylcyclohexane-1,2-diyl group, a cyclohexane-1,4-diyl group, a cyclooctane-1,2-diyl group and a cyclooctane-1,5-diyl group, and a polycyclic divalent saturated hydrocarbon group such as a norbornane-2,3-diyl group, a norbornane-1,4-diyl group, a norbornane-2,5-diyl group, an adamantane-1,2-diyl group, an adamantane-1,5-diyl group and an adamantane-2,6-diyl group.

Examples of the C1-C17 aliphatic hydrocarbon group in which one or more —$CH_2$— are replaced by —O— or —CO— include *—CO—O-$L^{b2}$-, *—CO—O-$L^{b4}$-CO—O-$L^{b3}$-, *-$L^{b5}$-O—CO—, *-$L^{b7}$-O-$L^{b6}$-, *—CO—O-$L^{b8}$-O—, and *—CO—O-$L^{b10}$-O-$L^{b9}$-CO—O—, wherein $L^{b2}$ represents a single bond or a C1-C15 aliphatic hydrocarbon group, $L^{b3}$ represents a single bond or a C1-C12 aliphatic hydrocarbon group, $L^{b4}$ represents a single bond or a C1-C13 aliphatic hydrocarbon group, with proviso that total carbon number of $L^{b3}$ and $L^{b4}$ is 1 to 13, $L^{b5}$ represents a C1-C15 aliphatic hydrocarbon group, $L^{b6}$ represents a C1-C15 aliphatic hydrocarbon group, $L^{b7}$ represents a C1-C15 aliphatic hydrocarbon group, with proviso that total carbon number of $L^{b6}$ and $L^{b7}$ is 1 to 16, $L^{b8}$ represents a C1-C14 aliphatic hydrocarbon group, $L^{b9}$ represents a C1-C11 aliphatic hydrocarbon group, $L^{b10}$ represents a C1-C11 aliphatic hydrocarbon group, with proviso that total carbon number of $L^{b9}$ and $L^{b10}$ is 1 to 12, and * represents a binding position to —$C(Q^1)(Q^2)$-.

The aliphatic hydrocarbon group is preferably a saturated aliphatic hydrocarbon.

Among them, preferred is *—CO—O-$L^{b2}$-, and more preferred is *—CO—O-$L^{b2}$- in which $L^{b2}$ is a single bond or —$CH_2$—.

Examples of *—CO—O-$L^{b2}$- include *—CO—O— and *—CO—O—$CH_2$—. Examples of *—CO—O-$L^{b4}$-CO—O-$L^{b3}$- include *—CO—O—$CH_2$—CO—O—, *—CO—O—$(CH_2)_2$—CO—O—, *—CO—O—$(CH_2)_3$—CO—O—, *—CO—O—$(CH_2)_4$—CO—O—, *—CO—O—$(CH_2)_6$—CO—O—, *—CO—O—$(CH_2)_8$—CO—O—, *—CO—O—$CH_2$—$CH(CH_3)$—CO—O— and *—CO—O—$CH_2$—$C(CH_3)_2$—CO—O—. Examples of *-$L^{b5}$-O—CO— include —$CH_2$—O—CO—, *—$(CH_2)_2$—O—CO—, *—$(CH_2)_3$—O—CO—, *—$(CH_2)_4$—O—CO—, *—$(CH_2)_6$—O—CO— and *—$(CH_2)_8$—O—CO—. Examples of *-$L^{b7}$-O-$L^{b6}$- include *—$CH_2$—O—$CH_2$—. Examples of *—CO—O-$L^{b8}$-O— include *—CO—O—$CH_2$—O—, *—CO—O—$(CH_2)_2$—O—, *—CO—O—$(CH_2)_3$—O—, *—CO—O—$(CH_2)_4$—O— and *—CO—O—$(CH_2)_6$—O—. Examples of *—CO—O-$L^{b10}$-O-$L^{b9}$-CO—O— include the followings.

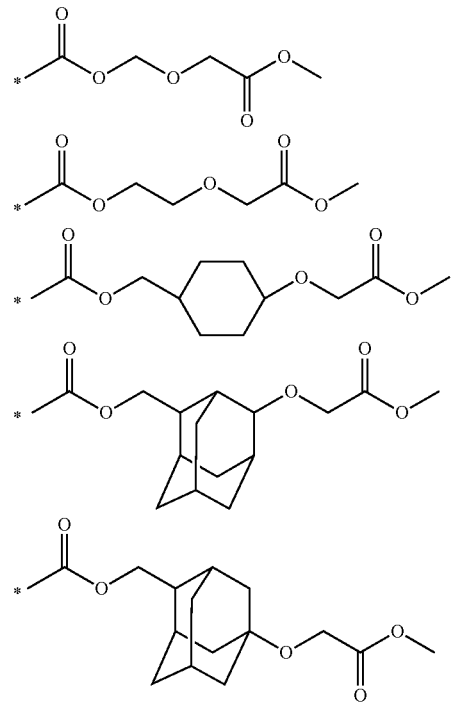

Examples of the substituent in Y include a halogen atom other than a fluorine atom, a hydroxyl group, an oxo group, a glycidyloxy group, a C2-C4 acyl group, a C1-C12 alkoxy group, a C2-C7 alkoxycarbonyl group, a C1-C12 aliphatic hydrocarbon group, a C1-C12 hydroxy-containing aliphatic hydrocarbon group, a C3-C16 saturated cyclic hydrocarbon group, a C6-C18 aromatic hydrocarbon group, a C7-C21 aralkyl group and —$(CH_2)_{j2}$—O—CO—$R^{b1}$— in which $R^{b1}$ represents a C1-C16 aliphatic hydrocarbon group, a C3-C16 saturated cyclic hydrocarbon group or a C6-C18 aromatic hydrocarbon group and j2 represents an integer of 0 to 4. Examples of the halogen atom include a chlorine atom, a bromine atom and an iodine atom. Examples of the acyl group include an acetyl group and a propionyl group, and examples of the alkoxy group include a methoxy group, an ethoxy group, a propoxy group, an isopropoxy group and a butoxy group. Examples of the alkoxycarbonyl group include a methoxycarbonyl group, an ethoxycarbonyl group, a propoxycarbonyl group, an isopropoxycarbonyl group and a butoxycarbonyl group. Examples of the aliphatic hydrocarbon group include the same as described above. Examples of the hydroxyl-containing aliphatic hydrocarbon group include a hydroxymethyl group. Examples of the C3-C16 saturated cyclic hydrocarbon group include the same as described above, and examples of the aromatic hydrocarbon group include a phenyl group, a naphthyl group, an anthryl group, a p-methylphenyl group, a p-tert-butylphenyl group and a p-adamantylphenyl group. Examples of the aralkyl group include a benzyl group, a phenethyl group, a phenylpropyl group, a trityl group, a naphthylmethyl group and a naphthylethyl group.

The C1-C18 aliphatic hydrocarbon group represented by Y includes a chain aliphatic hydrocarbon group and an alicyclic hydrocarbon group. Y is preferably an alkyl group or an alicyclic hydrocarbon group, and more preferably a C1-C6 alkyl group or a C3-C12 alicyclic hydrocarbon group, and especially preferably a C3-C12 alicyclic hydrocarbon group.

Examples of the C1-C18 aliphatic hydrocarbon group represented by Y include a methyl group, an ethyl group, a propyl group, an isopropyl group, a butyl group, an isobutyl group, a sec-butyl group, a tert-butyl group, a pentyl group, a neopentyl group, a 1-methylbutyl group, a 2-methylbutyl group, a 1,2-dimethylpropyl group, a 1-ethylpropyl group, a hexyl group, a 1-methylpentyl group, a heptyl group, an octyl group, a 2-ethylhexyl group, a nonyl group, a decyl group, an undecyl group and a dodecyl group.

Examples of the aliphatic hydrocarbon group in which one or more —CH$_2$— are replaced by —O—, —CO— or —SO$_2$— include a group having an ether structure or a cyclic ether structure, a saturated cyclic hydrocarbon group having an oxo group, a sultone ring group and a lactone ring group.

Preferable examples thereof include the groups represented by the formulae (Y1) to (Y5), and groups represented by the formulae (Y1), (Y2), (Y3) and (Y5) are more preferable and groups represented by the formulae (Y1) and (Y2) are especially preferable.

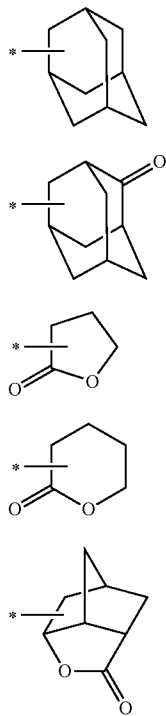

Examples of Y having one or more substituents include the followings:

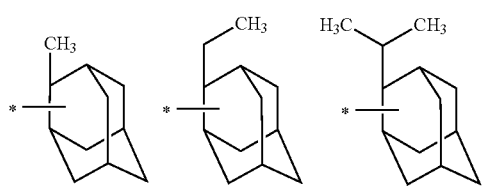

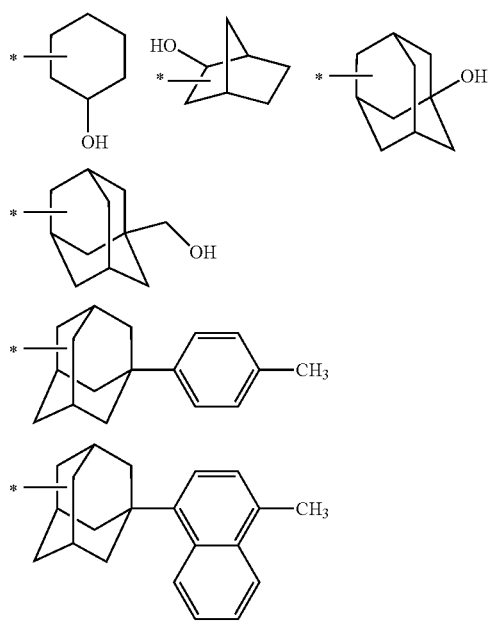

Y is preferably an adamantyl group which can have one or more substituents, and is more preferably an adamantyl group or an hydroxyadamantyl group.

Among the sulfonic acid anions of the acid generator represented by the formula (B1), preferred is a sulfonic acid anion having *—CO—O-L$^{b2}$-, and more preferred are anions represented by the formulae (b1-1-1) to (b1-1-9).

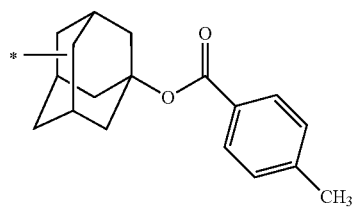
(b1-1-1)

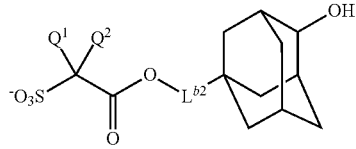
(b1-1-2)

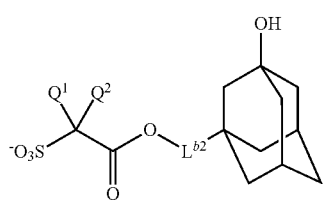
(b1-1-3)

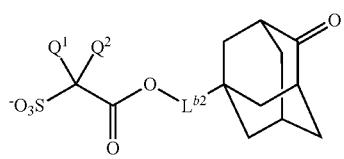

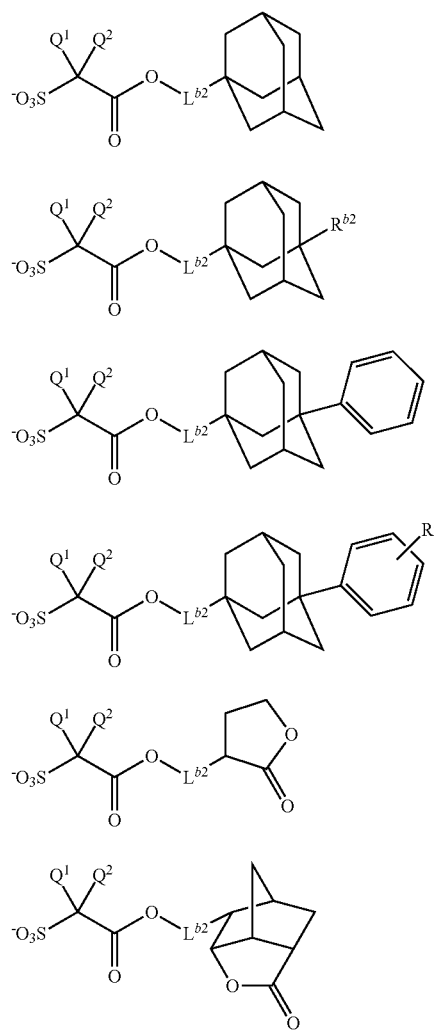

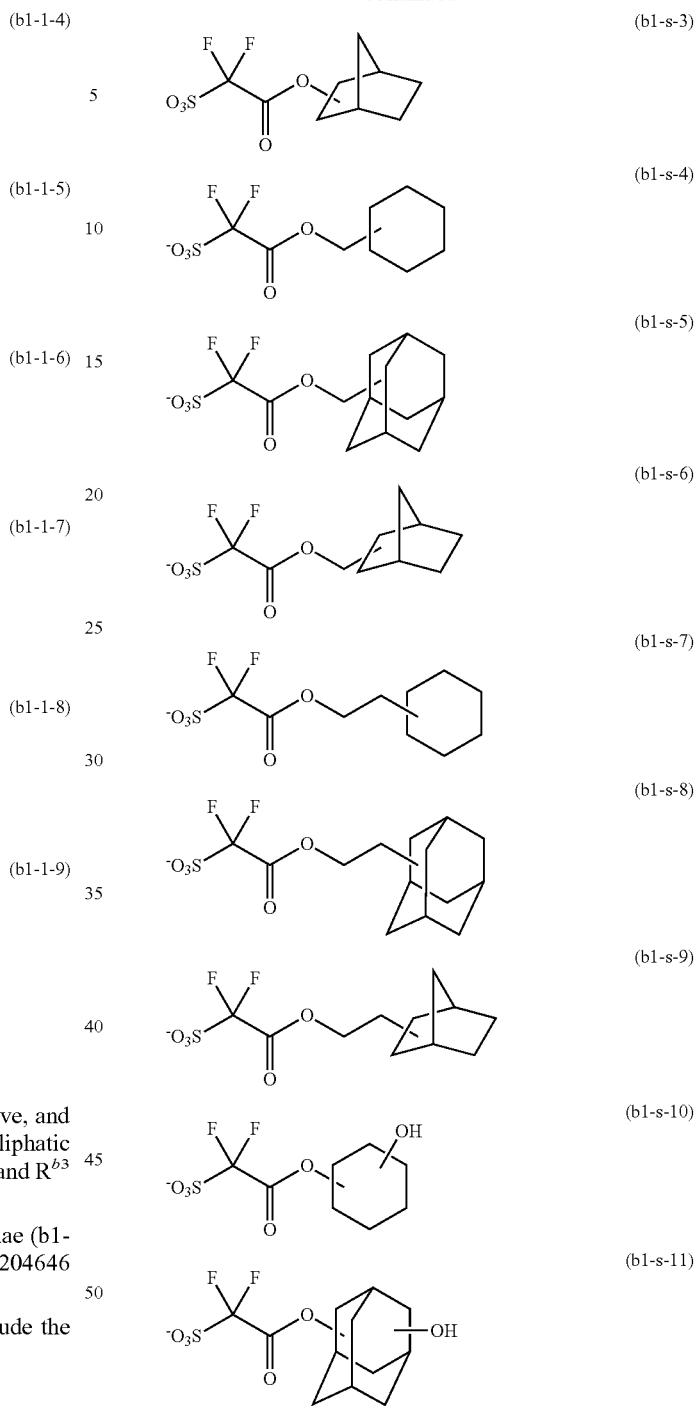

wherein $Q^1$, $Q^2$ and $L^{b2}$ are the same as defined above, and $R^{b2}$ and $R^{b3}$ each independently represent a C1-C4 aliphatic hydrocarbon group and it is more preferred that $R^{b2}$ and $R^{b3}$ each independently represent a methyl group.

Examples of the anions represented by the formulae (b1-1-1) to (b1-1-9) include anions described in JP 2010-204646 A.

Specific examples of the sulfonic acid anion include the followings.

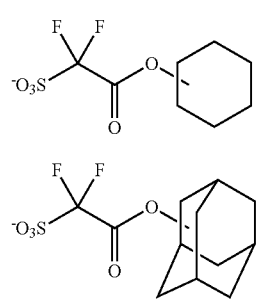

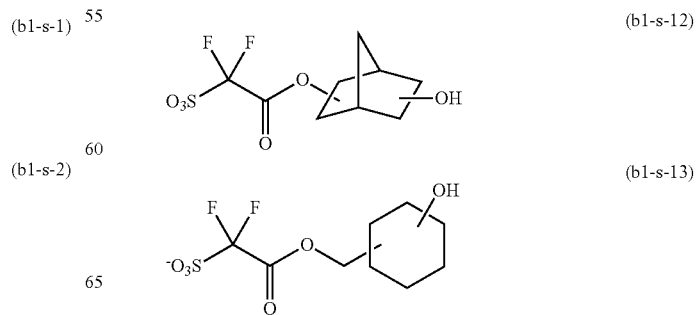

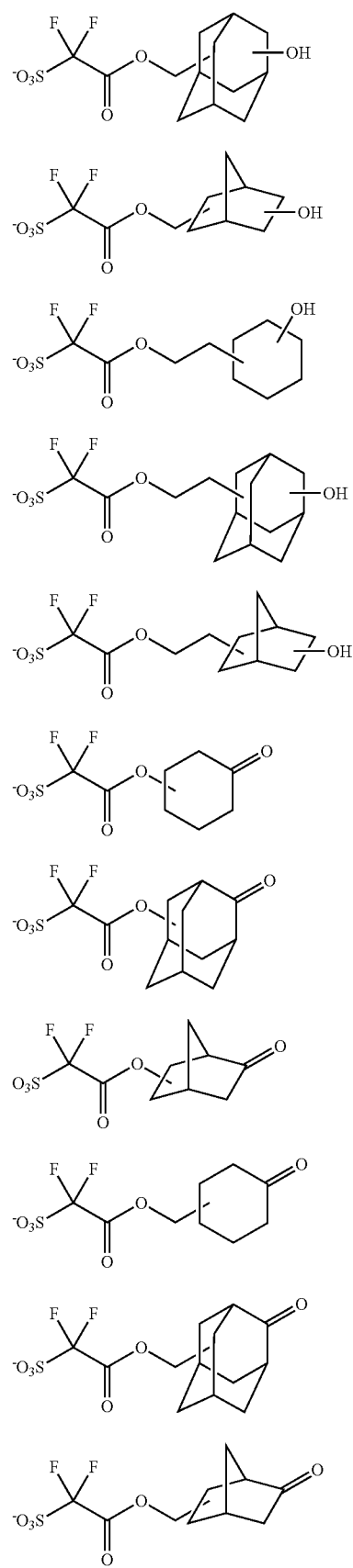
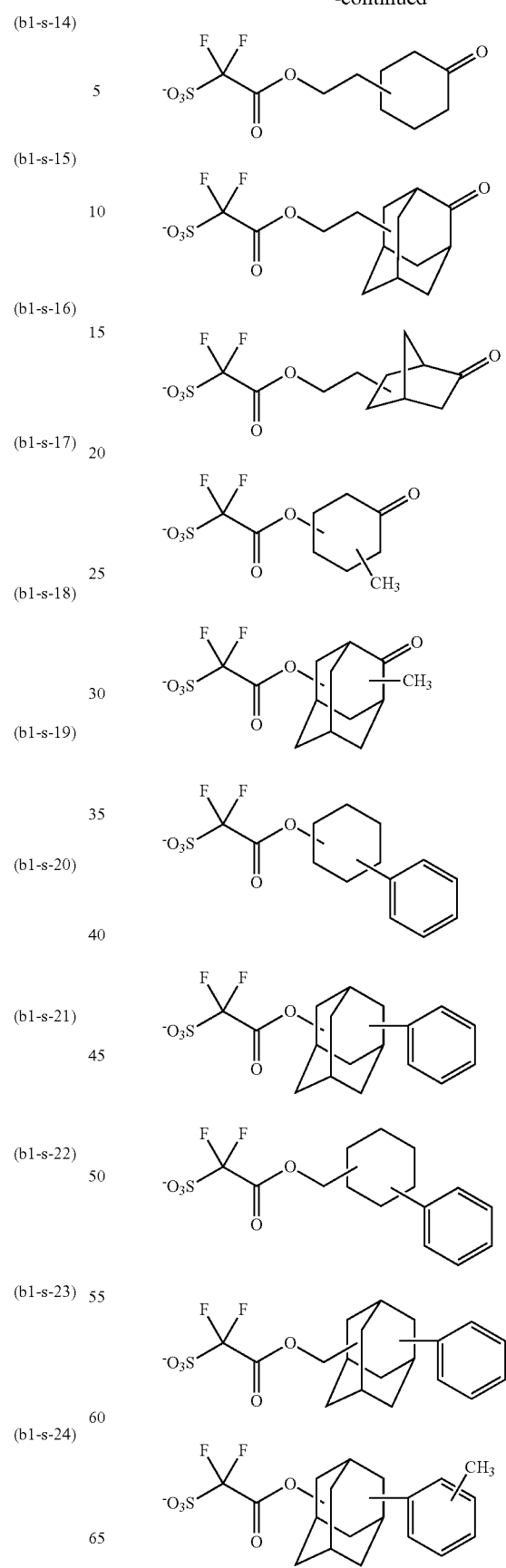

-continued

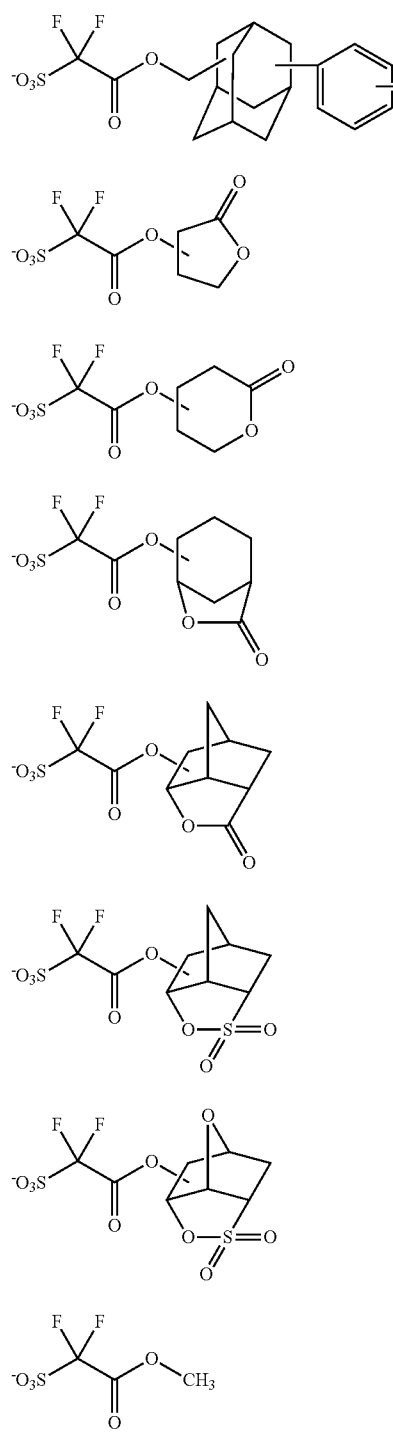

(b1-s-35)
(b1-s-36)
(b1-s-37)
(b1-s-38)
(b1-s-39)
(b1-s-40)
(b1-s-41)
(b1-s-42)

Examples of the organic counter ion represented by $Z^+$ include an onium cation such as a sulfonium cation, an iodonium cation, an ammonium cation, a benzothiazolium cation and a phosphonium cation, and a sulfonium cation and an iodonium cation are preferable, and a sulfonium cation is more preferable.

Preferable examples of the organic counter ion represented by $Z^+$ include the organic cations represented by the formulae (b2-1) to (b2-4):

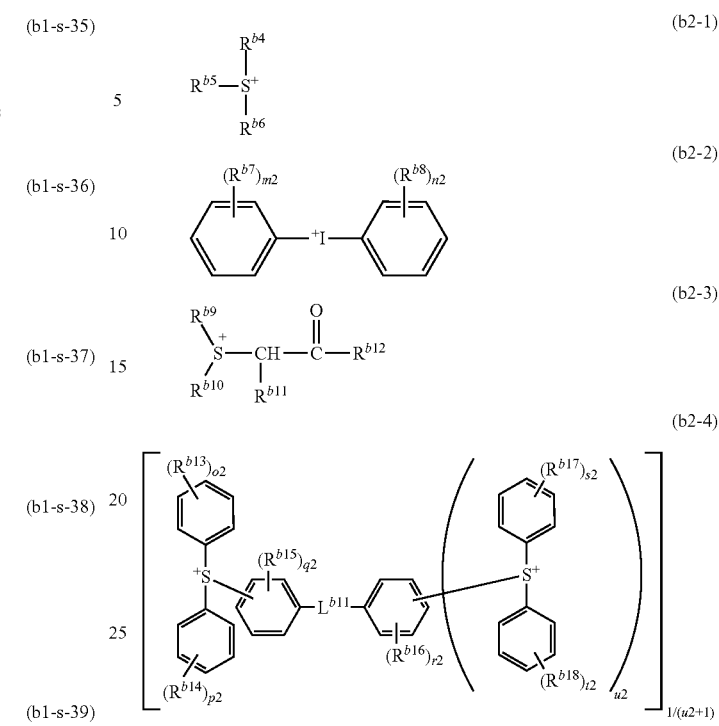

(b2-1)
(b2-2)
(b2-3)
(b2-4)

In the formulae (b2-1) to (b2-4), $R^{b4}$, $R^{b5}$ and $R^{b6}$ independently represent a C1-C30 hydrocarbon group. As the C1-C30 hydrocarbon group, a C1-C30 alkyl group, a C3-C18 alicyclic hydrocarbon group and a C6-C18 aromatic hydrocarbon group are preferable. The alkyl group can have one or more substituents selected from the group consisting of a hydroxyl group, a C1-C12 alkoxy group and a C6-C18 aromatic hydrocarbon group. The C3-C18 alicyclic hydrocarbon group can have one or more substituents selected from the group consisting of a halogen atom, a C2-C4 acyl group and a glycidyloxy group. The C6-C18 aromatic hydrocarbon group can have one or more substituents selected froth the group consisting of a halogen atom, a hydroxyl group, a C1-C18 aliphatic hydrocarbon group, a C3-C18 saturated cyclic hydrocarbon group and a C1-C12 alkoxy group.

$R^{b7}$ and $R^{b8}$ are independently in each occurrence a hydroxyl group, a C1-C12 alkyl group or a C1-C12 alkoxy group, m2 and n2 independently represents an integer of 0 to 5.

$R^{b9}$ and $R^{b10}$ independently represent a C1-C18 alkyl group or a C3-C18 alicyclic hydrocarbon group.

$R^{b11}$ represents a hydrogen atom, a C1-C18 alkyl group, a C3-C18 alicyclic hydrocarbon group or a C6-C18 aromatic hydrocarbon group.

When $R^{b9}$, $R^{b10}$ and $R^{b11}$ each independently represent an alkyl group, it is preferably a C1-C12 alkyl group, and when $R^{b9}$, $R^{b10}$ and $R^{b11}$ each independently represent an alicyclic hydrocarbon group, it is preferably C3-C18 alicyclic hydrocarbon group and more preferably C4-C12 alicyclic hydrocarbon group.

$R^{b12}$ represents a C1-C18 hydrocarbon group and examples thereof include a C1-C18 aliphatic hydrocarbon group, a C3-C18 saturated cyclic hydrocarbon group and a C6-C18 aromatic hydrocarbon group and the aromatic hydrocarbon group can have one or more substituents selected from the group consisting of a C1-C12 aliphatic hydrocarbon group, a C1-C12 alkoxy group, a C3-C18 saturated cyclic hydrocarbon group and a (C1-C12 alkyl) carbonyloxy group.

$R^{b9}$ and $R^{b10}$ can be bonded to form a C2-C11 divalent acyclic hydrocarbon group which forms a ring together with the adjacent S+, and one or more —CH$_2$— in the divalent acyclic hydrocarbon group may be replaced by —CO—, —O— or —S—, and preferred is a C2-C6 divalent acyclic hydrocarbon group.

$R^{b11}$ and $R^{b12}$ can be bonded each other to form a C1-C10 divalent acyclic hydrocarbon group which forms a 2-oxocycloalkyl group together with the adjacent —CHCO—, and one or more —CH$_2$— in the divalent acyclic hydrocarbon group may be replaced by —CO—, —O— or —S—, and preferred is a C1-C5 divalent acyclic hydrocarbon group.

$R^{b13}$, $R^{b14}$, $R^{b15}$, $R^{b16}$, $R^{b17}$ and $R^{b18}$ independently represent a hydroxyl group, a C1-C12 alkyl group or a C1-C12 alkoxy group.

$L^{b11}$ represents —S— or —O— and o2, p2, s2 and t2 each independently represents an integer of 0 to 5, q2 and r2 each independently represents an integer of 0 to 4, and u2 represents 0 or 1.

Preferable examples of the aliphatic hydrocarbon group represented by $R^{b4}$ to $R^{b6}$ include an alkyl group such as a methyl group, an ethyl group, a propyl group, an isopropyl group, 2,2-dimethylethyl group, 1-methylpropyl group, a 2-methylpropyl group, a 1,2-dimethylpropyl group, a 2,2-dimethylpropyl group, a 1-ethylpropyl group, a butyl group, a sec-butyl group, a tert-butyl group, a pentyl group, a 1-methylbutyl group, a 2-methylbutyl group, a 3-methylbutyl group, a hexyl group, a 1-propylbutyl group, a 1-methylpentyl group, a 2-ethylhexyl group, a 1,4-dimethylhexyl group, a 1-methylheptyl group, an octyl group, a decyl group, a dodecyl group, a hexadecyl group, a pentadecyl group, a heptadecyl group and an octadecyl group, and more preferable examples thereof include a methyl group, an ethyl group, a propyl group, an isopropyl group, a butyl group, a sec-butyl group, a tert-butyl group, a pentyl group, a hexyl group, an octyl group and a 2-ethylhexyl group.

The saturated cyclic hydrocarbon group may be monocyclic or polycyclic. Preferable examples thereof include a cycloalkyl group such as a cyclopentyl group, a cyclohexyl group, a methylcyclohexyl group, a dimethylcyclohexyl group, a cycloheptyl group and a cyclooctyl group, a group obtained by hydrogenating a condensed aromatic hydrocarbon group such as a hydronaphthyl group, a bridged cyclic hydrocarbon group such as an adamantyl group, a norbornyl group and a methylnorbornyl group, and the following groups.

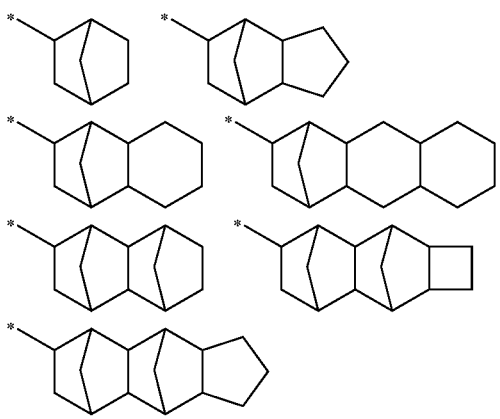

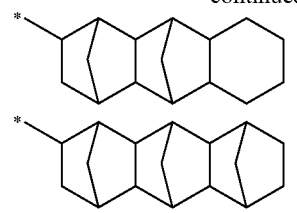

Among them, preferred are a cyclopropyl group, a cyclobutyl group, a cyclopentyl group, a cyclohexyl group, a cyclodecyl group, a 2-alkyl-2-adamantyl group, a 1-(1-adamantyl)alkan-1-yl group and an isobornyl group.

Preferable examples of the aromatic group include an aryl group such as a phenyl group, a naphthyl group, an anthryl group, a 4-methylphenyl group, a 4-ethylphenyl group, a 4-tert-butylphenyl group, a 4-cyclohexylphenyl group, a 4-methoxyphenyl group, a p-adamantylphenyl group, a tolyl group, a xylyl group, a cumyl group, a mesityl group, a biphenyl group, a phenanthryl group, a 2,6-diethylphenyl group and a 2-methyl-6-ethylphenyl group, and a phenyl group, a 4-methylphenyl group, a 4-ethylphenyl group, a 4-tert-butylphenyl group, a 4-cyclohexylphenyl group, a 4-methoxyphenyl group, a biphenyl group and a naphthyl group are more preferable.

Examples of the C1-C12 alkoxy group include a methoxy group, an ethoxy group, a propoxy group, a butoxy group, a pentyloxy group, a hexyloxy group, a heptyloxy group, an octyloxy group, a decyloxy group and a dodecyloxy group. Examples of the halogen atom include a fluorine atom, a chlorine atom, a bromine atom and an iodine atom. Examples of the C2-C4 acyl group include an acetyl group, a propyonyl group and a butyryl group.

Examples of the C3-C12 divalent acyclic hydrocarbon group formed by bonding $R^{b9}$ and $R^{b10}$ include a trimethylene group, a tetramethylene group and a pentamethylene group. Examples of the ring group formed together with the adjacent S+ and the divalent acyclic hydrocarbon group include a thiolan-1-ium ring (tetrahydrothiphenium ring), a thian-1-ium ring and a 1,4-oxathian-4-ium ring. A C3-C7 divalent acyclic hydrocarbon group is preferable.

Examples of the C1-C10 divalent acyclic hydrocarbon group formed by bonding $R^{b11}$ and $R^{b12}$ include a methylene group, an ethylene group, a trimethylene group, a tetramethylene group and a pentamethylene group and examples of the ring group include the followings.

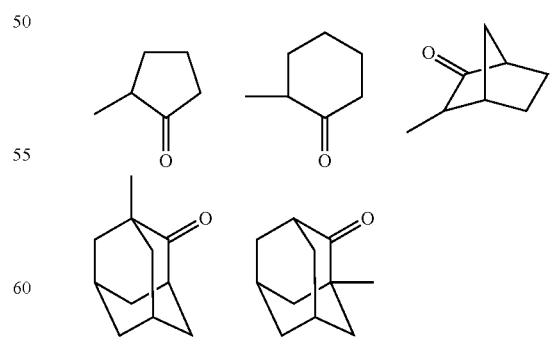

A C1-C5 divalent acyclic hydrocarbon group is preferable.

Examples of the C2-C13 acyloxy group include an acetyloxy group, a propyonyloxy group, a butyryloxy group, an isopropylcarbonyloxy group, a butylcarbonyloxy group, a sec-butylcarbonyloxy group, a tert-butylcarbonyloxy group, a pentylcarbonyloxy group, a hexylcarbonyloxy group, an octylcarbonyloxy group and a 2-ethylhexylcarbonyloxy group.

Examples of the cations represented by the formulae (b2-1) to (b2-4) include those described in JP 2010-204646 A.

Among the above-mentioned cations, preferred is the cation represented by the formula (b2-1), and more preferred is the cation represented by the formula (b2-1-1). A triphenylsulfonium cation and a trytolysulfonium cation are especially preferable.

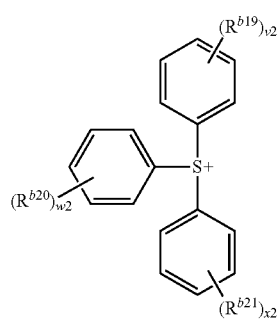

(b2-1-1)

wherein $R^{b19}$, $R^{b20}$ and $R^{b21}$ are independently in each occurrence a halogen atom (preferably a fluorine atom), a hydroxyl group, a C1-C18 aliphatic hydrocarbon group or a C1-C12 alkoxy group, and one or more hydrogen atoms of the aliphatic hydrocarbon group can be replaced by a hydroxyl group, a C1-C12 alkoxy group or a C6-C18 aromatic hydrocarbon group, and one or more hydrogen atoms of the saturated cyclic hydrocarbon group can be replaced by a halogen atom, a glycidyloxy group or a C2-C4 acyl group, and v2, w2 and x2 independently each represent an integer of 0 to 5.

The aliphatic hydrocarbon group has preferably 1 to 12 carbon atoms, and a C1-C12 alkyl group and a C4-C18 alicyclic hydrocarbon group are preferable, and v2, w2 and x2 independently each preferably represent 0 or 1.

It is preferred that $R^{b19}$, $R^{b20}$ and $R^{b21}$ are independently in each occurrence a halogen atom, a hydroxyl group, a C1-C12 alkyl group or a C1-C12 alkoxy group, and v2, w2 and x2 independently each represent an integer of 0 to 5. It is more preferred that $R^{b19}$, $R^{b20}$ and $R^{b21}$ are independently in each occurrence a fluorine atom, a hydroxyl group, a C1-C12 alkyl group or a C1-C12 alkoxy group, and v2, w2 and x2 independently each represent 0 or 1.

Examples of the cation represented by the formula (b2-1) include the following.

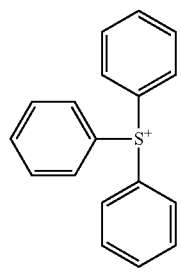

(b2-c-1)

(b2-c-2)

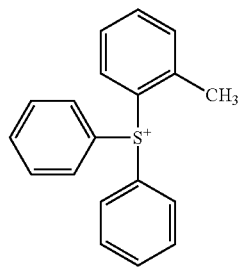

(b2-c-3)

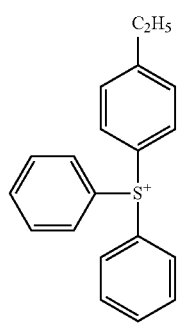

(b2-c-4)

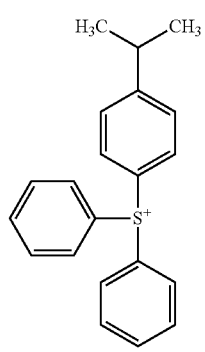

(b2-c-5)

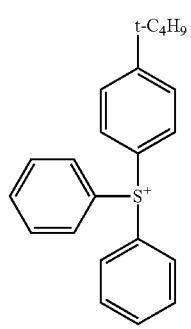

(b2-c-6)

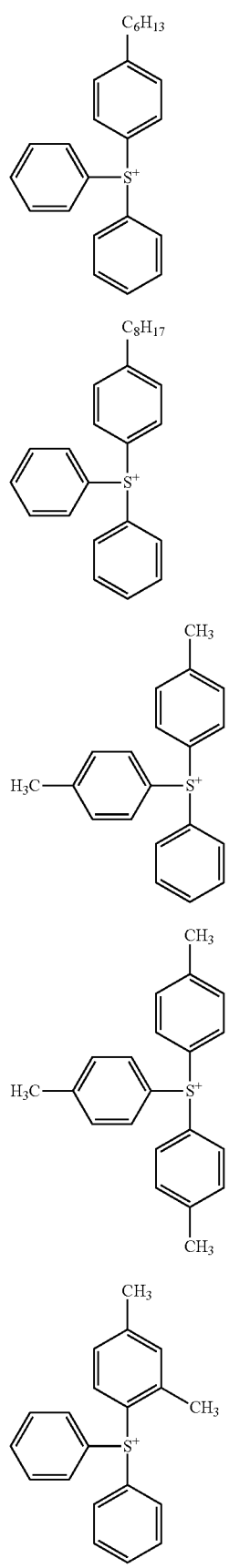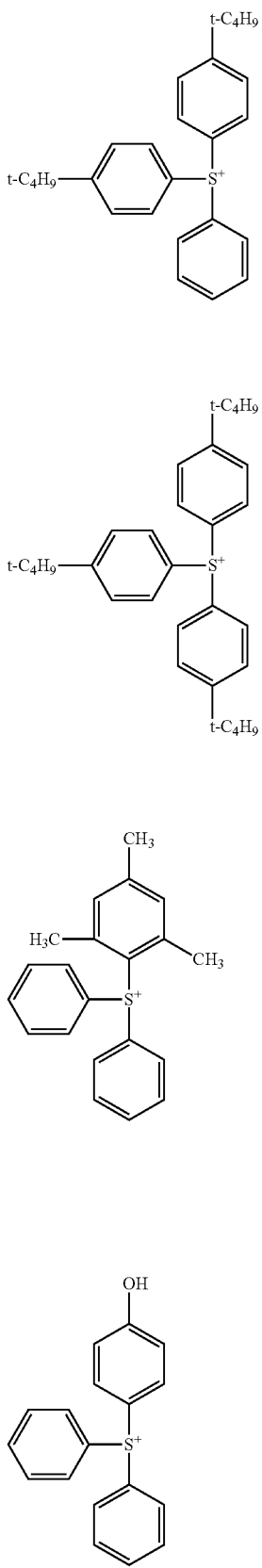

(b2-c-16)
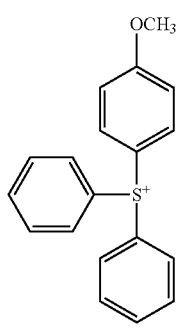

(b2-c-17)
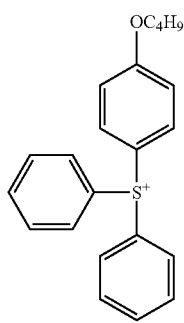

(b2-c-18)
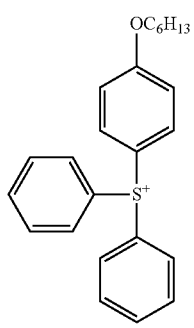

(b2-c-18)
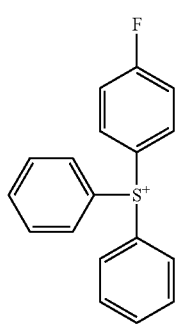

(b2-c-19)
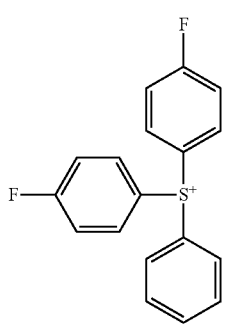

(b2-c-20)
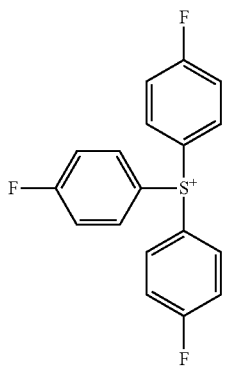

Examples of the cation represented by the formula (b2-3) include the followings.

(b2-c-21)
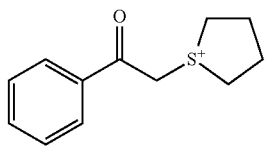

(b2-c-22)
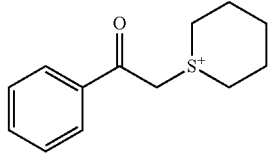

(b2-c-23)
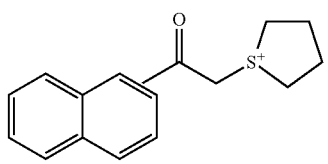

(b2-c-24)
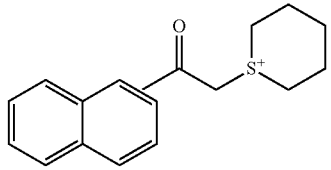

Examples of the salt represented by the formula (B1) include a salt wherein the anion is any one of the above-mentioned anions and the cation is any one of organic cations. Preferable examples thereof include those described in the following Table 1.

TABLE 1

| Salt represented by the formula (B1) | Anion | Cation |
|---|---|---|
| B1-1P | b1-s-2 | b2-c-1 |
| B1-2P | b1-s-2 | b2-c-21 |
| B1-3P | b1-s-11 | b2-c-1 |
| B1-4P | b1-s-11 | b2-c-2 |
| B1-5P | b1-s-11 | b2-c-6 |
| B1-6P | b1-s-11 | b2-c-10 |
| B1-7P | b1-s-11 | b2-c-12 |
| B1-8P | b1-s-11 | b2-c-15 |

TABLE 1-continued

| Salt represented by the formula (B1) | Anion | Cation |
|---|---|---|
| B1-9P | b1-s-11 | b2-c-21 |
| B1-10P | b1-s-11 | b2-c-23 |
| B1-11P | b1-s-14 | b2-c-1 |
| B1-12P | b1-s-14 | b2-c-2 |
| B1-13P | b1-s-14 | b2-c-6 |
| B1-14P | b1-s-14 | b2-c-10 |
| B1-15P | b1-s-14 | b2-c-12 |
| B1-16P | b1-s-14 | b2-c-15 |
| B1-17P | b1-s-14 | b2-c-21 |
| B1-18P | b1-s-14 | b2-c-23 |
| B1-19P | b1-s-20 | b2-c-1 |
| B1-20P | b1-s-20 | b2-c-2 |
| B1-21P | b1-s-20 | b2-c-6 |
| B1-22P | b1-s-20 | b2-c-10 |
| B1-23P | b1-s-20 | b2-c-12 |
| B1-24P | b1-s-20 | b2-c-15 |
| B1-25P | b1-s-20 | b2-c-21 |
| B1-26P | b1-s-20 | b2-c-23 |
| B1-27P | b1-s-4 | b2-c-1 |
| B1-28P | b1-s-35 | b2-c-1 |
| B1-29P | b1-s-36 | b2-c-1 |
| B1-30P | b1-s-39 | b2-c-1 |
| B1-31P | b1-s-40 | b2-c-1 |
| B1-32P | b1-s-41 | b2-c-1 |
| B1-33P | b1-s-42 | b2-c-1 |

Preferable examples of the acid generator include salts represented by the formulae (B1-1) to (B1-17), the salt containing a triphenylsulfonium cation or a tritolysulfonium cation is more preferable, and the salts represented by the formulae (B1-2), (B1-3), (B1-6), (B1-7), (B1-11), (B1-12), (B1-13) and (B1-14) are especially preferable.

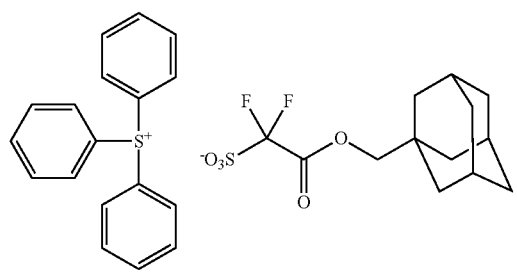
(B1-1)

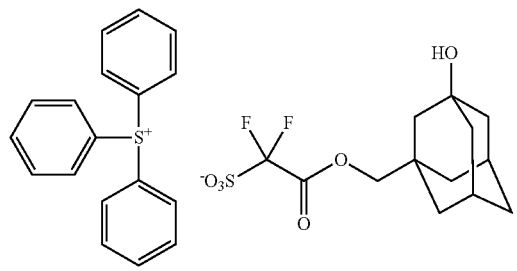
(B1-2)

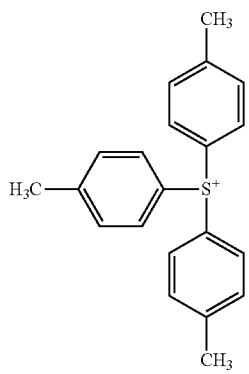
(B1-3)

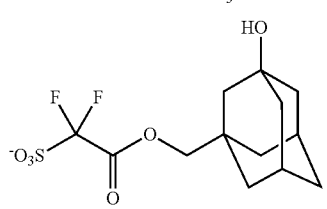
(B1-4)

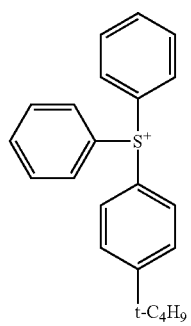
(B1-5)

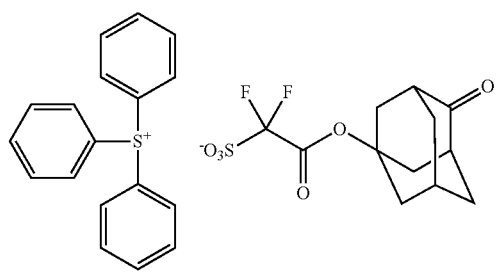
(B1-6)

(B1-7)
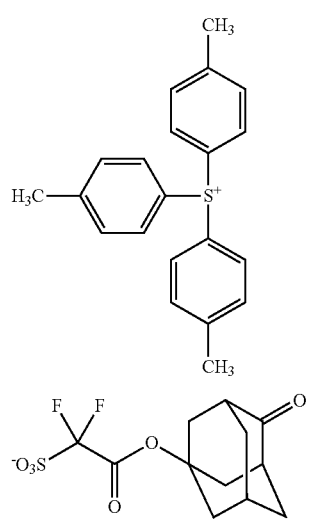
(B1-8)
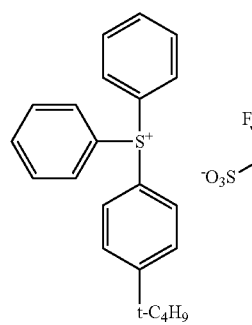
(B1-9)
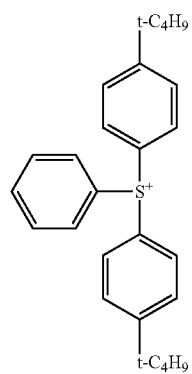
(B1-10)
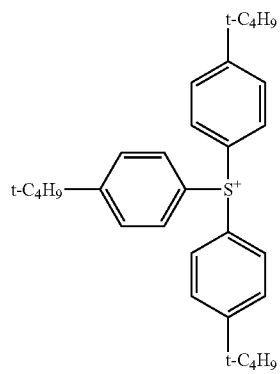
(B1-11)
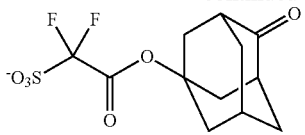
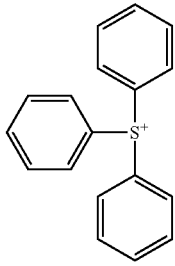
(B1-12)
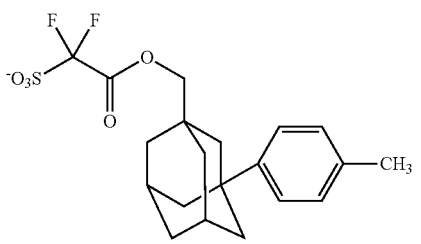
(B1-13)
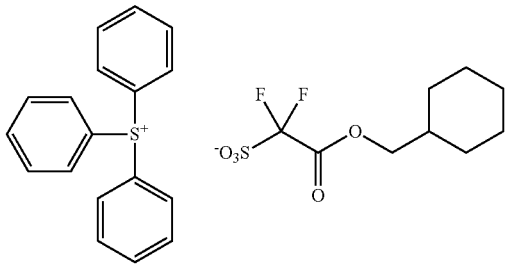
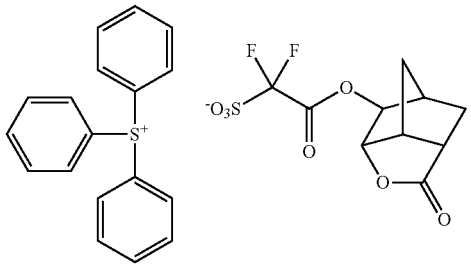
(B1-14)
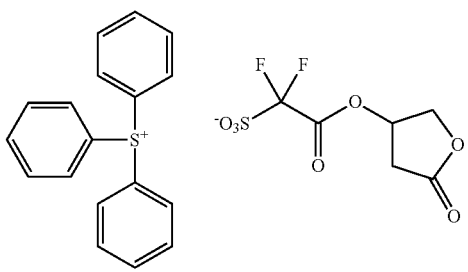

(B1-15)

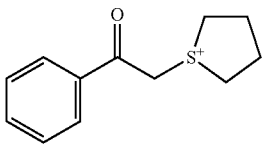

(B1-16)

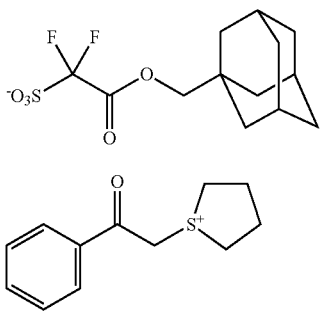

(B1-17)

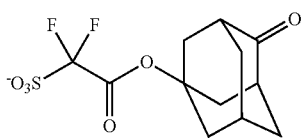

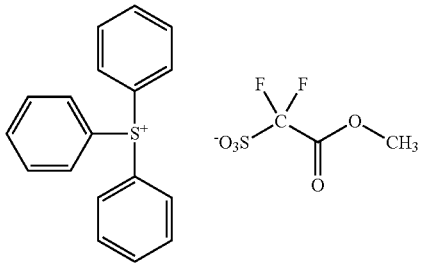

When the acid generator contains the acid generator other than the salt represented by the formula (B1), the content of the salt represented by the formula (B1) in the acid generator is preferably 70% by mass or more and more preferably 90% by mass or more based on the total amount of the acid generator. The acid generator preferably consists of the salt represented by the formula (B1).

The content of the acid generator is usually 1 part by mass or more per 100 parts by mass of RESIN (A), and preferably 3 parts by mass or more. The content of the acid generator is usually 40 parts by mass or less per 100 parts by mass of RESIN (A), and preferably 35 parts by mass or less.

The photoresist compositions of the present invention can contain a basic compound as a quencher. The basic compound has the property that it can trap an acid, especially an acid generated from the acid generator by applying a radiation.

The basic compound is preferably a basic nitrogen-containing organic compound, and examples thereof include an amine compound such as an aliphatic amine and an aromatic amine and an ammonium salt. Examples of the aliphatic amine include a primary amine, a secondary amine and a tertiary amine. Examples of the aromatic amine include an aromatic amine in which aromatic ring has one or more amino groups such as aniline and a heteroaromatic amine such as pyridine. Preferable examples thereof include an aromatic amine represented by the formula (C2):

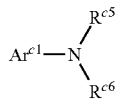

(C2)

wherein $Ar^{c1}$ represents an aromatic hydrocarbon group, and $R^{c5}$ and $R^{c6}$ independently represent a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group.

The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms.

As the aromatic amine represented by the formula (C2), an amine represented by the formula (C2-1):

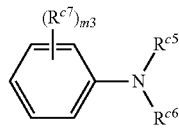

(C2-1)

wherein $R^{c5}$ and $R^{c6}$ are the same as defined above, and $R^{c7}$ is independently in each occurrence an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, and m3 represents an integer of 0 to 3, is preferable. The aliphatic hydrocarbon group is preferably an alkyl group and the saturated cyclic hydrocarbon group is preferably a cycloalkyl group. The aliphatic hydrocarbon group preferably has 1 to 6 carbon atoms. The saturated cyclic hydrocarbon group preferably has 5 to 10 carbon atoms. The aromatic hydrocarbon group preferably has 6 to 10 carbon atoms. The alkoxy group preferably has 1 to 6 carbon atoms.

Examples of the aromatic amine represented by the formula (C2) include 1-naphthylamine, 2-naphthylamine, aniline, diisopropylaniline, 2-methylaniline, 3-methylaniline, 4-methylaniline, 4-nitroaniline, N-methylaniline, N,N-dimethylaniline, and diphenylamine, and among them, preferred is diisopropylaniline and more preferred is 2,6-diisopropylaniline.

Other examples of the basic compound include amines represented by the formulae (C3) to (C11):

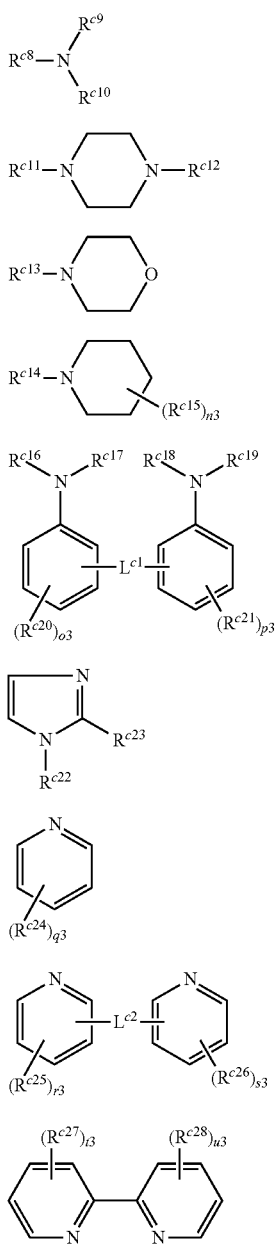

wherein $R^{c8}$, $R^{c20}$, $R^{c21}$, and $R^{c23}$ to $R^{c28}$ independently represent an aliphatic hydrocarbon group, an alkoxy group, a saturated cyclic hydrocarbon group or an aromatic hydrocarbon group, and the aliphatic hydrocarbon group, the alkoxy group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c9}$, $R^{c10}$, $R^{c11}$ to $R^{c14}$, $R^{c16}$ to $R^{c19}$, and $R^{c22}$ independently represents a hydrogen atom, an aliphatic hydrocarbon group, a saturated cyclic hydrocarbon group or an aromatic hydrocarbon group, and the aliphatic hydrocarbon group, the saturated cyclic hydrocarbon group and the aromatic hydrocarbon group can have one or more substituents selected from the group consisting of a hydroxyl group, an amino group, an amino group having one or two C1-C4 alkyl groups and a C1-C6 alkoxy group, $R^{c15}$ is independently in each occurrence an aliphatic hydrocarbon group, a saturated cyclic hydrocarbon group or an alkanoyl group, $L^{c1}$ and $L^{c2}$ independently represents a divalent aliphatic hydrocarbon group, —CO—, —C(=NH)—, —C(=NR$^{c3}$)—, —S—, —S—S— or a combination thereof and $R^{c3}$ represents a C1-C4 alkyl group, O3 to u3 each independently represents an integer of 0 to 3 and n3 represents an integer of 0 to 8.

The aliphatic hydrocarbon group has preferably 1 to 6 carbon atoms, and the saturated cyclic hydrocarbon group has preferably 3 to 6 carbon atoms, and the alkanoyl group has preferably 2 to 6 carbon atoms, and the divalent aliphatic hydrocarbon group has preferably 1 to 6 carbon atoms. The divalent aliphatic hydrocarbon group is preferably an alkylene group.

Examples of the amine represented by the formula (C3) include hexylamine, heptylamine, octylamine, nonylamine, decylamine, dibutylamine, dipentylamine, dihexylamine, diheptylamine, dioctylamine, dinonylamine, didecylamine, triethylamine, trimethylamine, tripropylamine, tributylamine, tripentylamine, trihexylamine, triheptylamine, trioctylamine, trinonylamine, tridecylamine, methyldibutylamine, methyldiheptylamine, methyldihexylamine, methyldicyclohexylamine, methyldiheptylamine, methyldioctylamine, methyldinonylamine, methyldidecylamine, ethyldibutylamine, ethydipentylamine, ethyldihexylamine, ethydiheptylamine, ethyldioctylamine, ethyldinonylamine, ethyldidecylamine, dicyclohexylmethylamine, tris[2-(2-methoxyethoxy)ethyl]amine, triisopropanolamine, ethylenediamine, tetramethylenediamine, hexamethylenediamine, 4,4'-diamino-1,2-diphenylethane, 4,4'-diamino-3,3'-dimethyldiphenylmethane and 4,4'-diamino-3,3'-diethyldiphenylmethane.

Examples of the amine represented by the formula (C4) include piperazine. Examples of the amine represented by the formula (C5) include morpholine. Examples of the amine represented by the formula (C6) include piperidine and hindered amine compounds having a piperidine skeleton as disclosed in JP 11-52575 A. Examples of the amine represented by the formula (C7) include 2,2'-methylenebisaniline. Examples of the amine represented by the formula (C8) include imidazole and 4-methylimidazole. Examples of the amine represented by the formula (C9) include pyridine and 4-methylpyridine. Examples of the amine represented by the formula (C10) include di-2-pyridyl ketone, 1,2-di(2-pyridyl)ethane, 1,2-di(4-pyridyl)ethane, 1,3-di(4-pyridyl)propane, 1,2-bis(2-pyridyl)ethene, 1,2-bis(4-pyridyl)ethene, 1,2-di(4-pyridyloxy)ethane, 4,4'-dipyridyl sulfide, 4,4'-dipyridyl disulfide, 2,2'-dipyridylamine and 2,2'-dipicolylamine. Examples of the amine represented by the formula (C11) include bipyridine.

Examples of the quaternary ammonium hydroxide include tetramethylammonium hydroxide, tetrabutylammonium hydroxide, tetrahexylammonium hydroxide, tetraoctylammonium hydroxide, phenyltrimethylammonium hydroxide, (3-trifluoromethylphenyl)trimethylammonium hydroxide and (2-hydroxyethyl)trimethylammonium hydroxide (so-called "choline").

When the photoresist compositions contain the basic compound, the content thereof is usually 0.01 to 1% by mass based on sum of solid component.

The photoresist compositions of the present invention usually contain one or more solvents. Examples of the solvent include a glycol ether ester such as ethyl cellosolve acetate, methyl cellosolve acetate and propylene glycol monomethyl ether acetate; a glycol ether such as propylene glycol monomethyl ether; an acyclic ester such as ethyl lactate, butyl acetate, amyl acetate and ethyl pyruvate; a ketone such as acetone, methyl isobutyl ketone, 2-heptanone and cyclohexanone; and a cyclic ester such as γ-butyrolactone.

The amount of the solvent is usually 90% by mass or more, preferably 92% by mass or more preferably 94% by mass or more based on total amount of the photoresist composition of the present invention. The amount of the solvent is usually 99.9% by mass or less and preferably 99% by mass or less based on total amount of the photoresist composition of the present invention.

The photoresist compositions of the present invention can contain, if necessary, a small amount of various additives such as a sensitizer, a dissolution inhibitor, other polymers, a surfactant, a stabilizer and a dye as long as the effect of the present invention is not prevented.

The photoresist compositions of the present invention are useful for a chemically amplified photoresist composition.

A photoresist pattern can be produced by the following steps (1) to (5):
 (1) a step of applying the first or second photoresist composition of the present invention on a substrate,
 (2) a step of forming a photoresist film by conducting drying,
 (3) a step of exposing the photoresist film to radiation,
 (4) a step of baking the exposed photoresist film, and
 (5) a step of developing the baked photoresist film with an alkaline developer, thereby forming a photoresist pattern.

The applying of the photoresist composition on a substrate is usually conducted using a conventional apparatus such as spin coater. The photoresist composition is preferably filtrated with filter having a pore size of 0.01 to 0.2 μm before applying. Examples of the substrate include a silicon wafer or a quartz wafer on which a sensor, a circuit, a transistor or the like is formed.

The formation of the photoresist film is usually conducted using a heating apparatus such as hot plate or a decompressor, and the heating temperature is usually 50 to 200° C., and the operation pressure is usually 1 to $1.0*10^5$ Pa.

The photoresist film obtained is exposed to radiation using an exposure system. The exposure is usually conducted through a mask having a pattern corresponding to the desired photoresist pattern. Examples of the exposure source include a light source radiating laser light in a UV-region such as a KrF excimer laser (wavelength: 248 nm), an ArF excimer laser (wavelength: 193 nm) and a $F_2$ laser (wavelength: 157 nm), and a light source radiating harmonic laser light in a far UV region or a vacuum UV region by wavelength conversion of laser light from a solid laser light source (such as YAG or semiconductor laser).

The temperature of baking of the exposed photoresist film is usually 50 to 200° C., and preferably 70 to 150° C.

The development of the baked photoresist film is usually carried out using a development apparatus. The alkaline developer used may be any one of various alkaline aqueous solution used in the art. Generally, an aqueous solution of tetramethylammonium hydroxide or (2-hydroxyethyl)trimethylammonium hydroxide (commonly known as "choline") is often used. After development, the photoresist pattern formed is preferably washed with ultrapure water, and the remained water on the photoresist pattern and the substrate is preferably removed.

The photoresist composition of the present invention provides a photoresist pattern showing good CD uniformity, and therefore, the photoresist composition of the present invention is suitable for ArF excimer laser lithography, KrF excimer laser lithography, ArF immersion lithography, EUV (extreme ultraviolet) lithography, EUV immersion lithography and EB (electron beam) lithography. Further, the photoresist composition of the present invention can especially be used for EUV lithography and EB lithography.

EXAMPLES

The present invention will be described more specifically by Examples, which are not construed to limit the scope of the present invention.

The "%" and "part(s)" used to represent the content of any component and the amount of any material used in the following examples and comparative examples are on amass basis unless otherwise specifically noted. The weight-average molecular weight of any material used in the following examples is a value found by gel permeation chromatography [Column: Three of TSKgel Multipore HXL-M with guard column, manufactured by TOSOH CORPORATION, Solvent: tetrahydrofuran, Flow rate: 1.0 mL/min., Detector: RI Detector, Column temperature: 40° C., Injection volume: 100 μL] using standard polystyrene as a standard reference material. The ratio of the structural units in the resin was decided by measuring the amounts of the unreacted monomers in the reaction after polymerization followed by calculating the amount of the reacted monomers from the result measured.

Example 1

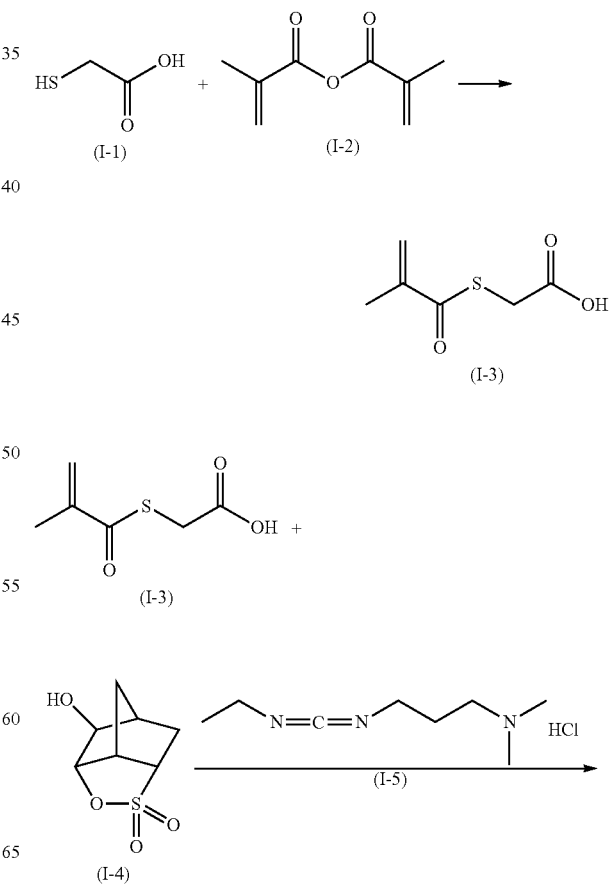

-continued

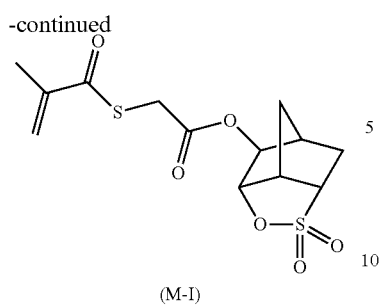

(M-I)

Into a reactor, added were 25.00 parts of the compound represented by the formula (I-1), 57.79 parts of triethylamine, 0.03 part of dimethylaminopyridine and 250 parts of acetonitrile. The resultant mixture was stirred at 23° C. for 30 minutes, and then, cooled down to 2° C. To the mixture, 51.00 parts of the compound represented by the formula (I-2) was added dropwise thereto over 30 minutes with keeping at 5° C. or less. The resultant mixture was stirred at 2° C. for 30 minutes, and further stirred at 23° C. for 1 hour. The reaction mixture obtained was mixed with 25 parts of ion-exchanged water to concentrate. To the residue obtained, 250 parts of chloroform and 125 parts of ion-exchanged water were added followed by conducting washing of the organic layer three times. The organic layer obtained was concentrated to obtain 3.58 parts of the compound represented by the formula (I-3).

Into a reactor, added were 3.00 parts of the compound represented by the formula (I-4), 4.73 parts of the compound represented by the formula (I-5), 0.003 part of dimethylaminopyridine and 30 parts of tetrahydrofuran. The resultant mixture was stirred at 23° C. for 30 minutes, and then, cooled down to 2° C. To the mixture, 2.76 parts of the compound represented by the formula (I-3) and 13.78 parts of tetrahydrofuran were added dropwise thereto over 30 minutes with keeping at 5° C. or less. The resultant mixture was stirred at 2° C. for 1 hour, and further stirred at 23° C. for 20 hours. The reaction mixture obtained was mixed with 15 parts of ion-exchanged water to concentrate. To the residue obtained, 30 parts of ethyl acetate was added followed by conducting extraction. The organic layer obtained was washed with 30 parts of ion-exchanged water. The organic layer was washed with 30 parts of 10% potassium carbonate solution at 23° C. The organic layer was washed with 30 parts of 1N hydrochloric acid at 23° C. the organic layer obtained was concentrated to obtain 2.78 parts of the compound represented by the formula (M-I).

MS: 332.0 (molecular ion peak)

Monomers used in the following Examples are following monomers (M-A), (M-B), (M-C), (M-D), (M-E), (M-F), (M-G), (M-H), (M-I) and (M-J).

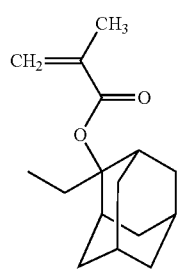

(M-A)

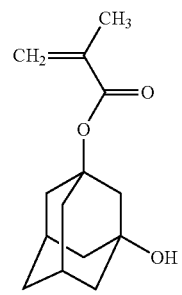

(M-B)

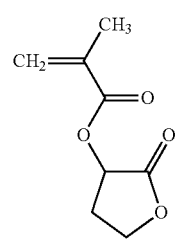

(M-C)

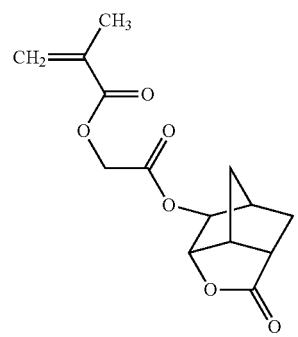

(M-D)

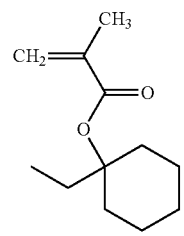

(M-E)

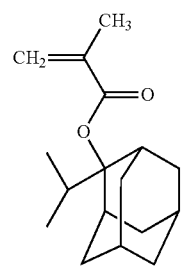

(M-F)

(M-G)
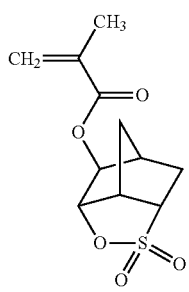

(M-H)
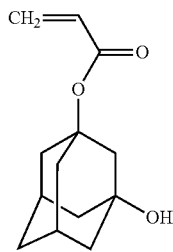

(M-I)
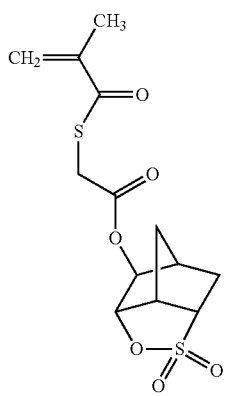

(M-J)
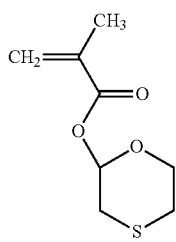

Example 2

The monomers (M-A), (M-E), (M-B), (M-C) and (M-I) were mixed in a molar ratio of 32/7/8/43/10 (monomer (M-A)/monomer (M-E)/monomer (M-B)/monomer (M-C)/ monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis (2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $8.4 \times 10^3$ was obtained in a yield of 84%. This resin is called as resin A1. Resin A1 had the following structural units, and the molar ratio of the structural units ((u-A)/(u-E)/(u-B)/(u-C)/(u-I)) was 26.6/7.2/8.7/46.9/10.6.

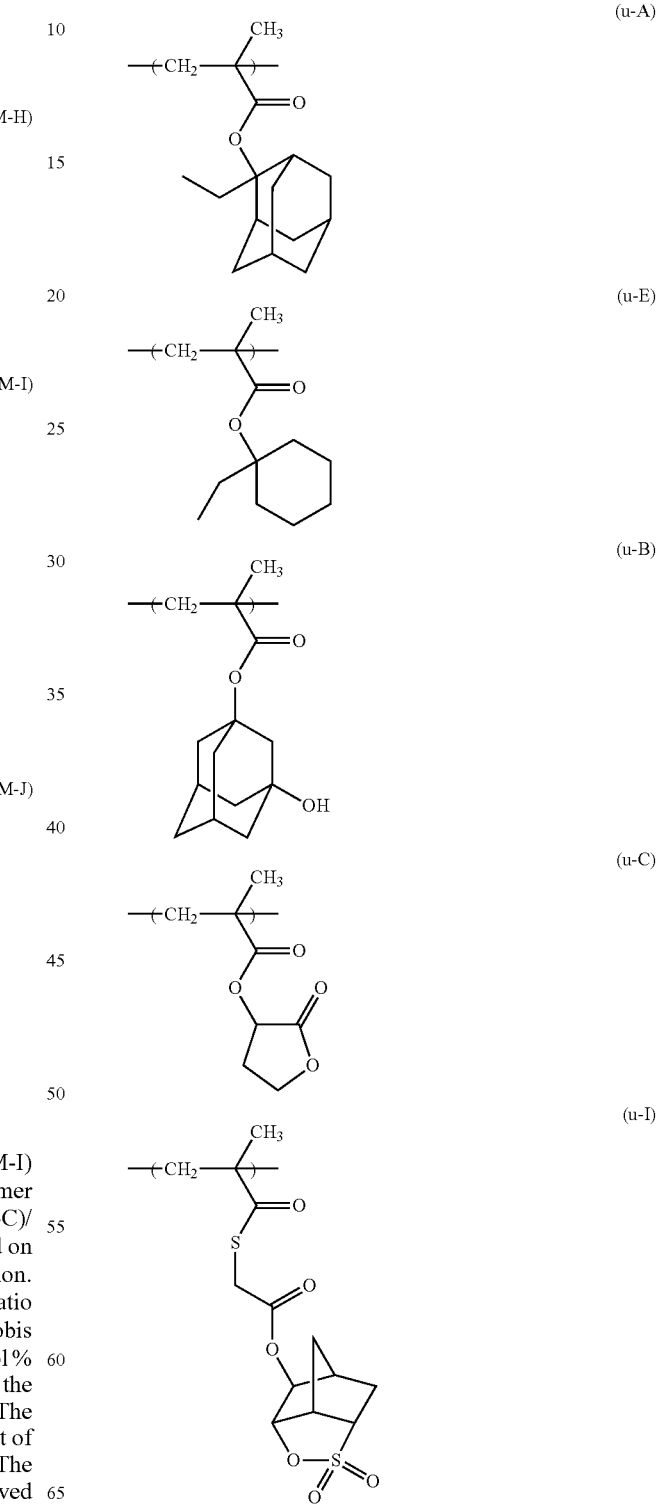

Example 3

The monomers (M-F), (M-E), (M-B), (M-C) and (M-I) were mixed in a molar ratio of 35/10/6/37/12 (monomer (M-F)/monomer (M-E)/monomer (M-B)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $8.1 \times 10^3$ was obtained in a yield of 80%. This resin is called as resin A2. Resin A2 had the following structural units, and the molar ratio of the structural units ((u-F)/(u-E)/(u-B)/(u-C)/(u-I)) was 27.5/10.2/7.0/42.3/13.0.

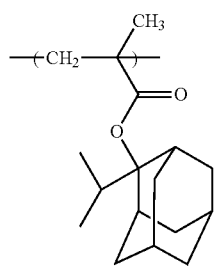
(u-F)

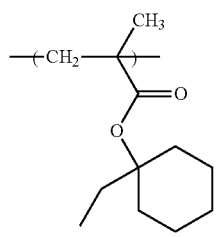
(u-E)

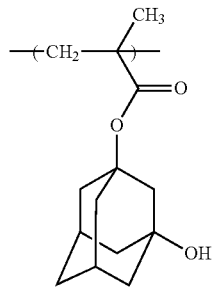
(u-B)

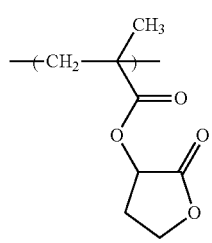
(u-C)

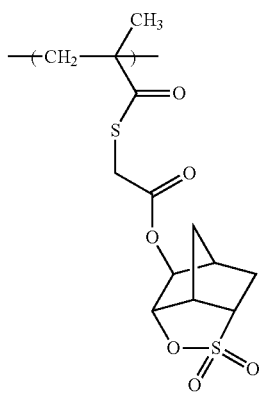
(u-I)

Example 4

The monomers (M-A), (M-E), (M-B), (M-D), (M-C) and (M-I) were mixed in a molar ratio of 32/7/8/10/33/10 (monomer (M-A)/monomer (M-E)/monomer (M-B)/monomer (M-D)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $7.8 \times 10^3$ was obtained in a yield of 75%. This resin is called as resin A3. Resin A3 had the following structural units, and the molar ratio of the structural units ((u-A)/(u-E)/(u-B)/(u-D)/(u-C)/(u-I)) was 26.5/7.2/8.7/11.2/35.8/10.6.

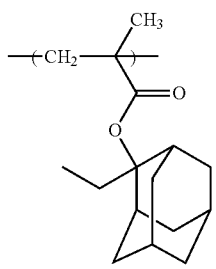
(u-A)

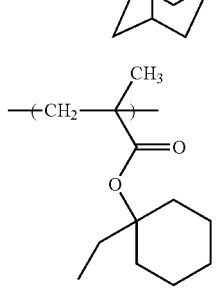
(u-E)

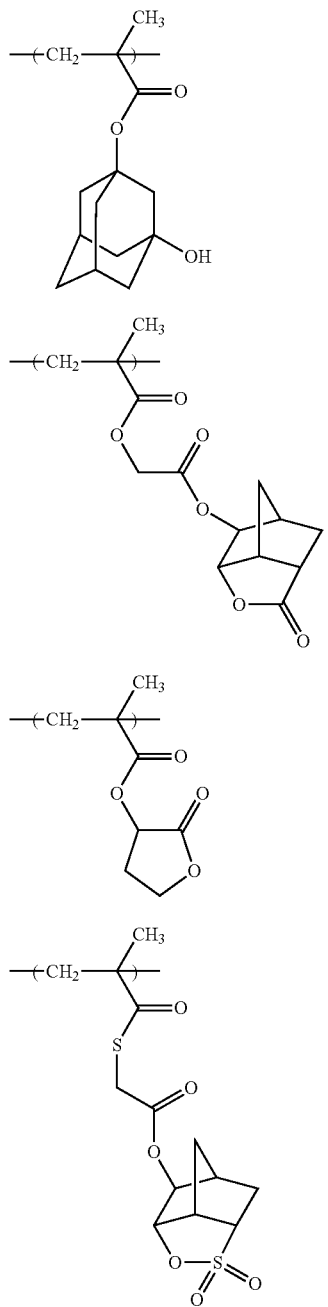

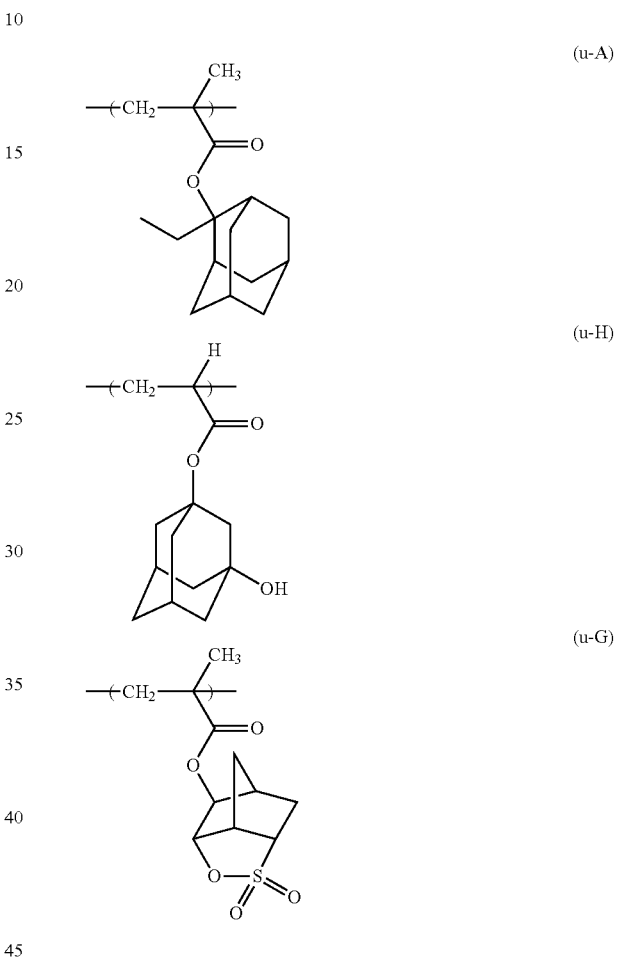

in 1,4-dioxane followed by poured the resultant solution into a large amount of a mixture of methanol and water to cause precipitation. This operation was repeated twice for purification. As a result, a resin having a weight-average molecular weight of about $7.3 \times 10^3$ was obtained in a yield of 68%. This resin is called as resin A5. Resin A5 had the following structural units, and the molar ratio of the structural units ((u-A)/(u-H)/(u-G)) was 43.0/16.1/40.9.

Example 5

The monomers (M-F), (M-J), (M-B), (M-D), (M-C) and (M-I) were mixed in a molar ratio of 30/14/6/10/30/10 (monomer (M-F)/monomer (M-J)/monomer (M-B)/monomer (M-D)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $8.1 \times 10^3$ was obtained in a yield of 65%. This resin is Resin Synthesis Example 1

The monomers (M-A), (M-H) and (M-G) were mixed in a molar ratio of 52.6/15.8/31.6 (monomer (M-A)/monomer (M-H)/monomer (M-G)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 78° C. for about 5 hours. The reaction mixture obtained was poured into a large amount of a mixture of methanol and water to cause precipitation. The precipitate was collected by filtration and then, was dissolved called as resin A5. Resin A5 had the following structural units, and the molar ratio of the structural units ((u-F)/(u-J)/(u-B)/(u-D)/(u-C)/(u-I)) was 21.4/13.3/6.7/12.4/35.6/10.6.

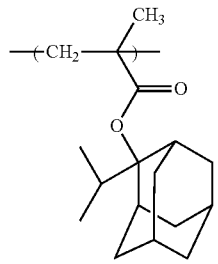
(u-F)

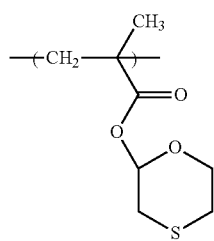
(u-J)

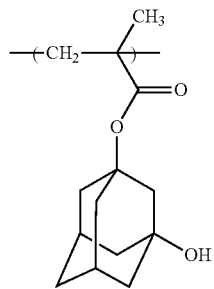
(u-B)

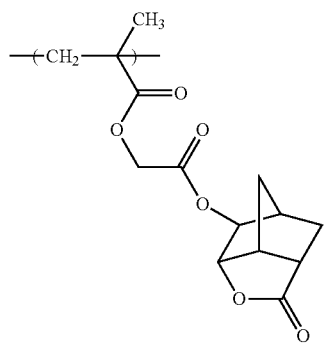
(u-D)

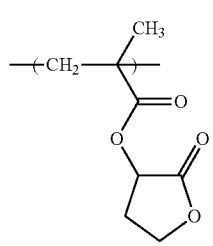
(u-C)

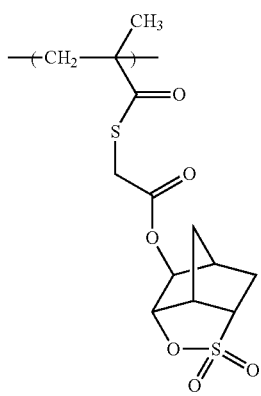
(u-I)

Example 6

The monomers (M-F), (M-E), (M-B), (M-D), (M-C) and (M-I) were mixed in a molar ratio of 30/14/6/10/30/10 (monomer (M-F)/monomer (M-E)/monomer (M-B)/monomer (M-D)/monomer (M-C)/monomer (M-I)), and 1,4-dioxane in 1.5 times part based on total parts of all monomers was added to prepare a solution. To the solution, azobisisobutyronitrile as an initiator in a ratio of 1 mol % based on all monomer molar amount and azobis(2,4-dimethylvaleronitrile) as an initiator in a ratio of 3 mol % based on all monomer molar amount were added, and the obtained mixture was heated at 73° C. for about 5 hours. The reaction mixture obtained was poured into a large amount of a mixture of methanol and water to cause precipitation. The precipitate was collected by filtration and then, was dissolved in 1,4-dioxane followed by poured the resultant solution into a large amount of a mixture of methanol and water to cause precipitation. This operation was repeated twice for purification. As a result, a resin having a weight-average molecular weight of about $8.0 \times 10^3$ was obtained in a yield of 66%. This resin is called as resin A6. Resin A6 had the following structural units, and the molar ratio of the structural units ((u-F)/(u-E)/(u-B)/(u-D)/(u-C)/(u-I)) was 21.4/13.8/6.5/12.3/35.4/10.6.

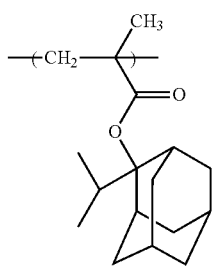
(u-F)

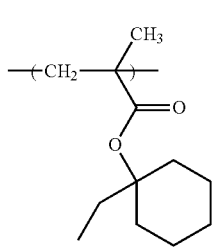
(u-E)

-continued (u-B)
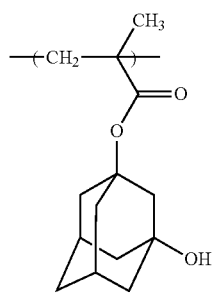

(u-D)
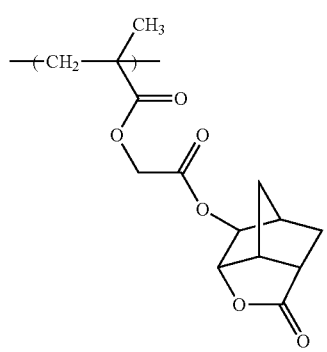

(u-C)
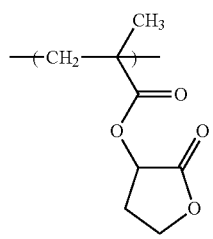

(u-I)
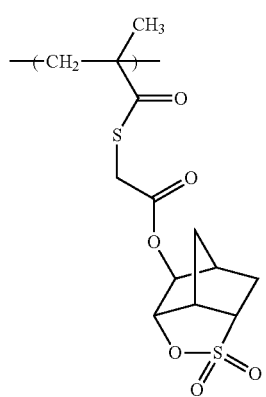

Examples 7 to 12 and Comparative Example 1

Resin

Resin A1, A2, A3, A4, A5, A6

<Acid Generator>

B1:

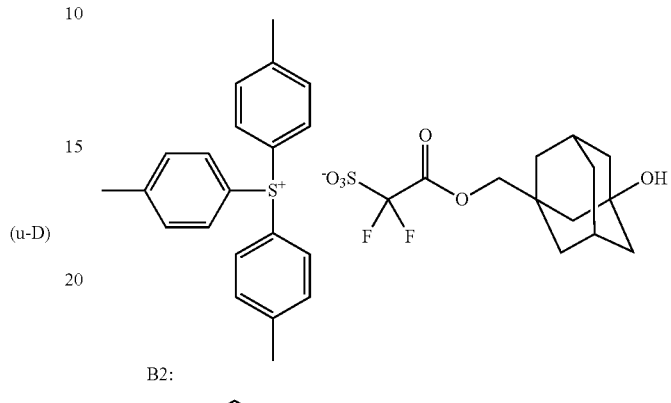

B2:

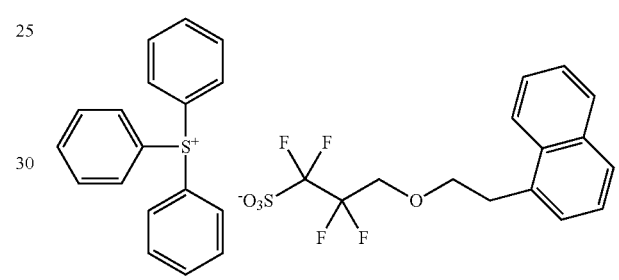

<Quencher>
C1: 2,6-diisopropylaniline
<Solvent>

| E1: | propylene glycol monomethyl ether acetate | 265 parts |
| | propylene glycol monomethyl ether | 20 parts |
| | 2-heptanone | 20 parts |
| | γ-butyrolactone | 3.5 parts |

The following components were mixed and dissolved, further, filtrated through a fluorine resin filter having pore diameter of 0.2 μm, to prepare photoresist compositions.

Resin (kind and amount are described in Table 2)
Acid generator (kind and amount are described in Table 2)
Quencher (kind and amount are described in Table 2)
Solvent E1

TABLE 2

| Ex. No. | Resin (kind/amount (part)) | Acid generator (kind/amount (part)) | Quencher (kind/amount (part)) | PB (°C.) | PEB (°C.) |
| --- | --- | --- | --- | --- | --- |
| Ex. 7 | A1/10 | B1/1.10 | C1/0.07 | 105 | 100 |
| Ex. 8 | A2/10 | B1/1.10 | C1/0.07 | 90 | 85 |
| Ex. 9 | A3/10 | B1/1.10 | C1/0.07 | 105 | 100 |
| Ex. 10 | A1/10 | B2/1.10 | C1/0.07 | 105 | 100 |
| Ex. 11 | A5/10 | B1/1.10 | C1/0.07 | 90 | 85 |
| Ex. 12 | A6/10 | B1/1.10 | C1/0.07 | 90 | 85 |
| Comp. Ex. 1 | A4/10 | B2/1.10 | C1/0.07 | 105 | 100 |

Silicon wafers (12 inches) were each coated with "ARC-29", which is an organic anti-reflective coating composition available from Nissan Chemical Industries, Ltd., and then baked at 205° C. for 60 seconds, to form a 780 Å-thick organic anti-reflective coating. Each of the photoresist compositions prepared as above was spin-coated over the anti-reflective coating so that the thickness of the resulting film became 85 nm after drying. The silicon wafers thus coated with the respective photoresist compositions were each prebaked on a direct hotplate at a temperature shown in the column "PB" in Table 2 for 60 seconds. Using an ArF excimer stepper for immersion exposure ("XT: 1900Gi" manufactured by ASML, NA-1.35, ¾ Annular, X—Y polarization), each wafer thus formed with the respective resist film was subjected to contact hole pattern exposure using a photomask for forming a contact hole pattern having 100 nm of a hole pitch and 40 nm of a hole diameter with the exposure quantity being varied stepwise. Ultrapure water was used as an immersion medium.

After the exposure, each wafer was subjected to post-exposure baking on a hotplate at a temperature shown in the column "PEB" in Table 2 for 60 seconds and then to paddle development for 60 seconds with an aqueous solution of 2.38% by mass tetramethylammonium hydroxide.

Each of patterns developed on the organic anti-reflective coating substrate after the development was observed with a scanning electron microscope, the results of which are shown in Table 3.

Effective sensitivity (ES): It was expressed as the amount of exposure that the hole diameter of the contact hole pattern became 55 nm after exposure and development.

CD uniformity (CDU): The photoresist patterns were obtained using a photomask for forming a contact hole pattern having a hole diameter of 70 nm and a hole pitch of 100 nm at the exposure amount of ES. Each of patterns developed on the organic anti-reflective coating substrate after the development was observed with a scanning electron microscope. The hole diameter of the contact hole patterns was twenty four times measured and its average diameter was calculated. The average diameters of four hundred holes on the same wafer were respectively measured. When population was the average diameters of four hundred holes, the standard deviation was calculated. Each of the standard deviations is shown in a column of "CDU" of Table 3. The smaller the standard deviation is, the better CDU the photoresist pattern shows, and the better pattern profile is.

TABLE 3

| Ex. No. | CDU |
|---|---|
| Ex. 7 | 1.78 |
| Ex. 8 | 1.72 |
| Ex. 9 | 1.71 |
| Ex. 10 | 1.88 |
| Ex. 11 | 1.68 |
| Ex. 12 | 1.69 |
| Comp. Ex. 1 | 2.45 |

The photoresist composition comprising the resin of the present invention provides a photoresist pattern having a good CD uniformity.

What is claimed is:

1. A resin comprising a structural unit represented by the formula (aa):

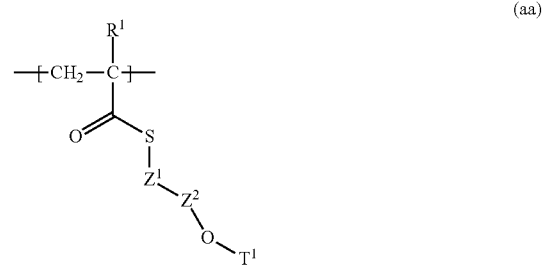

(aa)

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

$$-A^{10}-(X^{10}-A^{11})_s-X^{11}-A^{12}-$$  (a-1)

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—.

2. The resin according to claim 1, wherein total carbon number of $A^{10}$, $A^{11}$ and $A^{12}$ is 6 or less.

3. The resin according to claim 1, wherein $T^1$ is a polycyclic sultone ring group in the formula (aa).

4. The resin according to claim 1, wherein $T^1$ is a group represented by the formula (T1):

(T1)

wherein $Z^{12}$ represents —O—, —S— or —CH$_2$—, one or two hydrogen atoms in —CH$_2$— in the formula (T1) may be replaced by a halogen atom, a hydroxyl group, an oxo group, a cyano group, a C1-C12 alkyl group optionally having a halogen atom or a hydroxyl group, a C1-C12 alkoxy group, a C6-C12 aryl group, a C7-C12 aralkyl group, a glycidyloxy group, a C2-C12 alkoxycarbonyl group or a C2-C4 acyl group, and * represents a binding position to —O—, in the formula (aa).

5. The resin according to claim 1, wherein $Z^2$ is —CO— in the formula (aa).

6. The resin according to claim 1, wherein $Z^1$ is —CH$_2$— in the formula (aa).

7. The resin according to claim 1, wherein the resin is one being insoluble or poorly soluble in an aqueous alkali solution but becoming soluble in an aqueous alkali solution by the action of an acid.

8. A photoresist composition comprising the resin according to claim 7 and an acid generator.

9. The photoresist composition according to claim 8, which further comprises a solvent.

10. The photoresist composition according to claim 9, which further comprises a basic compound.

11. The photoresist composition according to claim 8, which further comprises a basic compound.

12. A process for producing a photoresist pattern comprising:
(1) a step of applying the photoresist composition according to claim 8, claim 9, claim 11 or claim 10 on a substrate to form a photoresist composition layer,
(2) a step of forming a photoresist film by drying the photoresist composition layer formed,
(3) a step of exposing the photoresist film to radiation,
(4) a step of heating the photoresist film after exposing, and
(5) a step of developing the photoresist film after heating.

13. A compound represented by the formula (aa'):

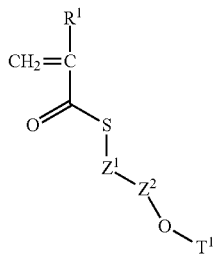
(aa')

wherein $R^1$ represents a C1-C6 alkyl group optionally having one or more halogen atoms, a hydrogen atom or a halogen atom, $T^1$ represents a C4-C34 sultone ring group optionally having one or more substituents, $Z^1$ represents a C1-C6 alkanediyl group optionally having one or more substituents, or a group represented by the formula (a-1):

$$-A^{10}\text{-}(X^{10}\text{-}A^{11})_s\text{-}X^{11}\text{-}A^{12}\text{-} \quad (a\text{-}1)$$

wherein $X^{10}$ and $X^{11}$ each independently represents —O—, —NH—, —CO—, —CO—O—, —O—CO—, —CO—NH— or —NH—CO—, $A^{10}$, $A^{11}$ and $A^{12}$ each independently represent a C1-C5 divalent aliphatic hydrocarbon group optionally having one or more substituents, and s represents 0 or 1, and $Z^2$ represents a single bond or —CO—.

* * * * *